US007585944B2

(12) United States Patent
Apel-Birkhold et al.

(10) Patent No.: US 7,585,944 B2
(45) Date of Patent: Sep. 8, 2009

(54) **TOXIN COMPLEX PROTEINS AND GENES FROM *XENORHABDUS BOVIENII***

(75) Inventors: Patricia C. Apel-Birkhold, Napoleon, OH (US); Timothy D. Hey, Zionsville, IN (US); Joel J. Sheets, Zionsville, IN (US); Thomas Meade, Zionsville, IN (US); Ze-Sheng Li, Westfield, IN (US); Justin M. Lira, Fishers, IN (US); Sean M. Russell, Indianapolis, IN (US); Robin L. Thompson, Indianapolis, IN (US); Jon C. Mitchell, West Lafayette, IN (US); Kristin Fencil, Indianapolis, IN (US)

(73) Assignee: Dow Agrosciences LLC, Indianapolis, IN (US)

( * ) Notice: Subject to any disclaimer, the term of this patent is extended or adjusted under 35 U.S.C. 154(b) by 0 days.

(21) Appl. No.: 11/857,073

(22) Filed: Sep. 18, 2007

(65) Prior Publication Data

US 2008/0058248 A1 Mar. 6, 2008

Related U.S. Application Data

(62) Division of application No. 11/020,848, filed on Dec. 23, 2004, now Pat. No. 7,285,632.

(60) Provisional application No. 60/534,893, filed on Jan. 7, 2004.

(51) Int. Cl.
*C07K 1/00* (2006.01)
*C07K 14/00* (2006.01)
*C07K 14/20* (2006.01)

(52) U.S. Cl. .................................. 530/350; 530/825

(58) Field of Classification Search ............... None
See application file for complete search history.

(56) References Cited

U.S. PATENT DOCUMENTS

2004/0208907 A1  10/2004  Hey et al.

FOREIGN PATENT DOCUMENTS

| WO | WO 99/42589 A2 | 8/1999 |
| WO | WO 2004/067727 A2 | 8/2004 |
| WO | WO 2005/084355 A2 | 9/2005 |

OTHER PUBLICATIONS

"*Photorhabdus luminescens* protein sequence #3623", Database Geneseq [Online], Nov. 20, 2003, Database accession No. ABM70526.
"*Photorhabdus luminescens* protein sequence #3311", Database Geneseq [Online], Nov. 20, 2003, Database accession No. ABM70214.
"*Photorhabdus luminescens* protein sequence #3326", Database Geneseq [Online], Nov. 20, 2003, Database accession No. ABM70229.
Morgan, Jaw et al, "Sequence analysis of insecticidal genes from *Xenorhabdus nematophilus* PMF1296", Applied & Environmental Microbiology, US, May 2001, p. 2062-2069, V.67, N.5.
Duchaud, Eric et al, "The genome sequence of the entomopathogenic bacterium *Photorhabdus luminescens*", Nature Biotechnology, Nov. 2003, pp. 1307-1313, vol. 21, No. 11.
Bowen, D et al, "Insecticidal Toxins From The Bacterium *Photorhabdus luminescens*", Science, American Assoc. For the Advancement of Science, Jun. 26, 1998, p. 2129-2132, vol. 280.
Waterfield, N R et al, "The tc genes of *Photorhabdus*: A growing family", Trends in Microbiology, Elsevier Science LTD, Kidlington, GB, Apr. 2001, p. 185-191, vol. 9., No. 4.
Waterfield, Nicholas R. et al, "Genomic islands in *Photorhabdus*", Trends in Microbiology, Elsevier Science, Ltd., Kidlington, GB, Dec. 2002, pp. 541-545, vol. 10, No. 12.

*Primary Examiner*—Medina A Ibrahim
(74) *Attorney, Agent, or Firm*—Jay Sanders; Donald Stuart

(57) ABSTRACT

The subject invention relates to novel *Xenorhabdus* toxin complex (TC) proteins and genes that encode these proteins. More specifically, the subject invention relates to TC genes and proteins obtainable from *Xenorhabdus bovienii* strain ILM104.

4 Claims, 1 Drawing Sheet

*Photorhabdus*

*tca*

*tcb*

*tcc*

*tcd*

TOXIN COMPLEX PROTEINS AND GENES FROM *XENORHABDUS BOVIENII*

CROSS-REFERENCE TO RELATED APPLICATION

This application is a divisional of U.S. Ser. No. 11/020,848, filed Dec. 23, 2004, which claims the benefit of provisional application Ser. No. 60/534,893, filed Jan. 7, 2004.

BACKGROUND OF THE INVENTION

Insects and other pests cost farmers billions of dollars annually in crop losses and in the expense of keeping these pests under control. The losses caused by insect pests in agricultural production environments include decreases in crop yield, reduced crop quality, and increased harvesting costs. Insect pests are also a burden to vegetable and fruit growers, to producers of ornamental flowers, and to home gardeners and homeowners.

Cultivation methods, such as crop rotation and the application of high levels of nitrogen fertilizers, have partially addressed problems caused by agricultural pests. However, various demands on the utilization of farmland restrict the use of crop rotation. In addition, overwintering traits of some insects are disrupting crop rotations in some areas.

Thus, synthetic chemical insecticides are relied upon most heavily to achieve a sufficient level of control. However, the use of synthetic chemical insecticides has several drawbacks. For example, the use of these chemicals can adversely affect many beneficial insects. Target insects have also developed resistance to some chemical pesticides. Furthermore, rain and improper calibration of insecticide application equipment can result in poor control. The use of insecticides often raises environmental concerns such as contamination of soil and water supplies when not used properly, and residues can also remain on treated fruits and vegetables. Working with some insecticides can also pose hazards to the persons applying them. Stringent new restrictions on the use of pesticides and the elimination of some effective pesticides could limit effective options for controlling damaging and costly pests.

The replacement of synthetic chemical pesticides, or combination of these agents with biological pesticides, could reduce the levels of toxic chemicals in the environment. Some biological pesticidal agents that are now being used with some success are derived from the soil microbe *Bacillus thuringiensis* (B.t.). While most B.t. strains do not exhibit pesticidal activity, some B.t. strains produce proteins that are highly toxic to pests, such as insects, and are specific in their toxic activity. Genes that encode δ-endotoxin proteins have been isolated. Other species of *Bacillus* also produce pesticidal proteins.

Höfte and Whiteley classified B.t. crystal proteins into four major classes (Höfte, H., H. R. Whiteley [1989] *Microbiological Reviews* 52(2):242-255). The classes were CryI (Lepidoptera-specific), CryI (Lepidoptera- and Diptera-specific), CryIII (Coleoptera-specific), and CryIV (Diptera-specific). The discovery of strains specifically toxic to other pests has been reported. For example, CryV and CryVI have been proposed to designate a class of toxin genes that are nematode-specific.

The 1989 nomenclature and classification scheme of Höfte and Whiteley for crystal proteins was based on both the deduced amino acid sequence and the activity spectrum of the toxin. That system was adapted to cover 14 different types of toxin genes divided into five major classes. The 1989 nomenclature scheme became unworkable as more and more genes were discovered that encoded proteins with varying spectrums of pesticidal activity. Thus, a revised nomenclature scheme was adopted, which is based solely on amino acid identity (Crickmore et al., 1998, *Microbiology and Molecular Biology Reviews* 62:807-813).

Recombinant DNA-based B.t. products have been produced and approved for use. In addition, with the use of genetic engineering techniques, various approaches for delivering these toxins to agricultural environments are being perfected. These include the use of plants genetically engineered with toxin genes for insect resistance and the use of stabilized intact microbial cells as toxin delivery vehicles. Thus, isolated *Bacillus* toxin genes are becoming commercially valuable.

B.t. protein toxins were initially formulated as sprayable insect control agents. A relatively more recent application of B.t. technology has been to isolate and transform plants with genes that encode these toxins. Transgenic plants subsequently produce the toxins, thereby providing insect control. See U.S. Pat. Nos. 5,380,831; 5,567,600; and 5,567,862 to Mycogen Corporation. Transgenic B.t. plants are quite efficacious, and usage is predicted to be high in some crops and areas.

There are some obstacles to the successful agricultural use of *Bacillus* (and other biological) pesticidal proteins. Certain insects can be refractory to the effects of *Bacillus* toxins. Insects such as boll weevils, black cutworm, and *Helicoverpa zea*, as well as adult insects of most species, heretofore have demonstrated no significant sensitivity to many B.t. δ-endotoxins.

Another potential obstacle is the development of resistance to B.t. toxins by insects. The potential for wide-spread use of B.t. plants has caused some concern that resistance management issues may arise more quickly than with traditional sprayable applications. While a number of insects have been selected for resistance to B t. toxins in the laboratory, only the diamondback moth (*Plutella xylostella*) has demonstrated resistance in a field setting (Ferre, J. and Van Rie, J., *Annu. Rev. Entomol.* 47:501-533, 2002).

Resistance management strategies in B.t. transgene plant technology have become of great interest. Several strategies have been suggested for preserving the ability to effectively use *B. thuringiensis* toxins. These strategies include high dose with refuge, and alternation with, or co-deployment of, different toxins (McGaughey et al. (1998), "B.t. Resistance Management," *Nature Biotechnol.* 16:144-146), as in a natural bacterium, for example.

Thus, there remains a great need for developing additional genes that can be expressed in plants in order to effectively control various insects. In addition to continually trying to discover new B.t. toxins (which is becoming increasingly difficult due to the numerous B.t. toxins that have already been discovered), it would be quite desirable to discover other bacterial sources (distinct from B.t.) that produce toxins that could be used in transgenic plant strategies.

The relatively more recent efforts to clone insecticidal toxin genes from the *Photorhabdus/Xenorhabdus* group of bacteria present potential alternatives to toxins derived from *B. thuringiensis*. The genus *Xenorhabdus* is taxonomically defined as a member of the Family Enterobacteriaceae, although it has certain traits atypical of this family. For example, strains of this genus are typically nitrate reduction negative and catalase negative. *Xenorhabdus* has only recently been subdivided to create a second genus, *Photorhabdus*, which is comprised of three species, *Photorhabdus asymbiotica*, *Photorhabdus temperata*, and *P. luminescens*. *P. luminescens* has three recognized subspecies, *Photorhabdus* luminescens subsp. akhurstii, Photorhabdus luminescens subsp. laumondii, and Photorhabdus luminescens subsp. luminescens* (Type species). (Fischer-Le Saux, M., Viallard, V., Brunel, B., Normand, P., Boemare, N. E. Title Polyphasic classification of the genus *Photorhabdus* and proposal of new taxa: *P. luminescens* subsp. *luminescens* subsp. *nov., P. luminescens* subsp. *akhurstii* subsp. *nov., P. luminescens* subsp. *laumondii* subsp. *nov., P. temperata* sp. *nov., P. temperata* subsp. *temperata* subsp. *nov.* and *P. asymbiotica* sp. *nov. Int. J. Syst. Bacteriol.* 49; 1645-1656, (1999)). This differentiation is based on several distinguishing characteristics easily identifiable by the skilled artisan. These differences include the following: DNA-DNA characterization studies; phenotypic presence (*Photorhabdus*) or absence (*Xenorhabdus*) of catalase activity; presence (*Photorhabdus*) or absence (*Xenorhabdus*) of bioluminescence; the Family of the nematode host in that *Xenorhabdus* is found in Steinernematidae and *Photorhabdus* is found in Heterorhabditidae); as well as comparative, cellular fatty-acid analyses (Janse et al. 1990*, Lett. Appl. Microbiol.* 10, 131-135; Suzuki et al. 1990*, J. Gen. Appl. Microbiol.,* 36, 393-401). In addition, recent molecular studies focused on sequence (Rainey et al. 1995*, Int. J. Syst. Bacteriol.,* 45, 379-381) and restriction analysis (Brunel et al., 1997*, App. Environ. Micro.,* 63, 574-580) of 16S rRNA genes also support the separation of these two genera.

The expected traits for *Xenorhabdus* are the following: Gram stain negative rods, white to yellow/brown colony pigmentation, presence of inclusion bodies, absence of catalase, inability to reduce nitrate, absence of bioluminescence, ability to uptake dye from medium, positive gelatin hydrolysis, growth on Enterobacteriaceae selective media, growth temperature below 37° C., survival under anaerobic conditions, and motility.

Currently, the bacterial genus *Xenorhabdus* is comprised of four recognized species, *Xenorhabdus nematophilus, Xenorhabdus poinarii, Xenorhabdus bovienii* and *Xenorhabdus beddingii* (Brunel et al., 1997*, App. Environ. Micro.,* 63, 574-580). A variety of related strains have been described in the literature (e.g., Akhurst and Boemare 1988 *J. Gen. Microbiol.,* 134, 1835-1845; Boemare et al. 1993 *Int. J. Syst. Bacteriol* 43, pp. 249-255; Putz et al. 1990*, Appl. Environ. Microbiol.,* 56, 181-186, Brunel et al., 1997*, App. Environ. Micro.,* 63, 574-580, Rainey et al. 1995*, Int. A Syst. Bacteriol,* 45, 379-381).

*Photorhabdus* and *Xenorhabdus* spp. are Gram-negative bacteria that entomopathogenically and symbiotically associate with soil nematodes. These bacteria are found in the gut of entomopathogenic nematodes that invade and kill insects. When the nematode invades an insect host, the bacteria are released into the insect haemocoel (the open circulatory system), and both the bacteria and the nematode undergo multiple rounds of replication; the insect host typically dies. These bacteria can be cultured away from their nematode hosts. For a more detailed discussion of these bacteria, see Forst and Nealson, 60 *Microbiol. Rev.* 1 (1996), pp. 21-43. Unfortunately, as reported in a number of articles, the bacteria only had pesticidal activity when injected into insect larvae and did not exhibit biological activity when delivered orally.

*Xenorhabdus* and *Photorhabus* bacteria secrete a wide variety of substances into the culture medium. See R. H. ffrench-Constant et al. 66 AEM No. 8, pp. 3310-3329 (August 2000), for a review of various factors involved in *Photorhabdus* virulence of insects.

It has been difficult to effectively exploit the insecticidal properties of the nematode or its bacterial symbiont. Thus, proteinaceous agents from *Photorhabdus/Xenorhabdus* bacteria that have oral activity are desirable so that the products produced therefrom could be formulated as a sprayable insecticide, or the genes encoding said proteinaceous agents could be isolated and used in the production of transgenic plants.

There has been substantial progress in the cloning of genes encoding insecticidal toxins from both *Photorhabdus* luminescens and *Xenorhabdus nematophilus*. Toxin-complex encoding genes from *P. luminescens* were examined first. See WO 98/08932. Parallel genes were more recently cloned from *X. nematophilus*. Morgan et al., *Applied and Environmental Microbiology* 2001, 67:20062-69. WO 95/00647 relates to the use of *Xenorhabdus* protein toxin to control insects, but it does not recognize orally active toxins. WO 98/08388 relates to orally administered pesticidal agents from *Xenorhabdus*. U.S. Pat. No. 6,048,838 relates to protein toxins/toxin complexes, having oral activity, obtainable from *Xenorhabdus* species and strains.

Four different toxin complexes (TCs)—Tca, Tcb, Tcc and Tcd—have been identified in *Photorhabdus* spp. Each of these toxin complexes resolves as either a single or dimeric species on a native agarose gel but resolution on a denaturing gel reveals that each complex consists of a range of species between 25-280 kDa. The ORFs that encode the typical TCs from *Photorhabdus*, together with protease cleavage sites (vertical arrows), are illustrated in FIG. 1. See also R. H. ffrench-Constant and Bowen, 57 *Cell. Mol. Life. Sci.* 828-833 (2000).

Genomic libraries of *P. luminescens* were screened with DNA probes and with monoclonal and/or polyclonal antibodies raised against the toxins. Four tc loci were cloned: tca, tcb, tcc and tcd. The tca locus is a putative operon of three open reading frames (ORFs), tcaA, tcaB, and tcaC, transcribed from the same DNA strand, with a smaller terminal ORF (tcaZ) transcribed in the opposite direction. The tcc locus also is comprised of three ORFs putatively transcribed in the same direction (tccA, tccB, and tccC). The tcb locus is a single large ORF (tcbA), and the tcd locus is composed of two ORFs (tcdC and tcdB); tcbA and tcdA, each about 7.5 kb, encode large insect toxins. TcdB has some level of homology to TcaC. It was determined that many of these gene products were cleaved by proteases. For example, both TcbA and TcdA are cleaved into three fragments termed i, ii and iii (e.g. TcbAi, TcbAii and TcbAiii). Products of the tca and tcc ORFs are also cleaved. See FIG. 1. See also R. H. ffrench-Constant and D. J. Bowen, *Current Opinions in Microbiology,* 1999, 12:284-288.

Bioassays of the Tca toxin complexes revealed them to be highly toxic to first instar tomato hornworms (*Manduca sexta*) when given orally ($LD_{50}$ of 875 ng per square centimeter of artificial diet). R. H. ffrench-Constant and Bowen 1999. Feeding was inhibited at Tca doses as low as 40 ng/cm$^2$. Given the high predicted molecular weight of Tca, on a molar basis, *P. luminescens* toxins are highly active and relatively few molecules appear to be necessary to exert a toxic effect. R. H. ffrench-Constant and Bowen, *Current Opinions in Microbiology,* 1999, 12:284-288.

None of the four loci showed overall similarity to any sequences of known function in GenBank. Regions of sequence similarity raised some suggestion that these proteins (TcaC and TccA) may overcome insect immunity by attacking insect hemocytes. R. H. ffrench-Constant and Bowen, *Current Opinions in Microbiology,* 1999, 12:284-288.

TcaB, TebA and TcdA all show amino acid conservation (~50% identity), compared with each other, immediately around their predicted protease cleavage sites. This conservation between three different Tc proteins suggests that they may all be processed by the same or similar proteases. TcbA and TcdA also share ~50% identity overall, as well as a similar predicted pattern of both carboxy- and amino-terminal cleavage. It was postulated that these proteins might thus be homologs of one another. Furthermore, the similar, large size of TcbA and TcdA, and also the fact that both toxins appear to act on the gut of the insect, may suggest similar modes of action. R. H. ffrench-Constant and Bowen, *Current Opinions in Microbiology,* 1999, 12:284-288.

Deletion/knock-out studies suggest that products of the tca and tcd loci account for the majority of oral toxicity to lepidopterans. Deletion of either of the tca or tcd genes greatly reduced oral activity against *Manduca sexta.* That is, products of the tca and tcd loci are oral lepidopteran toxins on their own; their combined effect contributed most of the secreted oral activity. R. H. ffrench-Constant and D. J. Bowen, 57 *Cell. Mol. Life. Sci.* 831 (2000). Interestingly, deletion of either of the tcb or tee loci alone also reduces mortality, suggesting that there may be complex interactions among the different gene products. Thus, products of the tcc locus may enhance the toxicity of tcd products. Alternatively, tcd products may modulate the toxicity of tca products and possibly other complexes. Noting that the above relates to oral activity against a single insect species, tcb or tcc loci may produce toxins that are more active against other groups of insects (or active via injection directly into the insect haemocoel—the normal route of delivery when secreted by the bacteria in vivo). R. H. ffrench-Constant and Bowen, *Current Opinions in Microbiology,* 1999, 12:284-288.

The insect midgut epithelium contains both columnar (structural) and goblet (secretory) cells. Ingestion of tca products by *M. sexta* leads to apical swelling and blebbing of large cytoplasmic vesicles by the columnar cells, leading to the eventual extrusion of cell nuclei in vesicles into the gut lumen. Goblet cells are also apparently affected in the same fashion. Products of tca act on the insect midgut following either oral delivery or injection. R. H. ffrench-Constant and D. J. Bowen, *Current Opinions in Microbiology,* 1999, 12:284-288. Purified tca products have shown oral toxicity against *Manduca sexta* ($LD_{50}$ of 875 ng/cm²). R. H. ffrench-Constant and D. J. Bowen, 57 *Cell. Mol. Life. Sci.* 828-833 (2000).

WO 99/42589 and U.S. Pat. No. 6,281,413 disclose TC-like ORFs from *Photorhabdus luminescens.* WO 00/30453 and WO 00/42855 disclose TC-like proteins from *Xenorhabdus.* WO 99/03328 and WO 99/54472 (and U.S. Pat. Nos. 6,174,860 and 6,277,823) relate to other toxins from *Xenorhabdus* and *Photorhabdus.*

While the exact molecular interactions of the TCs with each other, and their mechanism(s) of action, are not currently understood, it is known, for example, that the Tca toxin complex of *Photorhabdus* is toxic to *Manduca sexta.* In addition, some TC proteins are known to have "stand alone" insecticidal activity, while other TC proteins are known to potentiate or enhance the activity of the stand-alone toxins. It is known that the TcdA protein is active, alone, against *Manduca sexta,* but that TcdB and TccC, together, can be used (in conjunction with TcdA) to greatly enhance the activity of TcdA. TcbA is the other main, stand-alone toxin from *Photorhabdus.* The activity of this toxin (TcbA) can also be greatly enhanced by TcdB-together with TccC-like proteins.

| Photorhabdus TC protein | Photorhabdus strain W14 nomenclature | Some homology to: |
|---|---|---|
| TcaA | Toxin C | TccA |
| TcaB | | TccB |
| TcaC | | TcdB |
| Tcb | Toxin B | |
| TccA | Toxin D | TcdA N terminus |
| TccB | | TcdA C terminus |
| TccC | | |
| TcdA | Toxin A | TccA + TccB |
| TcdB | | TcaC |

Some *Photorhabdus* TC proteins have some level of sequence homology with other *Photorhabdus* TC proteins. As indicated above, TccA has some level of homology with the N terminus of TcdA, and TccB has some level of homology with the C terminus of TcdA. Furthermore, TcdA is about 280 kDa, and TccA together with TccB are of about the same size, if combined, as that of TcdA. Though TccA and TccB are much less active on SCR than TcdA, TccA and TccB from *Photorhabdus* strain W14 are called "Toxin D." "Toxin A" (TcdA), "Toxin B" (Tcb or TcbA), and "Toxin C" (TcaA and TcaB) are also indicated above.

Furthermore, TcaA has some level of homology with TccA and likewise with the N terminus of TcdA. Still further, TcaB has some level of homology with TccB and likewise with the N terminus of TcdA. TcdB has a significant level of similarity to TcaC.

Relatively recent cloning efforts in *Xenorhabdus nematophilus* also appear to have identified novel insecticidal toxin genes with homology to the *P. luminescens* tc loci. See, e.g., WO 98/08388 and Morgan et al., *Applied and Environmental Microbiology* 2001, 67:20062-69. In R. H. ffrench-Constant and D. J. Bowen *Current Opinions in Microbiology,* 1999, 12:284-288, cosmid clones were screened directly for oral toxicity to another lepidopteran, *Pieris brassicae.* One orally toxic cosmid clone was sequenced. Analysis of the sequence in that cosmid suggested that there are five different ORF's with similarity to *Photorhabdus tc* genes; orf2 and orf5 both have some level of sequence relatedness to both tcbA and tcdA, whereas orf1 is similar to tccB, orf3 is similar to tccC and orf4 is similar to tcaC. Importantly, a number of these predicted ORFs also share the putative cleavage site documented in *P. luminescens,* suggesting that active toxins may also be proteolytically processed.

There are five typical TC proteins from *Xenorhabdus,* XptA1, XptA2, XptB1, XptC1, and XptD1. XptA1 is a "stand-alone" toxin-XptA2 is the other TC protein from *Xenorhabdus* that has stand-alone toxin activity. XptB1 and XptC1 are the *Xenorhahdus* potentiators that can enhance the activity of either (or both) of the XptA toxins. XptD1 has some level of homology with TccB.

XptC1 was known to have some level of similarity to TcaC. The XptA2 protein of *Xenorhabdus* was known to have some degree of similarity to the Tcd protein. XptB1 has some level of similarity to TccC.

The finding of somewhat similar, toxin-encoding loci in these two different bacteria is interesting in terms of the possible origins of these virulence genes. The *X. nematophilus* cosmid also appears to contain transposase-like sequences whose presence may suggest that these loci can be transferred horizontally between different strains or species of bacteria. A range of such transfer events may also explain the apparently different genomic organization of the tc operons in the two different bacteria. Further, only a subset of *X. nematophilus* and *P. luminescens* strains appear toxic to *M. sexta*, suggesting either that different strains lack the tc genes or that they carry a different tc gene compliment. Detailed analysis of both strain and toxin phylogeny within, and between, these bacterial species should help clarify the likely origin of the toxin genes and how they are maintained in different bacterial populations. R. H. ffrench-Constant and Bowen, *Current Opinions in Microbiology*, 1999, 12:284-288.

TC proteins and genes have more recently been described from other insect-associated bacteria such as *Serratia entomophila*, an insect pathogen. Waterfield et al., *TRENDS in Microbiology*, Vol. 9, No. 4, April 2001.

In summary, toxin complex proteins from *P. luminescens* and *X. nematophilus* appear to have little homology to previously identified bacterial toxins and should provide useful alternatives to toxins derived from *B. thuringiensis*. Although they have similar toxic effects on the insect midgut to other orally active toxins, their precise mode of action remains obscure. Future work could clarify their mechanism of action.

Bacteria of the genus *Paenibacillus* are distinguishable from other bacteria by distinctive rRNA and phenotypic characteristics (C. Ash et al. (1993), "Molecular identification of rRNA group 3 bacilli (Ash, Farrow, Wallbanks and Collins) using a PCR probe test: Proposal for the creation of a new genus *Paenibacillus*," *Antonie Van Leeuwenhoek* 64:253-260). Some species in this genus are known to be pathogenic to honeybees (*Paenibacillus larvae*) and to scarab beetle grubs (*P. popilliae* and *P. lentimorbus.*) *P. larvae*, *P. popilliae*, and *P. lentimorbus* are considered obligate insect pathogens involved with milky disease of scarab beetles (D. P. Stahly et al. (1992), "The genus *Bacillus*: insect pathogens," p. 1697-1745, In A. Balows et at, ed., *The Procaryotes*, $2^{nd}$ Ed., Vol. 2, Springer-Verlag, New York, N.Y.).

A crystal protein, Cry18, has been identified in strains of *P. popilliae* and *P. lentimorbus*. Cry18 has scarab and grub toxicity, and has about 40% identity to CCy2 proteins (Zhang et al., 1997; Harrison et al., 2000).

TC proteins and lepidopteran-toxic Cry proteins have very recently been discovered in *Paenibacillus*. See U.S. Ser. No. 60/392,633 (Bintrim et al.), filed Jun. 28, 2002.

Although some *Xenorhabdus* TC proteins were found to "correspond" (have a similar function and some level of sequence homology) to some of the *Photorhabdus* TC proteins, the "corresponding" proteins share only about 40% (approximately) sequence identity with each other. This is also true for the more recently discovered TC proteins from *Paenibacillus* (those proteins and that discovery are the subject of co-pending U.S. Ser. No. 60/392,633).

In light of concerns about insects developing resistance to a given pesticidal toxin, and in light of other concerns—some of which are discussed above, there is a continuing need for the discovery of new insecticidal toxins and other proteins that can be used to control insects.

BRIEF SUMMARY OF THE INVENTION

The subject invention relates to novel *Xenorhabdus* toxin complex (TC) proteins and genes that encode these proteins. More specifically, the subject invention relates to TC proteins and genes obtainable from *Xenorhabdus bovienii* strain ILM104.

BRIEF DESCRIPTION OF THE SEQUENCES

Figure 1:
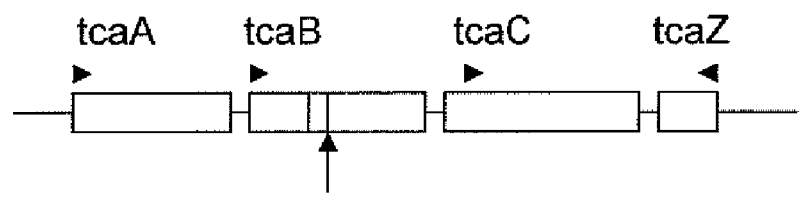
FIG. 1 shows the TC operon from *Photorhabdus*.
Figure 1:
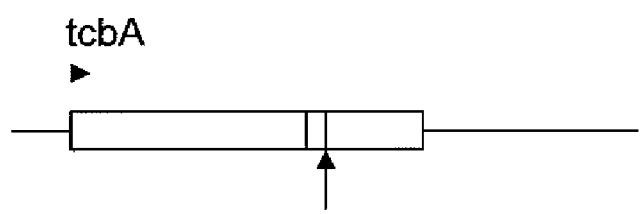
Figure 1:
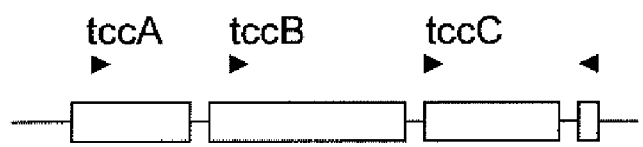
Figure 1:
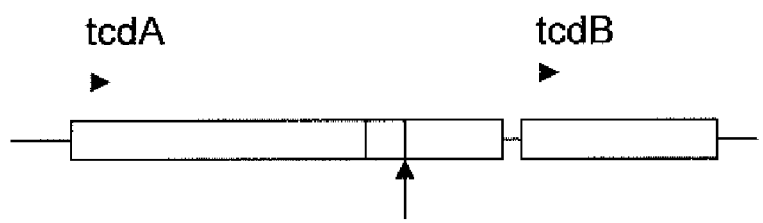

SEQ ID NO:1 is the native $xptB1_{xb}$ coding region (4521 bases).

SEQ ID NO:2 is the native $XptB1_{xb}$ protein encoded by SEQ ID NO:1 (1506 amino acids).

SEQ ID NO:3 is the native $xptC1_{xb}$ coding region (2889 bases).

SEQ ID NO:4 is the native $XptC1_{xb}$ protein encoded by SEQ ID NO:3 (962 amino acids).

SEQ ID NO:5 is the native $XptA1_{xb}$ coding region (partial) (3822 bases).

SEQ ID NO:6 is the native $XptA1_{xb}$ protein encoded by SEQ ID NO:5 (partial) (1273 amino acids).

SEQ ID NO:7 is the Xba I to Xho I fragment of expression plasmid pDAB6031 comprising the native $xptB1_{xb}$ coding region, where bases 40 to 4557 encode the protein of SEQ ID NO:2 (4595 bases).

SEQ ID NO:8 is the Xba I to Xho I fragment of expression plasmid pDAB6032 comprising the native $xptC1_{xb}$ coding region, where bases 40 to 2925 encode the protein of SEQ ID NO:4 (2947 bases).

SEQ ID NO:9 is the Xba I to Xho I fragment of expression plasmid pDAB6033 comprising the native $xptB1_{xb}$ and Native $xptC1_{xb}$ coding regions, where bases 40 to 4557 encode the protein of SEQ ID NO:2, and bases 4601 to 7486 encode the protein of SEQ ID NO:4 (7508 bases).

SEQ ID NO:10 is the full-length coding sequence of the new Class A gene, named $xptA1_{xb}$.

SEQ ID NO:11 is the protein ($XptA1_{xb}$) encoded by the reading frame of SEQ ID NO:10.

DETAILED DESCRIPTION OF THE INVENTION

The subject invention relates to novel *Xenorhabdus* toxin complex (TC) proteins and genes that encode these proteins. More specifically, the subject invention relates to TC genes and proteins obtainable from *Xenorhabdus bovienii* strain ILM104.

There are three main types of TC proteins. As referred to herein, Class A proteins ("Protein A") are stand alone toxins. Native Class A proteins are approximately 280 kDa. Class B proteins ("Protein B") and Class C proteins ("Protein C") enhance the toxicity of Class A proteins. As used referred to herein, native Class B proteins are approximately 170 kDa, and native Class C proteins are approximately 112 kDa. Examples of Class A proteins are TcbA, TcdA, XptA1, and XptA2. Examples of Class B proteins are TcaC, TcdB, $XptB1_{Xb}$, and $XptC1_{Wi}$. Examples of Class C proteins are TccC, $XptC1_{Xb}$, and $XptB1_{Wi}$.

It was shown previously (U.S. Pat. No. 6,048,838) that *Xenorhabdus* strain ILM104 (NRRL B-30021, deposited Apr. 30, 1998) produced extracellular proteins with oral insecticidal activity against members of the insect orders Coleoptera, Lepidoptera, Diptera, and Acarina. Two specific TC potentiators and a TC toxin (and genes encoding them) obtainable from strain ILM104 are disclosed herein.

A polynucleotide of the subject invention can be inserted into the genome of a plant so that the plant produces the protein encoded by the polynucleotide. Insects consuming the plant tissues that produce (and contain) this protein thereby contact the protein and will be controlled in this manner. The TC protein genes can be used in this (i.e., expression in plants) and other manners to control insects and other like pests. Preferably, a plant is produced that expresses a gene of the subject invention so that one or more proteins of the subject invention are produced by and preferably present in the cells of the plant. The plant can be constructed to co-express the subject genes so that the resulting proteins potentiate or enhance XptA1 and/or XptA2 TC protein toxins, for example.

Other methods of administering the subject proteins to insects and other pests are well known in the art. Furthermore, the subject proteins are not limited to use with each other; they can be used individually (or in combination) with other proteins (such as B.t. toxins), as would be known in the art.

Proteins and toxins. The present invention provides easily administered, functional proteins. The present invention also provides a method for delivering insecticidal toxins that are functionally active and effective against many orders of insects, preferably lepidopteran insects. By "functional activity" (or "active against") it is meant herein that the protein toxins function as orally active insect control agents (alone or in combination with other proteins), that the proteins have a toxic effect (alone or in combination with other proteins), or are able to disrupt or deter insect growth and/or feeding which may or may not cause death of the insect. When an insect comes into contact with an effective amount of a "toxin" of the subject invention delivered via transgenic plant expression, formulated protein composition(s), sprayable protein composition(s), a bait matrix or other delivery system, the results are typically death of the insect, inhibition of the growth and/or proliferation of the insect, and/or prevention of the insects from feeding upon the source (preferably a transgenic plant) that makes the toxins available to the insects. Functional proteins of the subject invention can also work together or alone to enhance or improve the activity of one or more other toxin proteins. The terms "toxic," "toxicity," or "toxin" as used herein are meant to convey that the subject "toxins" have "functional activity" as defined herein.

Complete lethality to feeding insects is preferred but is not required to achieve functional activity. If an insect avoids the toxin or ceases feeding, that avoidance will be useful in some applications, even if the effects are sublethal or lethality is delayed or indirect. For example, if insect resistant transgenic plants are desired, the reluctance of insects to feed on the plants is as useful as lethal toxicity to the insects because the ultimate objective is avoiding insect-induced plant damage.

There are many other ways in which toxins can be incorporated into an insect's diet. For example, it is possible to adulterate the larval food source with the toxic protein by spraying the food with a protein solution, as disclosed herein. Alternatively, the purified protein could be genetically engineered into an otherwise harmless bacterium, which could then be grown in culture, and either applied to the food source or allowed to reside in the soil in an area in which insect eradication was desirable. Also, the protein could be genetically engineered directly into an insect food source. For instance, the major food source for many insect larvae is plant material. Therefore the genes encoding toxins can be transferred to plant material so that said plant material expresses the toxin of interest.

Transfer of the functional activity to plant or bacterial systems typically requires nucleic acid sequences, encoding the amino acid sequences for the toxins, integrated into a protein expression vector appropriate to the host in which the vector will reside. One way to obtain a nucleic acid sequence encoding a protein with functional activity is to isolate the native genetic material from the bacterial species which produce the toxins, using information deduced from the toxin's amino acid sequence, as disclosed herein. The native sequences can be optimized for expression in plants, for example, as discussed in more detail below. Optimized polynucleotide can also be designed based on the protein sequence.

The subject invention provides new classes of toxins having advantageous pesticidal activities. One way to characterize these classes of toxins and the polynucleotides that encode them is by defining a polynucleotide by its ability to hybridize, under a range of specified conditions, with an exemplified nucleotide sequence (the complement thereof and/or a probe or probes derived from either strand) and/or by their ability to be amplified by PCR using primers derived from the exemplified sequences.

There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or to fragments of these toxins, can be readily prepared using standard procedures. Such antibodies are included as an aspect of the subject invention. Toxins of the subject invention can be obtained from a variety of sources/source microorganisms.

One skilled in the art would readily recognize that toxins (and genes) of the subject invention can be obtained from a variety of sources. A toxin "from" or "obtainable from" the subject isolate means that the toxin (or a similar toxin) can be obtained from *X. bovienii* strain ILM104 or some other source, such as another bacterial strain or a plant. For example, one skilled in the art will readily recognize that, given the disclosure of a bacterial gene and toxin, a plant can be engineered to produce the toxin. Antibody preparations, nucleic acid probes (DNA and RNA), and the like may be prepared using the polynucleotide and/or amino acid sequences disclosed herein and used to screen and recover other toxin genes from other (natural) sources.

Polynucleotides and probes. The subject invention further provides nucleotide sequences that encode the toxins of the subject invention. The subject invention further provides methods of identifying and characterizing genes that encode pesticidal toxins. In one embodiment, the subject invention provides unique nucleotide sequences that are useful as hybridization probes and/or primers for PCR techniques. The primers produce characteristic gene fragments that can be used in the identification, characterization, and/or isolation of specific toxin genes. The nucleotide sequences of the subject invention encode toxins that are distinct from previously described toxins.

The polynucleotides of the subject invention can be used to form complete "genes" to encode proteins or peptides in a desired host cell. For example, as the skilled artisan would readily recognize, the subject polynucleotides can be appropriately placed under the control of a promoter in a host of interest, as is readily known in the art.

As the skilled artisan knows, DNA typically exists in a double-stranded form. In this arrangement, one strand is complementary to the other strand and vice versa. As DNA is replicated in a plant (for example), additional complementary strands of DNA are produced. The "coding strand" is often used in the art to refer to the strand that binds with the anti-sense strand. The mRNA is transcribed from the "anti-sense" strand of DNA. The "sense" or "coding" strand has a series of codons (a codon is three nucleotides that can be read as a three-residue unit to specify a particular amino acid) that can be read as an open reading frame (ORF) to form a protein or peptide of interest. In order to produce a protein in vivo, a strand of DNA is typically transcribed into a complementary strand of mRNA which is used as the template for the protein. Thus, the subject invention includes the use of the exemplified polynucleotides shown in the attached sequence listing and/or equivalents including the complementary strands. RNA and PNA (peptide nucleic acids) that are functionally equivalent to the exemplified DNA are included in the subject invention.

In one embodiment of the subject invention, bacterial isolates can be cultivated under conditions resulting in high multiplication of the microbe. After treating the microbe to provide single-stranded genomic nucleic acid, the DNA can be contacted with the primers of the invention and subjected to PCR amplification. Characteristic fragments of toxin-encoding genes will be amplified by the procedure, thus identifying the presence of the toxin-encoding gene(s).

Further aspects of the subject invention include genes and isolates identified using the methods and nucleotide sequences disclosed herein. The genes thus identified encode toxins active against pests.

Toxins and genes of the subject invention can be identified and obtained by using oligonucleotide probes, for example. These probes are detectable nucleotide sequences which may be detectable by virtue of an appropriate label or may be made inherently fluorescent as described in International Application No. WO 93/16094. The probes (and the polynucleotides of the subject invention) may be DNA, RNA, or PNA. In addition to adenine (A), cytosine (C), guanine (G), thymine (T), and uracil (U; for RNA molecules), synthetic probes (and polynucleotides) of the subject invention can also have inosine (a neutral base capable of pairing with all four bases; sometimes used in place of a mixture of all four bases in synthetic probes). Thus, where a synthetic, degenerate oligonucleotide is referred to herein, and "n" is used generically, "n" can be G, A, T, C, or inosine. Ambiguity codes as used herein are in accordance with standard IUPAC naming conventions as of the filing of the subject application (for example, R means A or C, Y means C or T, etc.).

As is well known in the art, if a probe molecule hybridizes with a nucleic acid sample, it can be reasonably assumed that the probe and sample have substantial homology/similarity/identity. Preferably, hybridization of the polynucleotide is first conducted followed by washes under conditions of low, moderate, or high stringency by techniques well-known in the art, as described in, for example, Keller, G. H., M. M. Manak (1987) *DNA Probes*, Stockton Press, New York, N.Y., pp. 169-170. For example, as stated therein, low stringency conditions can be achieved by first washing with 2×SSC (Standard Saline Citrate)/0.1% SDS (Sodium Dodecyl Sulfate) for 15 minutes at room temperature. Two washes are typically performed. Higher stringency can then be achieved by lowering the salt concentration and/or by raising the temperature. For example, the wash described above can be followed by two washings with 0.1×SSC/0.1% SDS for 15 minutes each at room temperature followed by subsequent washes with 0.1× SSC/0.1% SDS for 30 minutes each at 55° C. These temperatures can be used with other hybridization and wash protocols set forth herein and as would be known to one skilled in the art (SSPE can be used as the salt instead of SSC, for example). The 2×SSC/0.1% SDS can be prepared by adding 50 ml of 20×SSC and 5 ml of 10% SDS to 445 ml of water. 20×SSC can be prepared by combining NaCl (175.3 g/0.150 M), sodium citrate (88.2 g/0.015 M), and water to 1 liter, followed by adjusting pH to 7.0 with 10N NaOH. 10% SDS can be prepared by dissolving 10 g of SDS in 50 ml of autoclaved water, diluting to 100 ml, and aliquotting.

Detection of the probe provides a means for determining in a known manner whether hybridization has been maintained. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Hybridization characteristics of a molecule can be used to define polynucleotides of the subject invention. Thus the subject invention includes polynucleotides (and/or their complements, preferably their full complements) that hybridize with a polynucleotide exemplified herein.

As used herein "stringent" conditions for hybridization refers to conditions which achieve the same, or about the same, degree of specificity of hybridization as the conditions employed by the current applicants. Specifically, hybridization of immobilized DNA on Southern blots with $^{32}$P-labeled gene-specific probes was performed by standard methods (see, e.g., Maniatis, T., E. F. Fritsch, J. Sambrook [1982] *Molecular Cloning: A Laboratory Manual*, Cold Spring Harbor Laboratory, Cold Spring Harbor, N.Y.). In general, hybridization and subsequent washes were carried out under conditions that allowed for detection of target sequences. For double-stranded DNA gene probes, hybridization was carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A., K. A. Jacobs, T. H. Eickbush, P. T. Cherbas, and F. C. Kafatos [1983] *Methods of Enzymology*, R. Wu, L. Grossman and K. Moldave [eds.] Academic Press, New York 100:266-285);

$$Tm=81.5°\ C.+16.6\ \text{Log}\ [Na+]+0.41(\%\ G+C)-0.61(\%\ \text{formamide})-600/\text{length of duplex in base pairs}.$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10-20° C. below the melting temperature (Tm) of the hybrid in 6×SSPL, 5×Denhardt's solution, 0.1% SDS, 0.1 mg/ml denatured DNA. Tm for oligonucleotide probes was determined by the following formula:

$$Tm(°\ C.)=2(\text{number}\ T/A\ \text{base pairs})+4(\text{number}\ G/C\ \text{base pairs})$$

(Suggs, S. V., T. Miyake, E. H. Kawashime, M. J. Johnson, K. Itakura, and R. B. Wallace [1981] *ICN-UCLA Symp. Dev. Biol. Using Purified Genes*, D. D. Brown [ed.], Academic Press, New York, 23:683-693).

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used:

| | |
|---|---|
| Low: | 1 or 2x SSPE, room temperature |
| Low: | 1 or 2x SSPE, 42° C. |
| Moderate: | 0.2x or 1x SSPE, 65° C. |
| High: | 0.1x SSPE, 65° C. |

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

PCR technology. Polymerase Chain Reaction (PCR) is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," *Science* 230: 1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. The extension product of each primer can serve as a template for the other primer, so each cycle essentially doubles the amount of DNA fragment produced in the previous cycle. This results in the exponential accumulation of the specific target fragment, up to several million-fold in a few hours. By using a thermostable DNA polymerase such as Taq polymerase, isolated from the thermophilic bacterium *Thermus aquaticus*, the amplification process can be completely automated. Other enzymes which can be used are known to those skilled in the art.

The DNA sequences of the subject invention can be used as primers for PCR amplification. In performing PCR amplification, a certain degree of mismatch can be tolerated between primer and template. Therefore, mutations, deletions, and insertions (especially additions of nucleotides to the 5' end) of the exemplified primers fall within the scope of the subject invention. Mutations, insertions, and deletions can be produced in a given primer by methods known to an ordinarily skilled artisan.

Modification of genes and toxins. The genes and toxins useful according to the subject invention include not only the specifically exemplified full-length sequences, but also portions, segments and/or fragments (including internal and/or terminal deletions compared to the full-length molecules) of these sequences, variants, mutants, chimerics, and fusions thereof. Proteins of the subject invention can have substituted amino acids so long as they retain the characteristic pesticidal/functional activity of the proteins specifically exemplified herein. "Variant" genes have nucleotide sequences that encode the same toxins or equivalent toxins having pesticidal activity equivalent to an exemplified protein. The terms "variant proteins" and "equivalent toxins" refer to toxins having the same or essentially the same biological/functional activity against the target pests and equivalent sequences as the exemplified toxins. As used herein, reference to an "equivalent" sequence refers to sequences having amino acid substitutions, deletions, additions, or insertions which improve or do not adversely affect pesticidal activity. Fragments retaining pesticidal activity are also included in this definition. Fragments and other equivalents that retain the same or similar function, or "toxin activity," as a corresponding fragment of an exemplified toxin are within the scope of the subject invention. Changes, such as amino acid substitutions or additions, can be made for a variety of purposes, such as increasing (or decreasing) protease stability of the protein (without materially/substantially decreasing the functional activity of the toxin).

Equivalent toxins and/or genes encoding these equivalent toxins can be obtained/derived from wild-type or recombinant bacteria and/or from other wild-type or recombinant organisms using the teachings provided herein. Other *Bacillus, Paenibacillus, Photorhabdus*, and *Xenorhabdus* species, for example, can be used as source isolates.

Variations of genes may be readily constructed using standard techniques for making point mutations, for example. In addition, U.S. Pat. No. 5,605,793, for example, describes methods for generating additional molecular diversity by using DNA reassembly after random fragmentation. Variant genes can be used to produce variant proteins; recombinant hosts can be used to produce the variant proteins. Using these "gene shuffling" techniques, equivalent genes and proteins can be constructed that comprise any 5, 10, or 20 contiguous residues (amino acid or nucleotide) of any sequence exemplified herein. As one skilled in the art knows, the gene shuffling techniques can be adjusted to obtain equivalents having, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 contiguous residues (amino acid or nucleotide), corresponding to a segment (of the same size) in any of the exemplified sequences (or the complements (full complements) thereof). Similarly sized segments, especially those for conserved regions, can also be used as probes and/or primers.

Fragments of full-length genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

It is within the scope of the invention as disclosed herein that toxins may be truncated and still retain functional activity. By "truncated toxin" is meant that a portion of a toxin protein may be cleaved and yet still exhibit activity after cleavage. Cleavage can be achieved by proteases inside or outside of the insect gut. Furthermore, effectively cleaved proteins can be produced using molecular biology techniques wherein the DNA bases encoding said toxin are removed either through digestion with restriction endonucleases or other techniques available to the skilled artisan. After truncation, said proteins can be expressed in heterologous systems such as *E. coli*, baculoviruses, plant-based viral systems, yeast and the like and then placed in insect assays as disclosed herein to determine activity. It is well-known in the art that truncated toxins can be successfully produced so that they retain functional activity while having less than the entire, full-length sequence. It is well known in the art that B.t. toxins can be used in a truncated (core toxin) form. See, e.g., Adang et at, *Gene* 36:289-300 (1985), "Characterized full-length and truncated plasmid clones of the crystal protein of *Bacillus thuringiensis* subsp *kurstaki* HD-73 and their toxicity to *Manduca sexta*." There are other examples of truncated proteins that retain insecticidal activity, including the insect juvenile hormone esterase (U.S. Pat. No. 5,674,485 to the Regents of the University of California). As used herein, the term "toxin" is also meant to include functionally active truncations.

Certain toxins of the subject invention have been specifically exemplified herein. As these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid similarity (and/or homology) with an exemplified toxin. The amino acid identity will typically be greater than 60%, preferably greater than 75%, more preferably greater than 80%, even more preferably greater than 90%, and can be greater than 95%. Preferred polynucleotides and proteins of the subject invention can also be defined in terms of more particular identity and/or similarity ranges. For example, the identity and/or similarity can be 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein.

Unless otherwise specified, as used herein percent sequence identity and/or similarity of two nucleic acids is determined using the algorithm of Karlin and Altschul (1990), *Proc. Natl. Acad. Sci. USA* 87:2264-2268, modified as in Karlin and Altschul (1993), *Proc. Natl. Acad. Sci. USA* 90:5873-5877. Such an algorithm is incorporated into the NBLAST and XBLAST programs of Altschul et al. (1990), *J. Mol. Biol.* 215:402-410. BLAST nucleotide searches are performed with the NBLAST program, score=100, wordlength=12. Gapped BLAST can be used as described in Altschul et al. (1997), *Nucl. Acids Res.* 25:3389-3402. When utilizing BLAST and Gapped BLAST programs, the default parameters of the respective programs (NBLAST and XBLAST) are used. See NCBI/NIH website. The scores can also be calculated using the methods and algorithms of Crickmore et al. as described in the Background section, above. To obtain gapped alignments for comparison purposes, the AlignX function of Vector NTT Suite 8 (InforMax, Inc., North Bethesda, Md., U.S.A.), was used employing the default parameters. These were: a Gap opening penalty of 15, a Gap extension penalty of 6.66, and a Gap separation penalty range of 8.

The amino acid homology/similarity/identity will be highest in critical regions of the toxin which account for biological activity or are involved in the determination of three-dimensional configuration which is ultimately responsible for the biological activity. In this regard, certain amino acid substitutions are acceptable and can be expected to be tolerated. For example, these substitutions can be in regions of the protein that are not critical to activity. Analyzing the crystal structure of a protein, and software-based protein structure modeling, can be used to identify regions of a protein that can be modified (using site-directed mutagenesis, shuffling, etc.) to actually change the properties and/or increase the functionality of the protein.

Various properties and three-dimensional features of the protein can also be changed without adversely affecting the toxin activity/functionality of the protein. Conservative amino acid substitutions can be expected to be tolerated/to not adversely affect the three-dimensional configuration of the molecule. Amino acids can be placed in the following classes: non-polar, uncharged polar, basic, and acidic. Conservative substitutions whereby an amino acid of one class is replaced with another amino acid of the same type fall within the scope of the subject invention so long as the substitution is not adverse to the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the functional/biological activity of the toxin.

As used herein, reference to "isolated" polynucleotides and/or "purified" toxins refers to these molecules when they are not associated with the other molecules with which they would be found in nature. Thus, reference to "isolated" and/or "purified" signifies the involvement of the "hand of man" as described herein. For example, a bacterial toxin "gene" of the subject invention put into a plant for expression is an "isolated polynucleotide." Likewise, a *Xenorhabdus* protein, exemplified herein, produced by a plant is an "isolated protein."

Because of the degeneracy/redundancy of the genetic code, a variety of different DNA sequences can encode the amino acid sequences disclosed herein. It is well within the skill of a person trained in the art to create alternative DNA sequences that encode the same, or essentially the same, toxins. These variant DNA sequences are within the scope of the subject invention.

Optimization of sequence or expression in plants. To obtain high expression of heterologous genes in plants it may be preferred to reengineer said genes so that they are more efficiently expressed in (the cytoplasm of) plant cells. Maize is one such plant where it may be preferred to re-design the heterologous gene(s) prior to transformation to increase the expression level thereof in said plant. Therefore, an additional step in the design of genes encoding a bacterial toxin is reengineering of a heterologous gene for optimal expression.

One reason for the reengineering of a bacterial toxin for expression in maize is due to the non-optimal G+C content of the native gene. For example, the very low G+C content of many native bacterial gene(s) (and consequent skewing towards high A+T content) results in the generation of sequences mimicking or duplicating plant gene control sequences that are known to be highly A+T rich. The presence of some A+T-rich sequences within the DNA of gene(s) introduced into plants (e.g., TATA box regions normally found in gene promoters) may result in aberrant transcription of the gene(s). On the other hand, the presence of other regulatory sequences residing in the transcribed mRNA (e.g., polyadenylation signal sequences (AAUAAA), or sequences complementary to small nuclear RNAs involved in pre-mRNA splicing) may lead to RNA instability. Therefore, one goal in the design of genes encoding a bacterial toxin for maize expression, more preferably referred to as plant optimized gene(s), is to generate a DNA sequence having a higher C+C content, and preferably one close to that of maize genes coding for metabolic enzymes. Another goal in the design of the plant optimized gene(s) encoding a bacterial toxin is to generate a DNA sequence in which the sequence modifications do not hinder translation.

The table below (Table 2) illustrates how high the G+C content is in maize. For the data in Table 2, coding regions of the genes were extracted from GenBank (Release 71) entries, and base compositions were calculated using the MacVector™ program (IBI, New Haven, Conn.). Intron sequences were ignored in the calculations.

Due to the plasticity afforded by the redundancy/degeneracy of the genetic code (i.e., some amino acids are specified by more than one codon), evolution of the genomes in different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. It is thought that the presence of "minor" codons within a mRNA may reduce the absolute translation rate of that mRNA, especially when the relative abundance of the charged tRNA corresponding to the minor codon is low. An extension of this is that the diminution of translation rate by individual minor codons would be at least additive for multiple minor codons. Therefore, mRNAs having high relative contents of minor codons would have correspondingly low translation rates. This rate would be reflected by subsequent low levels of the encoded protein.

In engineering genes encoding a bacterial toxin for maize (or other plant, such as cotton or soybean) expression, the codon bias of the plant has been determined. The codon bias for maize is the statistical codon distribution that the plant uses for coding its proteins and the preferred codon usage is shown in Table 3. After determining the bias, the percent frequency of the codons in the gene(s) of interest is determined. The primary codons preferred by the plant should be determined as well as the second and third choice of preferred codons. Afterwards, the amino acid sequence of the bacterial toxin of interest is reverse translated so that the resulting nucleic acid sequence codes for exactly the same protein as the native gene wanting to be heterologously expressed. The new DNA sequence is designed using codon bias information so that it corresponds to the most preferred codons of the desired plant. The new sequence is then analyzed for restriction enzyme sites that might have been created by the modification. The identified sites are further modified by replacing the codons with second or third choice preferred codons. Other sites in the sequence which could affect transcription or translation of the gene of interest are the exon:intron junctions (5' or 3'), poly A addition signals, or RNA polymerase termination signals. The sequence is further analyzed and modified to reduce the frequency of TA or CC doublets. In addition to the doublets, G or C sequence blocks that have more than about four residues that are the same can affect transcription of the sequence. Therefore, these blocks are also modified by replacing the codons of first or second choice, etc. with the next preferred codon of choice.

TABLE 2

Compilation of G + C contents of protein coding regions of maize genes

| Protein Class.sup.a | Range % G + C | Mean % G + C.sup.b |
|---|---|---|
| Metabolic Enzymes (76) | 44.4-75.3 | 59.0 (.+-.8.0) |
| Structural Proteins (18) | 48.6-70.5 | 63.6 (.+-.6.7) |
| Regulatory Proteins (5) | 57.2-68.8 | 62.0 (.+-.4.9) |
| Uncharacterized Proteins (9) | 41.5-70.3 | 64.3 (.+-.7.2) |
| All Proteins (108) | 44.4-75.3 | 60.8 (.+-.5.2) |

.sup.a Number of genes in class given in parentheses.
.sup.b Standard deviations given in parentheses.
.sup.c Combined groups mean ignored in mean calculation It is preferred that the plant optimized gene(s) encoding a bacterial toxin contain about 63% of first choice codons, between about 22% to about 37% second choice codons, and between about 15% to about 0% third choice codons, wherein the total percentage is 100%. Most preferred the plant optimized gene(s) contains about 63% of first choice codons, at least about 22% second choice codons, about 7.5% third choice codons, and about 7.5% fourth choice codons, wherein the total percentage is 100%. The preferred codon usage for engineering genes for maize expression are shown in Table 3. The method described above enables one skilled in the art to modify gene(s) that are foreign to a particular plant so that the genes are optimally expressed in plants. The method is further illustrated in PCT application WO 97/13402.

In order to design plant optimized genes encoding a bacterial toxin, the amino acid sequence of said protein is reverse translated into a DNA sequence utilizing a non-redundant genetic code established from a codon bias table compiled for the gene sequences for the particular plant, as shown in Table 2. The resulting DNA sequence, which is completely homogeneous in codon usage, is further modified to establish a DNA sequence that, besides having a higher degree of codon diversity, also contains strategically placed restriction enzyme recognition sites, desirable base composition, and a lack of sequences that might interfere with transcription of the gene, or translation of the product mRNA.

TABLE 3

Preferred amino acid codons for proteins expressed in maize

| Amino Acid | Codon* |
|---|---|
| Alanine | GCC/GCG |
| Cysteine | TGC/TGT |
| Aspartic Acid | GAC/GAT |
| Glutamic Acid | GAG/GAA |
| Phenylalanine | TTC/TTT |
| Glycine | GGC/GGG |
| Histidine | CAC/CAT |
| Isoleucine | ATC/ATT |
| Lysine | AAG/AAA |
| Leucine | CTG/CTC |
| Methionine | ATG |
| Asparagine | AAC/AAT |
| Proline | CCG/CCA |
| Glutamine | CAG/CAA |
| Arginine | AGG/CGC |
| Serine | AGC/TCC |
| Threonine | ACC/ACG |
| Valine | GTG/GTC |
| Tryptophan | TGG |
| Tryrosine | TAC/TAT |
| Stop | TGA/TAG |

*The first and second preferred codons for maize.

Thus, synthetic genes that are functionally equivalent to the toxins/genes of the subject invention can be used to transform hosts, including plants. Additional guidance regarding the production of synthetic genes can be found in, for example, U.S. Pat. No. 5,380,831.

In some cases, especially for expression in plants, it can be advantageous to use truncated genes that express truncated proteins. Höfte et al. 1989, for example, discussed in the Background Section above, discussed protoxin and core toxin segments of B.t. toxins. Preferred truncated genes will typically encode 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the full-length toxin.

Transgenic hosts. The toxin-encoding genes of the subject invention can be introduced into a wide variety of microbial or plant hosts. In preferred embodiments, transgenic plant cells and plants are used. Preferred plants (and plant cells) are corn, maize, and cotton.

In preferred embodiments, expression of the toxin gene results, directly or indirectly, in the intracellular production (and maintenance) of the pesticide proteins. Plants can be rendered insect-resistant in this manner. When transgenic/recombinant/transformed/transfected host cells (or contents thereof) are ingested by the pests, the pests will ingest the toxin. This is the preferred manner in which to cause contact of the pest with the toxin. The result is control (killing or making sick) of the pest. Sucking pests can also be controlled in a similar manner. Alternatively, suitable microbial hosts, e.g., *Pseudomonas* such as *P. fluoresens*, can be applied where target pests are present; the microbes can proliferate there, and are ingested by the target pests. The microbe hosting the toxin gene can be treated under conditions that prolong the activity of the toxin and stabilize the cell. The treated cell, which retains the toxic activity, can then be applied to the environment of the target pest.

Where the toxin gene is introduced via a suitable vector into a microbial host, and said host is applied to the environment in a living state, certain host microbes should be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthononas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Also of interest are pigmented microorganisms.

Insertion of genes to form transpenic hosts. One aspect of the subject invention is the transformation/transfection of plants, plant cells, and other host cells with polynucleotides of the subject invention that express proteins of the subject invention. Plants transformed in this manner can be rendered resistant to attack by the target pest(s).

A wide variety of methods are available for introducing a gene encoding a pesticidal protein into the target host under conditions that allow for stable maintenance and expression of the gene. These methods are well known to those skilled in the art and are described, for example, in U.S. Pat. No. 5,135,867.

For example, a large number of cloning vectors comprising a replication system in *E. coli* and a marker that permits selection of the transformed cells are available for preparation for the insertion of foreign genes into higher plants. The vectors comprise, for example, pBR322, pUC series, M13 mp series, pACYC184, etc. Accordingly, the sequence encoding the toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1-46; and An et al. (1985) *EMBO J.* 4:277-287.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the right and left T-DNA border regions. They can be transformed directly into *Agrobacteria* (Holsters et al. [1978] *Mol. Gen. Genet.* 163: 181-187). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In some preferred embodiments of the invention, genes encoding the bacterial toxin are expressed from transcriptional units inserted into the plant genome. Preferably, said transcriptional units are recombinant vectors capable of stable integration into the plant genome and enable selection of transformed plant lines expressing mRNA encoding the proteins.

Once the inserted DNA has been integrated in the genome, it is relatively stable there (and does not come out again). It normally contains a selection marker that confers on the transformed plant cells resistance to a biocide or an antibiotic, such as kanamycin, G418, bleomycin, hygromycin, or chloramphenicol, inter alia. The individually employed marker should accordingly permit the selection of transformed cells rather than cells that do not contain the inserted DNA. The gene(s) of interest are preferably expressed either by constitutive or inducible promoters in the plant cell. Once expressed, the mRNA is translated into proteins, thereby incorporating amino acids of interest into protein. The genes encoding a toxin expressed in the plant cells can be under the control of a constitutive promoter, a tissue-specific promoter, or an inducible promoter.

Several techniques exist for introducing foreign recombinant vectors into plant cells, and for obtaining plants that stably maintain and express the introduced gene. Such techniques include the introduction of genetic material coated onto microparticles directly into cells (U.S. Pat. No. 4,945,050 to Cornell and U.S. Pat. No. 5,141,131 to DowElanco, now Dow AgroSciences, LLC). In addition, plants may be transformed using *Agrobacterium* technology, see U.S. Pat. No. 5,177,010 to University of Toledo; U.S. Pat. No. 5,104,310 to Texas A&M; European Patent Application 0131624B1; European Patent Applications 120516, 159418B1 and 176,112 to Schilperoot; U.S. Pat. Nos. 5,149,645, 5,469,976, 5,464,763 and 4,940,838 and 4,693,976 to Schilperoot; European Patent Applications 116718, 290799, 320500 all to Max Planck; European Patent Applications 604662 and 627752, and U.S. Pat. No. 5,591,616, to Japan Tobacco; European Patent Applications 0267159 and 0292435, and U.S. Pat. No. 5,231,019, all to Ciba Geigy, now Novartis; U.S. Pat. Nos. 5,463,174 and 4,762,785, both to Calgene; and U.S. Pat. Nos. 5,004,863 and 5,159,135, both to Agracetus. Other transformation technology includes whiskers technology. See U.S. Pat. Nos. 5,302,523 and 5,464,765, both to Zeneca. Electroporation technology has also been used to transform plants. See WO 87/06614 to Boyce Thompson Institute; U.S. Pat. Nos. 5,472,869 and 5,384,253, both to Dekalb; and WO 92/09696 and WO 93/21335, both to Plant Genetic Systems. Furthermore, viral vectors can also be used to produce transgenic plants expressing the protein of interest. For example, monocotyledonous plant can be transformed with a viral vector using the methods described in U.S. Pat. No. 5,569,597 to Mycogen Plant Science and Ciba-Giegy, now Novartis, as well as U.S. Pat. Nos. 5,589,367 and 5,316,931, both to Biosource.

As mentioned previously, the manner in which the DNA construct is introduced into the plant host is not critical to this invention. Any method which provides for efficient transformation may be employed. For example, various methods for plant cell transformation are described herein and include the use of Ti or Ri-plasmids and the like to perform *Agrobacterium* mediated transformation. In many instances, it will be desirable to have the construct used for transformation bordered on one or both sides by T-DNA borders, more specifically the right border. This is particularly useful when the construct uses *Agrobacterium tumefaciens* or *Agrobacterium rhizogenes* as a mode for transformation, although T-DNA borders may find use with other modes of transformation. Where *Agrobacterium* is used for plant cell transformation, a vector may be used which may be introduced into the host for homologous recombination with T-DNA or the Ti or Ri plasmid present in the host. Introduction of the vector may be performed via electroporation, tri-parental mating and other techniques for transforming gram-negative bacteria which are known to those skilled in the art. The manner of vector transformation into the *Agrobacterium* host is not critical to this invention. The Ti or Ri plasmid containing the T-DNA for recombination may be capable or incapable of causing gall formation, and is not critical to said invention so long as the vir genes are present in said host.

In some cases where *Agrobacterium* is used for transformation, the expression construct being within the T-DNA borders will be inserted into a broad spectrum vector such as pRK2 or derivatives thereof as described in Ditta et al., (PNAS USA (1980) 77:7347-7351 and EPO 0 120 515, which are incorporated herein by reference. Included within the expression construct and the T-DNA will be one or more markers as described herein which allow for selection of transformed *Agrobacterium* and transformed plant cells. The particular marker employed is not essential to this invention, with the preferred marker depending on the host and construction used.

For transformation of plant cells using *Agrobacterium*, explants may be combined and incubated with the transformed *Agrobacterium* for sufficient time to allow transformation thereof. After transformation, the *Agrobacteria* are killed by selection with the appropriate antibiotic and plant cells are cultured with the appropriate selective medium. Once calli are formed, shoot formation can be encouraged by employing the appropriate plant hormones according to methods well known in the art of plant tissue culturing and plant regeneration. However, a callus intermediate stage is not always necessary. After shoot formation, said plant cells can be transferred to medium which encourages root formation thereby completing plant regeneration. The plants may then be grown to seed and said seed can be used to establish future generations. Regardless of transformation technique, the gene encoding a bacterial toxin is preferably incorporated into a gene transfer vector adapted to express said gene in a plant cell by including in the vector a plant promoter regulatory element, as well as 3' non-translated transcriptional termination regions such as Nos and the like.

In addition to numerous technologies for transforming plants, the type of tissue which is contacted with the foreign genes may vary as well. Such tissue would include but would not be limited to embryogenic tissue, callus tissue types I, II, and III, hypocotyl, meristem, root tissue, tissues for expression in phloem, and the like. Almost all plant tissues may be transformed during dedifferentiation using appropriate techniques described herein.

As mentioned above, a variety of selectable markers can be used, if desired. Preference for a particular marker is at the discretion of the artisan, but any of the following selectable markers may be used along with any other gene not listed herein which could function as a selectable marker. Such selectable markers include but are not limited to aminoglycoside phosphotransferase gene of transposon Tn5 (Aph II) which encodes resistance to the antibiotics kanamycin, neomycin and G418, as well as those genes which encode for resistance or tolerance to glyphosate; hygromycin; methotrexate; phosphinothricin (bialaphos); imidazolinones, sulfonylureas and triazolopyrimidine herbicides, such as chlorsulfuron; bromoxynil, dalapon and the like.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988). Preferred reporter genes include the beta-glucuronidase (GUS) of the uidA locus of *E. coli*, the chloramphenicol acetyl transferase gene from Tn9 of *E. coli*, the green fluorescent protein from the bioluminescent jellyfish *Aequorea victoria*, and the luciferase genes from firefly *Photinus pyralis*. An assay for detecting reporter gene expression may then be performed at a suitable time after said gene has been introduced into recipient cells. A preferred such assay entails the use of the gene encoding beta-glucuronidase (GUS) of the uidA locus of *E. coli* as described by Jefferson et al., (1987 Biochem. Soc. Trans. 15, 17-19) to identify transformed cells.

In addition to plant promoter regulatory elements, promoter regulatory elements from a variety of sources can be used efficiently in plant cells to express foreign genes. For example, promoter regulatory elements of bacterial origin, such as the octopine synthase promoter, the nopaline synthase promoter, the mannopine synthase promoter; promoters of viral origin, such as the cauliflower mosaic virus (35S and 19S), 35T (which is a re-engineered 35S promoter, see U.S. Pat. No. 6,166,302, especially Example 7E) and the like may be used. Plant promoter regulatory elements include but are not limited to ribulose-1,6-bisphosphate (RUBP) carboxylase small subunit (ssu), beta-conglycinin promoter, beta-phaseolin promoter, ADH promoter, heat-shock promoters, and tissue specific promoters. Other elements such as matrix attachment regions, scaffold attachment regions, introns, enhancers, polyadenylation sequences and the like may be present and thus may improve the transcription efficiency or DNA integration. Such elements may or may not be necessary for DNA function, although they can provide better expression or functioning of the DNA by affecting transcription, mRNA stability, and the like. Such elements may be included in the DNA as desired to obtain optimal performance of the transformed DNA in the plant. Typical elements include but are not limited to Adh-intron 1, Adh-intron 6, the alfalfa mosaic virus coat protein leader sequence, the maize streak virus coat protein leader sequence, as well as others available to a skilled artisan. Constitutive promoter regulatory elements may also be used thereby directing continuous gene expression in all cells types and at all times (e.g., actin, ubiquitin, CaMV 35S, and the like). Tissue specific promoter regulatory elements are responsible for gene expression in specific cell or tissue types, such as the leaves or seeds (e.g., zein, oleosin, napin, ACP, globulin and the like) and these may also be used.

Promoter regulatory elements may also be active during a certain stage of the plant's development as well as active in plant tissues and organs. Examples of such include but are not limited to pollen-specific, embryo-specific, corn-silk-specific, cotton-fiber-specific, root-specific, seed-endosperm-specific promoter regulatory elements and the like. Under certain circumstances it may be desirable to use an inducible promoter regulatory element, which is responsible for expression of genes in response to a specific signal, such as: physical stimulus (heat shock genes), light (RUBP carboxylase), hormone (Em), metabolites, chemical, and stress. Other desirable transcription and translation elements that function in plants may be used. Numerous plant-specific gene transfer vectors are known in the art.

Standard molecular biology techniques may be used to clone and sequence the toxins described herein. Additional information may be found in Sambrook, J., Fritsch, E. F., and Maniatis, T. (1989), Molecular Cloning, A Laboratory Manual, Cold Spring Harbor Press, which is incorporated herein by reference.

Resistance Management. With increasing commercial use of insecticidal proteins in transgenic plants, one consideration is resistance management. That is, there are numerous companies using *Bacillus thuringiensis* toxins in their products, and there is concern about insects developing resistance to B.t. toxins. One strategy for insect resistance management would be to combine the TC toxins produced by *Xenorhabdus, Photorhabdus*, and the like with toxins such as B.t. crystal toxins, soluble insecticidal proteins from *Bacillus* stains (see, eg., WO 98/18932 and WO 99/57282), or other insect toxins. The combinations could be formulated for a sprayable application or could be molecular combinations. Plants could be transformed with bacterial genes that produce two or more different insect toxins (see, e.g., Gould, 38 *Bioscience* 26-33 (1988) and U.S. Pat. No. 5,500,365; likewise, European Patent Application 0 400 246 A1 and U.S. Pat. Nos. 5,866,784; 5,908,970; and 6,172,281 also describe transformation of a plant with two B.t. crystal toxins). Another method of producing a transgenic plant that contains more than one insect resistant gene would be to first produce two plants, with each plant containing an insect resistance gene. These plants could then be crossed using traditional plant breeding techniques to produce a plant containing more than one insect resistance gene. Thus, it should be apparent that the phrase "comprising a polynucleotide" as used herein means at least one polynucleotide (and possibly more, contiguous or not) unless specifically indicated otherwise.

Formulations and Other Delivery Systems. Formulated bait granules containing spores and/or crystals of the subject isolate, or recombinant microbes comprising the genes obtainable from the isolate disclosed herein, can be applied to the soil. Formulated product can also be applied as a seed-coating or root treatment or total plant treatment at later stages of the crop cycle. Plant and soil treatments of cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Another delivery scheme is the incorporation of the genetic material of toxins into a baculovirus vector. Baculoviruses infect particular insect hosts, including those desirably targeted with the toxins. Infectious baculovirus harboring an expression construct for the toxins could be introduced into areas of insect infestation to thereby intoxicate or poison infected insects.

Insect viruses, or baculoviruses, are known to infect and adversely affect certain insects. The affect of the viruses on insects is slow, and viruses do not immediately stop the feeding of insects. Thus, viruses are not viewed as being optimal as insect pest control agents. However, combining the toxin genes into a baculovirus vector could provide an efficient way of transmitting the toxins. In addition, since different baculoviruses are specific to different insects, it may be possible to use a particular toxin to selectively target particularly damaging insect pests. A particularly useful vector for the toxins genes is the nuclear polyhedrosis virus. Transfer vectors using this virus have been described and are now the vectors of choice for transferring foreign genes into insects. The virus-toxin gene recombinant may be constructed in an orally transmissible form. Baculoviruses normally infect insect victims through the mid-gut intestinal mucosa. The toxin gene inserted behind a strong viral coat protein promoter would be expressed and should rapidly kill the infected insect.

In addition to an insect virus or baculovirus or transgenic plant delivery system for the protein toxins of the present invention, the proteins may be encapsulated using *Bacillus thuringiensis* encapsulation technology such as but not limited to U.S. Pat. Nos. 4,695,455; 4,695,462; 4,861,595 which are all incorporated herein by reference. Another delivery system for the protein toxins of the present invention is formulation of the protein into a bait matrix, which could then be used in above and below ground insect bait stations. Examples of such technology include but are not limited to PCT Patent Application WO 93/23998, which is incorporated herein by reference.

Plant RNA viral based systems can also be used to express bacterial toxin. In so doing, the gene encoding a toxin can be inserted into the coat promoter region of a suitable plant virus which will infect the host plant of interest. The toxin can then be expressed thus providing protection of the plant from insect damage. Plant RNA viral based systems are described in U.S. Pat. No. 5,500,360 to Mycogen Plant Sciences, Inc. and U.S. Pat. Nos. 5,316,931 and 5,589,367 to Biosource Genetics Corp.

In addition to producing a transformed plant, there are other delivery systems where it may be desirable to reengineer the bacterial gene(s). For example, a protein toxin can be constructed by fusing together a molecule attractive to insects as a food source with a toxin. After purification in the laboratory such a toxic agent with "built-in" bait could be packaged inside standard insect trap housings.

Mutants. Mutants of the *Xenorhabdus bovienii* isolate of the invention can be made by procedures that are well known in the art. For example, asporogenous mutants can be obtained through ethylmethane sulfonate (EMS) mutagenesis of an isolate. The mutants can be made using ultraviolet light and nitrosoguanidine by procedures well known in the art.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Overview

The identification and isolation of genes encoding factors that potentiate or synergize the activity of the insect active proteins *Photorhabdus* TcdA and *Xenorhabdus* XptA2$_{wi}$ were accomplished using a cosmid complementation screen. Individual *Escherichia coli* clones from a cosmid genomic library of *Xenorhabdus bovienii* (strain ILM104) were used to create crude cell extracts which were mixed with purified toxins and bioassayed. Lysates were assayed with purified *Photorhabdus* toxin TcdA against southern corn rootworm larvae (*Diabrotica undecimpunctata* howardi). Likewise, lysates were also mixed with purified *Xenorhabdus* XptA2$_{wi}$ protein and assayed against tobacco budworm (*Heliothis virescens*) or corn earworm (*Helicoverpa zea*) larvae. Cosmid lysates were scored as positive if the combination of lysate plus purified toxin had activity greater than either component alone.

The primary screen samples (in 96-well format) were tested in duplicate and scored compared to controls for insecticidal activity. Positive samples were re-grown and tested in the secondary screen. Cosmids identified as positive through primary and secondary screens were screened a third time. Larger culture volumes were utilized for tertiary screens (see below), tested for biological activity in a 128-well format bioassay.

DNA from one of the cosmids identified as having potentiating activity in this screen was subcloned. The DNA sequence of a single subclone which retained activity was determined and shown to contain two open reading frames, designated xptB1$_{xb}$ and xptC1$_{xb}$. These coding regions were subcloned into pET plasmids and expressed in *E. coli*. A dramatic increase in insect activity was seen when either TcdA or XptA2$_{wi}$ protein was mixed with lysates co-expressing both XptB1$_{xb}$ and XPtC1$_{xb}$. Lysates containing only XptB1$_{xb}$ or only XPtC1$_{xb}$ had minimal affects when mixed with purified TcdA or XptA2$_{wi}$.

Example 2

Insect Bioassay Methodology

Insect bioassays were conducted using artificial diets in either 96-well microtiter plates (Becton Dickinson and Company, Franklin Lakes, N.J.) or 128-well trays specifically designed for insect bioassays (C-D International, Pitman, N.J.). Eggs from 2 lepidopteran species were used for bioassays conducted in 96-well microtiter plates: the corn earworm, (*Helicoverpa zea* (Boddie)), and the tobacco budworm, (*Heliothis virescens* (F.)). Neonate larvae were used for bioassays conducted in 128-well trays. The lepidopteran species tested in this format included the corn earworm, the tobacco budworm, and the beet armyworm, (*Spodoptera exigua* (Hübner)). A single coleopteran species, the southern corn rootworm, (*Diabrotica undecimpunctata howardii* (Barber)), was also tested in this bioassay format.

The data recorded in these bioassays included the total number of insects in the treatment, number of dead insects, the number of insects whose growth was stunted, and the weight of surviving insects. In cases where growth inhibition is reported, this was calculated as follows:

% Growth Inhibition=[1−(Average Weight of Insects in Treatment/Average Weight of Insects in the Vector-Only Control)]*100

Example 3

Cosmid Library Construction

*Xenorhabdus* strain ILM104, previously determined to represent the species *X. bovienii* by 16S RNA sequence determination (Midi Labs, Newark, Del.), was grown on 2% proteose peptone #3 (hereafter designated as PP3) agar containing 0.0025% brom thymol blue for 72 hours at 28° C. A single, brom thymol blue-adsorbing colony was selected and used to inoculate 500-mL tri-baffled flasks containing 175 mL of PP3. Shake flasks were shaken at 150 rpm and incubated at 28° C. for approximately 24 hrs. Fifty mL of this culture was centrifuged at 2,400×g to pellet the cells. The supernatant fluid was removed and the cell pellet was frozen at −20° C. until it was thawed for total cellular DNA isolation.

Total cellular DNA was isolated using a Genomic DNA purification kit (Qiagen Inc., Valencia, Calif.). The frozen bacterial cell pellet was resuspended by vortexing in 11 mL of Buffer B1 (50 mM Tris/HCl, pH 8.0; 50 mM EDTA, pH 8.0; 0.5% Tween 20, 0.5% Triton X-100) containing 11 µL of Qiagen RNase A solution (100 mg/mL). To this suspension were added 300 µL of lysozyme stock solution (100 mg/mL; Sigma Chemical Co., St. Louis, Mo.) and 500 µL of proteinase K stock solution (50 mg/mL; Sigma Chemical Co.). The suspension was mixed by vortexing and incubated at 37° C. for 30 min. Four mL of Buffer B2 (3 M guanidine HCl; 20% Tween 20) was added to the bacterial lysate and mixed into solution by gentle inversion of the tubes. The bacterial lysates were incubated at 50° C. for 30 min, and then total cellular DNA was isolated from the bacterial lysate using Qiagen Genomic-tip 500/G tips as per the manufacturer's instructions (Qiagen Genomic DNA Handbook). The resulting purified DNA was dissolved in 500 µL TE buffer (10 mM Tris/HC pH 8.0; 1 mM EDTA pH 8.0) and stored at 4° C.

Partial Sau3A I digests were made of the total cellular DNA using a protocol based on section 3.1.3 of Ausubel, et al. (Current Protocols in Molecular Biology, John Wiley and Sons, Inc. New York, N.Y.). Small-scale reactions (40 µg of total cellular DNA in an 80 µL reaction volume) were performed to determine the proper ratio of enzyme to total cellular DNA that resulted in the maximal concentration of partially-digested DNA fragments in the size range of 25-50 Kb (kilobase pairs). Reactions were heated at 65° C. for 15 min to inactivate the Sau3A I enzyme and aliquots of the reactions were electrophoresed through 0.3% agarose gels to determine the relative abundance of partially-digested DNA fragments in the desired size range. Once an optimal enzyme to total cellular DNA ratio was observed, the reaction volume was scaled up to obtain sufficient quantities of partially-digested total cellular DNA for use as insert DNA in the construction of cosmid libraries. A typical scaled up reaction contained 400 µg of *Xenorhabdus bovienii* total cellular DNA incubated with 9 units of Sau3A I (Gibco BRL, Gaithersburg, Md.) for 15 min at 37° C. in 800 µL total volume of 1× React 4 Buffer (supplied as 10× by Gibco BRL). The reaction was heated at 65° C. for 20 min to inactivate the enzyme. To minimize the ligation of insert DNA to other insert DNA fragments during the cosmid library construction process, the partially-digested *Xenorhabdus* total cellular DNA was dephosphorylated by incubating with 20 units of shrimp alkaline phosphatase (Boehringer Mannheim, Mannheim, Germany) for 2 hrs at 37° C. in 1.2 mL total volume of 1×SAP buffer (supplied as 10× by the manufacturer). The dephosphorylated insert DNA was mixed with an equal volume of a buffer-equilibrated phenol-chloroform solution (50:50; v/v) and mixed by gentle inversion. After centrifugation at 14,000×g for 15 min, the aqueous phase was removed and mixed by gentle inversion with an equal volume of a chloroform-isoamyl alcohol solution (24:1; v/v). The phases were again separated by centrifugation at 14,000×g for 15 min. The aqueous phase was removed to a fresh tube and 0.1 volume of 3 M sodium acetate (pH 5.2) was added. Two volumes of ice-cold 100% ethanol were added and the solution was mixed by gentle inversion and placed at −70° C. overnight. The precipitated DNA was pelleted by centrifugation at 14,000×g for 20 min, and the DNA pellet was resuspended in 50 μL of double-distilled water and stored at −20° C.

The SuperCos 1 vector (Stratagene, La Jolla, Calif.), prepared as recommended by the manufacturer, was used for construction of the cosmid library. Insert DNA was ligated into the BamH I site of SuperCos I DNA using a 3:1 ratio of partially-digested insert to vector DNA and incubation overnight at 16° C. with 20 units of T4 DNA Ligase (New England BioLabs Inc., Beverly, Mass.) in 1× T4 DNA Ligase Buffer (supplied as 10× by the manufacturer). Ligation mixtures were packaged using Gigapack III Gold Packaging Extract (Stratagene) and recombinant phage were titered using $E.$ $coli$ strain XL1-Blue MR cells as recommended by the manufacturer. Aliquots (20-40 μL) of the recombinant phage and host cell cultures were spread onto LB agar (10 g/L Bacto-tryptone, 10 g/L NaCl, 5 g/L Bacto-yeast extract, 15 g/L Bacto agar; Difco Laboratories) containing ampicillin (100 mg/L; Sigma Chemical Co.) and incubated overnight at 37° C. To construct master plates of the cosmid libraries for long term storage, single colonies were picked with sterile wooden toothpicks and inoculated into individual wells of sterile 96-well plates containing 100-1000 μL of Terrific Broth (TB media: 12 g/L Bacto-tryptone, 24 g/L Bacto-yeast extract, 0.4% v/v glycerol, 17 mM $KH_2PO_4$, 72 mM $K_2HPO_4$) plus either 100 mg/L ampicillin or 50 mg/L kanamycin (Sigma Chemical Co.) and incubated without shaking overnight at 37° C. To generate copy plates from the master plates, a 96-well microplate replicator (V & P Scientific, Inc., San Diego, Calif.) was used to inoculate a sterile 96-well microwell plate containing 100-1000 μL of LB broth containing 100 mg/L ampicillin. Copy plates were incubated without shaking at 37° C. overnight. For both master and copy plates, an equal volume (100-1000 μL of filter-sterilized TB:glycerol or LB:glycerol was added to the plates and the cultures and glycerol solutions were mixed using a multichannel pipet. Plates were sealed with Biomek Seal and Sample aluminum foil lids (Beckman Instruments, Inc., Fullerton, Calif.) and placed at −70° C. for storage.

The average insert size of selected recombinant cosmids was assessed by isolating cosmid DNA using the NucleoSpin Nucleic Acid Purification Kit (CLONTECH Laboratories, Inc., Palo Alto, Calif.) and digestion of the recovered DNA with 20 units of the restriction enzyme EcoR I (New England BioLabs) for 1 hr at 37° C. Restricted DNA was electrophoresed through a 1.0% agarose gel. DNA fragments were visualized with UV light following 0.5% ethidium bromide staining (Sigma Chemical Co.), and relative sizes of fragments were estimated by comparison with 1 Kb DNA ladder (Gibco BRL). Average insert size of the cosmid libraries constructed ranged from 30 Kb-45 Kb.

Example 4

Complementation Screen

Culture Growth Conditions

For the primary and secondary complementation screens, individual $E.$ $coli$ colonies of the cosmid libraries were cultured (in duplicate) in 2 mL TB medium containing 100 μg/mL ampicillin at 28° C. for 48 hrs in deep 96-well plates. For the tertiary complementation screen, cosmid-containing $E.$ $coli$ was grown in 100 mL of TB medium containing 50 μg/mL kanamycin, 100 mM glucose, at 28° C. for 24-48 hours, with shaking at 200-250 rpm.

Example 5

Complementation Screen: Lysate Preparation

For the primary and secondary screens, duplicate 2 mL deep-well plates containing the library cells were centrifuged at 4000 rpm (2250×g) for 5 min in an Eppendorf 5810R centrifuge. The duplicate pellets were resuspended and combined into a total of 250 μL of LB. The suspension was added to 1.2 mL Costar tubes (Fisher Scientific) containing 3-4 mm of 0.1 mm diameter glass beads. The tubes were then shaken in a Kleco™ 4-96 Pulverizer bead mill (Garcia Manufacturing, Visalia, Calif.) for 3 min at maximum speed. The samples were centrifuged at 2500 rpm for 3 min in the Eppendorf 5810R centrifuge, and 200 μL of the resulting supernatant was added to a fresh 96-well plate. To this $E.$ $coli$ cell lysate, 50 μL of the appropriate purified toxin, (either TcdA or XptA2$_{wi}$), or 10 mm phosphate buffer (as negative control) was added prior to the insect bioassay.

Lysates for the tertiary screen were prepared from 100 mL cultures by centrifugation at 3000×g in 50 mL conical tubes. The pellets were resuspended in LB media to approximately 40 $OD_{600}$ units/mL (Shimadzu UV160U spectrophotometer (Kyoto, JP). The cells were then distributed into 96-well 1.2 mL Costar tubes containing 3-4 mm of 0.1 mm diameter glass beads, shaken in the Kleco™ 4-96 Pulverizer for 3 minutes at maximum speed, then centrifuged at 2500 rpm for 3 minutes in the Eppendorf 5810R centrifuge. The supernatants of each sample were pooled into one tube and purified toxin was added. Either TcdA (final concentration of 50 ng/cm$^2$) or XptA2$_{wi}$ (final concentration of 250 ng/cm$^2$), or 10 mm-phosphate buffer were added prior to insect bioassay.

Example 6

Complementation Screen: Subcloning of Active Cosmid Fragments

The activity screen described above was successful in identifying cosmids which produced extracts that increased the activity of TcdA and $XptA2_{wi}$. One cosmid (designated 5H4) was chosen for further study. DNA was isolated from cells containing the 5H4 cosmid using the Wizards Plus Midipreps DNA Purification System from Promega (Madison, Wis.) according to the manufacturer's instructions. The DNA was characterized using restriction endonucleases from Roche Applied Science (Indianapolis, Ind.) according to manufacturer's instructions. The digests were electrophoresed through 0.7% agarose gels and visualized with ethidium bromide using standard molecular biology techniques. A Bgl II fragment of approximately 12 Kb was subcloned from the *Xenorhabdus* ILM104 cosmid 5H4 by ligation into the BamHI site of vector pBCKS+(Stratagene), using standard molecular biology techniques (Sambrook and Russell, Molecular Cloning: A Laboratory Manual Third Edition, Cold Spring Harbor Laboratory Press, 2001). The ligation was transformed into *E. coli* DH5α subcloning efficiency cells (Stratagene) according to the supplier's instructions. The resulting plasmid was called pDAB6026.

Plasmid pDAB6026 was shown to encode activities which synergized the insect toxic activities of TcdA and XptA2$_{wi}$. *E. coli* cells containing plasmid pDAB6026 or the pBCKS+ vector control were inoculated into 200 mL of LB containing chloramphenicol (50 μg/mL) and 75 μM IPTG (isopropyl-β-D-thiogalactopyranoside) and grown for two days at 28° C. with shaking at 180 rpm. The cells were then centrifuged for 10 min at 3500×g. The pellets were resuspended in 5 mL of Butterfield's phosphate solution (Fisher Scientific) and transferred to 50 mL conical tubes containing 1.5 mL of 0.1 mm diameter glass beads (Biospec, Bartlesville, Okla., catalog number 1107901). The cell-glass bead mixture was chilled on ice, then the cells were lysed by sonication with two 45 second bursts using a 2 mm probe with a Branson Sonifier 250 (Danbury Conn.) at an output of 20, chilling completely between bursts. The supernatant was transferred to 2 mL microcentrifuge tubes and centrifuged for 5 min at 16,000×g. The supernatants were then transferred to 15 mL tubes, and the protein concentration was measured. Bio-Rad Protein Dye Assay Reagent was diluted 1:5 with $H_2O$ and 1 mL was added to 10 μL of a 1:10 dilution of each sample and to bovine serum albumin (BSA) at concentrations of 5, 10, 15, 20 and 25 μg/mL. The samples were then read on a spectrophotometer measuring the optical density at the wavelength of 595 in the Shimadzu UV160U spectrophotometer (Kyoto, JP). The amount of protein contained in each sample was then calculated against the BSA standard curve and adjusted to between 3-6 mg/mL with phosphate buffer. Six hundred nanograms of XptA2$_{wi}$ toxin protein were added to 500 μL of the *E. coli* lysate prior to testing in insect feeding bioassays. The combination of pDAB6026 and XptA2 was shown to have potent activity (Table 4).

TABLE 4

Response of 2 lepidopteran species to pDAB6026 lysates alone and with purified XptA2$_{wi}$ protein.

| Treatment | tobacco budworm Dead | Stunted | Total | Weight | corn earworm Dead | Stunted | Total | Weight |
|---|---|---|---|---|---|---|---|---|
| 1 pBC | 0 | 0 | 8 | 674 | 0 | 0 | 8 | 352 |
| 2 pBC + XptA2$_{wi}$ | 0 | 0 | 8 | 538 | 0 | 0 | 8 | 423 |
| 3 pDAB6026 | 0 | 0 | 8 | 539 | 0 | 0 | 8 | 519 |
| 4 pDAB6026 + XptA2$_{wi}$ | 0 | 8 | 8 | 18 | 8 | — | 8 | — |

Example 7

Discovery, Engineering and Testing of XptB1$_{xb}$ and xptC1$_{xb}$ Genes

DNA of plasmid pDAB6026 was sent to SeqWright DNA Sequencing (Houston, Tex.) for DNA sequence determination. Two complete open reading frames (ORFs) of substantial size were discovered. The first (disclosed as SEQ ID NO:1) has significant similarity to known toxin complex genes belonging to the "B" class. This ORF was therefore called xptB1$_{xb}$ and encodes the protein disclosed as SEQ ID NO:2. The second ORF (SEQ ID NO:3) encodes a protein (SEQ ID NO:4) with homology to toxin complex "C" proteins and therefore was named xptC1$_{xb}$. A partial open reading frame was also discovered (SEQ ID NO:5), and has significant homology to the "A" class of toxin complex genes. This partial ORF encodes the protein sequence of SEQ ID NO:6.

The two complete genes, xptB1$_{xb}$ and xptC1$_{xb}$ were engineered (using the polymerase chain reaction; PCR) for high level recombinant expression by addition of restriction sites 5' and 3' to the coding regions, as well as provision of ribosome binding sequences and optimal translational stop signals. In addition, silent mutations (no change in amino acid sequence) were introduced into the 5' end of the coding regions to reduce potential secondary structure of the mRNA and hence increase translation. The strategy was to amplify/engineer segments at the 5' and 3' ends of the genes, join the distal fragments using 'Splice Overlap Extensions' reactions, then add the non-amplified center portion of the open reading frames via restriction sites. This approach minimized the potential of PCR-induced changes in the DNA sequence. The engineered coding regions were cloned into pET expression plasmids (Novagen, Madison, Wis.) as either separate coding regions (SEQ ID NO:7 and SEQ ID NO:8) or a dicistronic operon (SEQ ID NO:9). The names of the expression plasmids are shown in Table 5.

TABLE 5

Expression plasmids containing various coding regions cloned into the pET vector.

| Plasmid Name | Coding Region Engineered for Expression |
|---|---|
| pDAB6031 | xptB1$_{xb}$ as in SEQ ID NO: 7 |
| pDAB6032 | xptC1$_{xb}$ as in SEQ ID NO: 8 |
| pDAB6033 | xptB1$_{xb}$ + xptC1$_{xb}$ as in SEQ ID NO: 9 |

Competent cells of the *E. coli* T7 expression strain BL21) (DE3) Star™ (Stratagene, La Jolla, Calif.) were freshly transformed with DNA of either the pET (control) vector or plasmids pDAB6031, pDAB6032 or pDAB6033, and inoculated into 250 mL of LB containing 50 μg/mL chloramphenicol and 75 μM IPTG. After growth for 24 hrs at 28° C. with shaking at 180 rpm, the cells were centrifuged for 10 min at 5500×g. The pellets were resuspended in 5 mL of phosphate solution and transferred to 50 mL conical tubes containing 1.5 mL of 0.1 mm diameter glass beads, then were sonicated for two 45 sec bursts at "constant" and a setting of 30 as described above.

The samples were centrifuged at 3000×g for 15 min, the supernatant was transferred to 2 mL microcentrifuge tubes, centrifuged for 5 min at 14,000 rpm, and the supernatants were then transferred to 15 mL tubes. The protein concentrations were measured as described above and the lysates were adjusted to 5 mg/mL with phosphate buffer. A set of three samples per lysate was submitted for insect bioassay. To the first sample, phosphate buffer was added in place of purified toxin; to the second sample, sufficient TcdA protein was added to provide a dose of 50 ng/cm$^2$ in the insect bioassay well, and to the third sample, sufficient XptA2$_{wi}$ protein was added to provide a dose of 250 ng/cm$^2$ in the insect bioassay well.

The results of the bioassay are shown in Table 6. Control samples, which were not supplemented with low levels of added TcdA or XptA2$_{wi}$ protein, (e.g. samples from vector, pDAB6031, pDAB6032 and pDAB6033), had little impact on the insects. Likewise, samples which contained low levels of TcdA or XptA2$_{wi}$, with either pDAB6031 or pDAB6032 lysates, had minimal effects. In contrast, significant activity was observed in the samples which included low levels of TcdA or XptA2$_{wi}$ with pDAB6033 lysates.

TABLE 6

Response of coleopteran and lepidopteran species to *E. coli* lysates and purified proteins. Responses are presented as percent mortality/percent growth inhibition.

| Sample | Lysates Tested | Insect Species: southern corn rootworm | corn earworm | tobacco budworm | beet armyworm |
|---|---|---|---|---|---|
| vector | | 0/0 | 8/0 | 0/0 | 31/0 |
| pDAB6031 | XptB1$_{xb}$ | 0/0 | 0/0 | 0/0 | 31/33 |
| pDAB6032 | XptC1$_{xb}$ | 0/0 | 4/11 | 0/2 | 13/15 |
| pDAB6033 | XptB1$_{xb}$ + XptC1$_{xb}$ | 0/0 | 0/0 | 0/6 | 13/38 |
| Vector + TcdA | | 4/0 | 4/3 | 0/6 | 25/22 |
| pDAB6031 + TcdA | XptB1$_{xb}$ + TcdA | 0/0 | 0/0 | 0/5 | 13/34 |
| pDAB6032 + TcdA | XptC1$_{xb}$ + TcdA | 0/0 | 0/2 | 0/14 | 6/25 |
| pDAB6033 + TcdA | XptB1$_{xb}$ + XptC1$_{xb}$ + TcdA | 25/68 | 4/14 | 4/0 | 31/48 |
| Vector + XptA2$_{wi}$ | | 0/0 | 0/79 | 0/9 | 31/0 |
| pDAB6031 + XptA2$_{wi}$ | XptB1$_{xb}$ + XptA2$_{wi}$ | 0/0 | 4/75 | 8/22 | 25/36 |
| pDAB6032 + XptA2$_{wi}$ | XptC1$_{xb}$ + XptA2$_{wi}$ | 0/0 | 0/71 | 0/22 | 6/14 |
| pDAB6033 + XptA2$_{wi}$ | XptB1$_{xb}$ + XptC1$_{xb}$ + XptA2$_{wi}$ | 0/0 | 83/100 | 29/98 | 81/100 |

Example 8

Identification, Purification, and Characterization of XptB1$_{xb}$ and XptC1$_{xb}$ Proteins of *Xenorhabdus bovienii* Strain ILM104

This example relates to bioassay driven fractionation of a pDAB6033-containing *E. coli* lysate resulted in the identification by MALDI-TOF of two co-purifying proteins: XptB1$_{xb}$ and XptC1$_{xb}$. Peaks containing these 2 proteins effectively potentiated the activity of TcdA and XptA2$_{wi}$.

Active fractions were identified based on their ability to synergize or potentiate the activity of TcdA against southern corn rootworm or XptA2$_{wi}$ against corn earworm. All bioassays were conducted in the 128-well format described in Example 2.

Three liters of broth from cultures of transgenic *E. coli* containing pDAB6033 were centrifuged (10,000×g for 20 min.) and the cells brought up into 150 mL of 25 mM Tris-HCl, pH 7.8 (T-buffer) containing 0.1 M DTT (dithiothreitol) and 1 M EDTA (ethylenediaminetetraacetic acid). A general protease inhibitor cocktail (Sigma Chemical catalog number P2714) was added according to manufacturer's instructions. The cells were lysed by sonication of small fractions of the suspended cells at full power for 30 seconds each, while holding on ice. This process was repeated three times and then the broken cells were centrifuged at 48,400×g for 1 hr at 4° C. The lysate was collected and brought to 80% saturation in ammonium sulfate. The precipitated protein was collected by centrifugation at 48,400×g for 15 minutes, suspended in T-buffer, and dialyzed overnight against 2 liters of T-buffer with one change of the buffer. The suspended proteins were clarified by centrifugation (48,400×g for 10 minutes), then loaded onto a Q Sepharose XL anion exchange column (1.6 cm dia.×10 cm long). The column washed with 2 column volumes of T-buffer, then batch eluted with a step gradient of 300 mM NaCl in T-buffer. Proteins eluting with 300 mM NaCl were pooled and $(NH_4)_2SO_4$ added to a final concentration of 1 M and loaded onto a phenyl sepharose hydrophobic-interaction column (1.0 cm dia.×10 cm long). After washing with 2 column volumes of 1.25 M $(NH_4)_2SO_4$ in 25 mM T-buffer, proteins were eluted using a linear gradient starting at 625 mM to 0 mM $(NH_4)_2SO_4$ in T-buffer over 10 column volumes, with an additional isocratic elution of 4 column volumes of T-buffer. Proteins of interest eluted at conductance between 40-60 mS/cm. These samples were pooled and dialyzed overnight against T-buffer at 4° C. The dialyzed protein sample was then loaded onto a Mono Q anion exchange column (1.0 cm diameter×10 cm long) equilibrated in T-buffer. Proteins were eluted using a linear gradient, starting at 0 to 400 mM NaCl over 15 column volumes. Two peaks of activity were detected from protein fractions eluting between 22-24 mS/cm conductance (Peak 1 and Peak 2). An example of the potentiating activity of Peaks 1 and 2 is shown in Table 7. Subsequent purification and analysis were performed on both Peak 1 and Peak 2.

The peaks were concentrated to 1.0 mL and loaded onto a Superdex 200 (1.6 cm dia.×60 cm long) size exclusion column at 1.0 mL/min using a buffer consisting of 50 mM sodium phosphate, 100 mM NaCl, 0.05% Tween-20 and 10% glycerol, pH 7.8. In both cases, the protein eluted as a single major peak corresponding to a molecular weight of approximately 300 kDa. The major protein peak was diluted and further purified by loading onto a Mono Q (0.5 cm dia.×5 cm long) anion exchange column equilibrated in T-buffer and eluted using a 150-300 mM NaCl gradient over 15 column volumes.

Fractions from this anion exchange purification were analyzed by SDS-PAGE. Protein fractions (20 μL) were added to 5× concentrated Laemmli buffer (section 10 of Ausubel, et al. (Current Protocols in Molecular Biology, John Wiley and Sons, Inc., New York, N.Y.)) (5 μL), heated to 90° C. for 3 minutes, centrifuged, and the supernatant loaded onto a 4-20% polyacrylamide Tris glycine gel in SDS running buffer. Proteins were separated using 160 V for 90 min, and visualized by staining with Coomassie Blue, then destaining with a solution containing 5% aqueous methanol plus 7% acetic acid. The gels were imaged and analyzed using a Bio-Rad Fluoro-S Multi Imager. The gels from both Peak 1 and Peak 2 contained two predominant bands, one migrating at a ~170 kDa and the other migrating at ~80 kDa. The gel from Peak 1 contained three additional proteins that migrated at approximately 18, 33 and 50 kDa. Retrospective analysis revealed that the ~170 kDa and ~80 kDa bands were abundant at the initial stages of purification and became progressively enriched at each step.

The identity of the 2 major bands was determined using MALDI-TOF analysis. The ~170 kDa and ~80 kDa bands were excised from the SDS gel of highly enriched fractions of the pDAB6033 lysate and were placed into siliconized Eppendorf microcentrifuge tubes and destained with 50% acetonitrile in 12.5 mM $NH_4HCO_3$. The samples were dried in a Speed-Vac (Savant Instruments, Holbrook, N.Y.) and digested with sequencing grade trypsin (Roche Diagnostics, Indianapolis, Ind.) overnight (approximately 16 hours) at 37° C. After a brief centrifugation to pellet the gel pieces, the supernatant containing the peptides was transferred to a fresh tube and dried in a Speed-Vac. The peptides were then suspended in 6 μL of 0.1% trifluoroacetic acid (TFA), absorbed to a $C_{18}$ ZipTip resin (Millipore, Bedford, Mass.) and eluted with 75% acetonitrile/0.1% TFA. The eluent was analyzed as described below.

The extracted peptides were analyzed using MALDI-TOF mass spectrometry to produce peptide mass fingerprints (PMF) on a Voyager DE-STR MALDI-TOF mass spectrometer (PerSeptive Biosystems, Framingham, Mass.). The samples derived above were spotted onto a MALDI stainless steel plate in a 1:1 ratio of 0.5 μL of sample with 0.5 μL of matrix mixed on the plate using the dried droplet spotting technique (air dried). The matrix was a saturated solution of α-cyano-4-hydroxycinnamic acid in 50% acetonitrile with 0.1% TFA. External calibration was performed by using a solution of angiotensin I, adrenocorticotropic hormone (ACTH, clip 1-17, 18-39, 7-38). Internal calibration was performed using the autolytic trypsin peak at Mn/z 2163.05. All mass spectra were collected in the positive ion reflector mode with delayed extraction. The instrument utilizes a 337 nm nitrogen laser for the desorption/ionization event and a 3.0 meter reflector time-of-flight tube. Acquired spectra were de-isotoped and PMF tables were generated for database searching. The database searching was performed using a Web based search engine Mascot (MatrixSciences, UK). The mass tolerance was set at 0.15 Da and no modifications were elected during the search. Analysis of the samples extracted from the ~170 kDa band confirmed the identity as $XptB1_{xb}$. Analysis of the samples extracted from the ~80 kDa band confirmed the identity as $XptC1_{xb}$. Although the predicted molecular weight of the $XptC1_{xb}$ protein as calculated from the gene sequence (SEQ ID NO:3) is 108 kDa, the extracted protein ran significantly faster than expected in the SDS/PAGE. The presence of peptide fragments representing the entire peptide sequence indicated that the protein as extracted is full length.

TABLE 7

Biological activity of purified Peak 1 and Peak 2 from pDAB6033.

| Sample | corn earworm | | southern corn rootworm | |
|---|---|---|---|---|
| | Dead | Stunted | Dead | Stunted |
| Peak 1 | | | | |
| 0 | 0 | 0 | 0 | 0 |
| 125 | 2 | 6 | 4 | 2 |
| Peak 2 | | | | |
| 0 | 1 | 0 | 0 | 0 |
| 125 | 0 | 8 | 5 | 3 |

Values in column labeled Sample represent the concentration of Peak 1 or Peak 2 $XptB1_{xb}$/$XptC1_{xb}$ proteins applied to the diet (in ng/cm$^2$). For bioassays against corn earworm, 250 ng/cm$^2$ of $XptA2_{xi}$ was included in the bioassay. For bioassays against southern corn rootworm, 100 ng/cm$^2$ of TcdA was included in the bioassay. A total of eight larvae were used per sample.

Example 9

Full Sequencing of New Class "A" Toxin Complex Gene from *Xenorhabdus bovienii* Strain ILM104

In Example 6, cosmid 5H4 was identified as encoding proteins which increased the activity of the Class A proteins TcdA and XptA2. A subclone of this cosmid, plasmid pDAB6026, was shown by insect bioassay to encode the synergistic activity. DNA sequence analysis of pDAB6026 identified three open reading frames. The first (disclosed as SEQ ID NO:1) has similarity to known toxin complex genes belonging to the "B" class. This OF was therefore called $xptB1_{xb}$ and encodes the $XptB1_{xb}$ protein disclosed as SEQ ID NO:2. The second ORE (SEQ ID NO:3) encodes a protein ($XptC1_{xb}$, SEQ ID NO:4) with homology to toxin complex "C" proteins and therefore was named $xptC1_{xb}$. These two reading frames were shown to be responsible for the synergistic or enhanced activity with TcdA and XptA2 Examples 7 and 8). A partial open reading from was also discovered (SEQ ID NO:5) that has significant homology to the "A" class of toxin complex genes. This partial ORF encodes the protein sequence disclosed in SEQ ID NO:6.

The full-length DNA sequence of this new Class A gene and the deduced sequence of the encoded protein were determined from analysis of the entire DNA sequence of the 5H4 cosmid. Cosmid DNA was prepared as described in Example 6 and sent to Lark Technologies (Houston, Tex.) for full DNA sequence determination. The DNA coding sequence of the new Class A gene, named $xptA1_{xb}$, was determined and is disclosed as SEQ ID NO:10. The protein encoded by this reading frame ($XptA1_{xb}$) is disclosed as SEQ ID NO:11.

The invention claimed is:

1. An isolated protein that has toxin activity against an insect, wherein said protein is at least 95% identical to SEQ ID NO:2.

2. A method of inhibiting an insect wherein said method comprises providing said insect with an isolated protein for ingestion, wherein said protein has toxin activity against said insect, and said protein is at least 95% identical to SEQ ID NO:2.

3. The method of claim 2 wherein said protein is produced by and present in a plant.

4. The protein of claim 1 wherein said protein comprises the amino acid sequence of SEQ ID NO:2.

* * * * *

SEQUENCE LISTING

<160> NUMBER OF SEQ ID NOS: 11

<210> SEQ ID NO 1
<211> LENGTH: 4521
<212> TYPE: DNA
<213> ORGANISM: Xenorhabdus bovienii

<400> SEQUENCE: 1

```
atgaaacaag attcacagga catgacagta acacagctgt ccctgcccaa aggggggcggt      60
gcgatcagtg gcatgggtga cactatcagc aatgcagggc cggatgggat ggcttcgctt     120
tccgtgcctt tgcctatctc tgccggtcgg ggggcgcac cgaatttatc cctgaactac      180
agtagcggag caggaaacgg gtcatttggt attggctggc aatccagtac catggctatc     240
agccgtcgta ctcaacatgg cgtaccgcaa tatcacggcg aagatacttt tttatgtccg     300
atgggagaag tgatggcggt tgccgtcaat cagagcgggc aacccgatgt gcgtaaaacc     360
gataaactat taggcgggca actgcctgtt acttataccg ttacgcgtca tcagcccaga     420
aatattcagc acttcagcaa acttgaatac tggcagcccc caacggatgt ggaaaccacg     480
ccttttttggt taatgtattc acccgatgga caaattcaca ttttcggaaa aactgagcag     540
gctcagatcg ctaacccggc agaggtttca cagattgccc aatggctttt ggaagaaacc     600
gtaacaccag cgggagaaca catttattac cagtatcggg cagaagacga tatcggttgt     660
gatgacagcg aaaaaaatgc ccaccctaat gccagtgctc aacgttattt gactcaggtg     720
aactacggca atattacacc tgaatccagc ctgcttgtgc tgaagaatac gccaccggcg     780
gataacgaat ggctattcca tttggttttt gattatggtg aacgagcgca ggaaataaac     840
acggttcctc ctttcaaagc accttcaaac aactggaaaa tacggccaga ccgtttctcc     900
cgctttgaat atggttttga ggtgcgaacc cgccgcctgt gtcaacaaat tctgatgttc     960
catcgcctga atcccttgc aggagaacag attgacggag aagaaatccc tgccttggtt     1020
gcccgtctgc ttctcagtta tgacctgaac gacagcgtga caacccttac cgccattcgg    1080
caaatggcgt atgaaactga cgcaaccta atcgcttac cgccactgga gtttgactat     1140
cagcccttttg aggcaaaagt cacgcagaaa tggcaggaaa tgcctcaatt ggccggattg    1200
aatgcccaac aaccttacca actcgtcgat ctctatggtg aaggtatctc cggcatcttg    1260
tatcaggaca gacccggagc atggtggtat caggcaccga tccgtcagaa aaacgttgaa    1320
gatattaacg ctgtcaccta tagcccaata aaccccttac ctaagatccc cagccagcag    1380
gacagagcaa cgttgatgga tatcgacggt gatggacatc tggattgggt gatcgctggc    1440
gcaggtattc agggggcgta cagtatgcag ccgaatggag agtggacaca ctttattccc    1500
atttctgcac tgccaacaga atattttcat ccacaggcac aactggcgga tctggtgggg    1560
gccgggttat ctgatttagc gctgattggc cccagaagtg tgcgtttata tgccaacgac    1620
cgaggaaact ggaaagcggg tattaatgtt atgccacctg atggtgtgaa tttgccgata    1680
tttggtggtg atgccagcag tctggtcgca ttttctgaca tgttgggatc gggacagcag    1740
catttggtgg aaattgccgc tcagagcgtc aaatgctggc cgaatctagg acatggccgt    1800
tttggtgcgc ctattttgct gccggggttt agccagccga atggaacatt caatgctaac    1860
caagttttc tggcagatat cgatggttcc ggcaccgccg acatcatcta tgcacacagt    1920
acgtatctgg atatttacct gaacgaaagc ggcaaccgtt tcagtgcacc cgttcggctt    1980
aatttgccgg aagggggtgat gtttgacaat acctgtcagt tacaggtgtc ggatattcaa    2040
```

```
ggattgggcg ctgccagcat tgtactgacc gtacctcata tgacaccgcg ccattggcgt    2100
tatgatttta ctcacaataa accttggctg ctcaatgtca tcaacaacaa tcgtggcgca    2160
gaaaccacgt tgttttaccg tagttctgcc caattctggc tggatgaaaa aagtcagatc    2220
gaagagctgg gaaaatttgc agcgagttat ctgccttcc ccatacattt gttgtggcgc    2280
aatgaggcgc tggatgaaat tactggtaat cgactgacta aggtcatgaa ttatgcccac    2340
ggtgcatggg atggcagaga gagagaattt tgcggatttg ccgtgtaac gcaaattgat    2400 accgacgaat tgccaaggg aaccacagag aaagcgccgg atgaaaatat ctatccttcc    2460
cgtagcataa gctggtttgc cacgggttta ccagaagtgg attctcaact tccggcagaa    2520
tactggcgtg gtgacgatca ggcatttgcc ggctttacac cgcgcttcac tcgttatgaa    2580
aaaggtaatg cggggcaaga ggggcaggat accccgatta agaaccgac cgaaacagaa    2640 gcgtattggc ttaaccgcgc catgaaaggc caattactgc gcagtgaagt ctatggtgac    2700
gacaaaacag aaaaagctaa aattccgtac accgtcacag aagctcgctg tcaggtcaga    2760
ttaattccca gcaatgacga agccgcgccg tcgtcttgga cgtcgatcat tgaaaaccgc    2820
agttatcact atgagcgtat cgtcgtcgat ccgagttgca acaacaggt cgtgctcaag    2880 gcggatgaat atggcttccc actggcaaaa gtagatatcg cctatccacg gcgcaataaa    2940
ccggcacaga acccttatcc ggattcgtta ccggatactc tgttcgccga tagctatgac    3000
gaccagcaaa aacagttata tctgacaaaa cagcagcaga gctattacca cctgacccag    3060
caggatgatt gggttctggg tttgacggat agccgataca gcgaagttta tcattatgcg    3120
caaactgacg ctcaaagtga catccccaag gcagggctga tattggaaga cctgctgaaa    3180
gttgacggcc tgataggtaa agacaagact tttatctatt tagggcagca gcgagtggct    3240
tatgtgggag gagatgcaga aaaaccgaca cgtcaggtgc gggtggctta tacagaaacc    3300
gctgcttttg atgacaatgc gctgcacgcc tttgatggcg tgattgcccc tgatgaactg    3360
acgcaacagt tgctggcggg tggatacctg ctcgtgccgc agatttctga tgtggcaggc    3420
agtagtgaaa aggtatgggt agctcggcag ggatacaccg aatacggcag tgctgctcaa    3480
ttctaccggc cactcatcca gcgcaaaagc ttgctgaccg gaaaatatac ccttagttgg    3540
gatacgcact attgtgtggt ggtaaaaacc gaagatggtg cgggaatgac cacgcaagcg    3600
aagtacgatt accgcttcct gcttccggcg caattgacag atatcaatga caaccagcac    3660
atcgtgacat ttaatgcatt ggggcaggtg acttccagcc gtttctgggg cacagaaaat    3720
ggcaaaataa gcggttactc gacgccggag agtaaaccgt tcacagtacc cgataccgtc    3780
gaaaaagccc ttgccttgca accgacgatc ccggtttcac agtgcaacat ttatgtgccg    3840
gatagttgga tgcggcttct gccccaacag tctctgactg gccagctaaa agaggggaa    3900 actttgtgga acgcattaca ccgggcgggt gtagtaacgg aagacggttt gatctgtgaa    3960
ctggcctatc gtcgttggat caaacgtcag gcaacgtctt caatgatggc cgtgacatta    4020
cagcaaatct tggctcagac tccacgacaa cctccgcatg ccatgacgat cacgacagat    4080
cgttatgaca gcgattctca gcagcaactt cggcagtcga tagtattgag tgatggtttt    4140
ggtcgcgtat tgcaaagcgc ccagcgtcat gaagcaggag aggcatggca gcgtgcagaa    4200
gatggttctt tggttgtcga taataccggt aaacccgttg ttgctaatac cacaacgcgc    4260
tgggcagtat ccggtcgcac agaatacgac ggcaaagggc aggcgatcag agcttacctg    4320
ccttattatc tcaatgattg gcgctatgtc agtgatgaca gcgcccggga tgacctgtac    4380
```

-continued

```
gccgatacccc atttttacga tcctctgggg cgtgaatatc aggtaaaaac cgcgaaagga    4440 tttttggcgtg aaacatgtt tatgccgtgg tttgtcgtca atgaagatga aaatgacaca    4500
gcagcacgtt taacatctta a                                              4521
```

<210> SEQ ID NO 2
<211> LENGTH: 1506
<212> TYPE: PRT
<213> ORGANISM: Xenorhabdus bovienii

<400> SEQUENCE: 2

```
Met Lys Gln Asp Ser Gln Asp Met Thr Val Thr Gln Leu Ser Leu Pro
  1               5                  10                  15

Lys Gly Gly Gly Ala Ile Ser Gly Met Gly Asp Thr Ile Ser Asn Ala
                 20                  25                  30

Gly Pro Asp Gly Met Ala Ser Leu Ser Val Pro Leu Pro Ile Ser Ala
             35                  40                  45

Gly Arg Gly Gly Ala Pro Asn Leu Ser Leu Asn Tyr Ser Ser Gly Ala
         50                  55                  60

Gly Asn Gly Ser Phe Gly Ile Gly Trp Gln Ser Ser Thr Met Ala Ile
 65                  70                  75                  80

Ser Arg Arg Thr Gln His Gly Val Pro Gln Tyr His Gly Glu Asp Thr
                 85                  90                  95

Phe Leu Cys Pro Met Gly Glu Val Met Ala Val Ala Val Asn Gln Ser
            100                 105                 110

Gly Gln Pro Asp Val Arg Lys Thr Asp Lys Leu Leu Gly Gly Gln Leu
        115                 120                 125

Pro Val Thr Tyr Thr Val Thr Arg His Gln Pro Arg Asn Ile Gln His
    130                 135                 140

Phe Ser Lys Leu Glu Tyr Trp Gln Pro Pro Thr Asp Val Glu Thr Thr
145                 150                 155                 160

Pro Phe Trp Leu Met Tyr Ser Pro Asp Gly Gln Ile His Ile Phe Gly
                165                 170                 175

Lys Thr Glu Gln Ala Gln Ile Ala Asn Pro Ala Glu Val Ser Gln Ile
            180                 185                 190

Ala Gln Trp Leu Leu Glu Glu Thr Val Thr Pro Ala Gly Glu His Ile
        195                 200                 205

Tyr Tyr Gln Tyr Arg Ala Glu Asp Ile Gly Cys Asp Asp Ser Glu
    210                 215                 220

Lys Asn Ala His Pro Asn Ala Ser Ala Gln Arg Tyr Leu Thr Gln Val
225                 230                 235                 240

Asn Tyr Gly Asn Ile Thr Pro Glu Ser Ser Leu Leu Val Leu Lys Asn
                245                 250                 255

Thr Pro Pro Ala Asp Asn Glu Trp Leu Phe His Leu Val Phe Asp Tyr
            260                 265                 270

Gly Glu Arg Ala Gln Glu Ile Asn Thr Val Pro Pro Phe Lys Ala Pro
        275                 280                 285

Ser Asn Asn Trp Lys Ile Arg Pro Asp Arg Phe Ser Arg Phe Glu Tyr
    290                 295                 300

Gly Phe Glu Val Arg Thr Arg Arg Leu Cys Gln Gln Ile Leu Met Phe
305                 310                 315                 320

His Arg Leu Lys Ser Leu Ala Gly Glu Gln Ile Asp Gly Glu Glu Ile
                325                 330                 335

Pro Ala Leu Val Ala Arg Leu Leu Leu Ser Tyr Asp Leu Asn Asp Ser
            340                 345                 350
```

```
Val Thr Thr Leu Thr Ala Ile Arg Gln Met Ala Tyr Glu Thr Asp Ala
        355                 360                 365

Thr Leu Ile Ala Leu Pro Pro Leu Glu Phe Asp Tyr Gln Pro Phe Glu
    370                 375                 380

Ala Lys Val Thr Gln Lys Trp Gln Glu Met Pro Gln Leu Ala Gly Leu
385                 390                 395                 400

Asn Ala Gln Gln Pro Tyr Gln Leu Val Asp Leu Tyr Gly Glu Gly Ile
                405                 410                 415

Ser Gly Ile Leu Tyr Gln Asp Arg Pro Gly Ala Trp Trp Tyr Gln Ala
            420                 425                 430

Pro Ile Arg Gln Lys Asn Val Glu Asp Ile Asn Ala Val Thr Tyr Ser
        435                 440                 445

Pro Ile Asn Pro Leu Pro Lys Ile Pro Ser Gln Gln Asp Arg Ala Thr
    450                 455                 460

Leu Met Asp Ile Asp Gly Asp Gly His Leu Asp Trp Val Ile Ala Gly
465                 470                 475                 480

Ala Gly Ile Gln Gly Arg Tyr Ser Met Gln Pro Asn Gly Glu Trp Thr
                485                 490                 495

His Phe Ile Pro Ile Ser Ala Leu Pro Thr Glu Tyr Phe His Pro Gln
            500                 505                 510

Ala Gln Leu Ala Asp Leu Val Gly Ala Gly Leu Ser Asp Leu Ala Leu
        515                 520                 525

Ile Gly Pro Arg Ser Val Arg Leu Tyr Ala Asn Asp Arg Gly Asn Trp
    530                 535                 540

Lys Ala Gly Ile Asn Val Met Pro Pro Asp Gly Val Asn Leu Pro Ile
545                 550                 555                 560

Phe Gly Gly Asp Ala Ser Ser Leu Val Ala Phe Ser Asp Met Leu Gly
                565                 570                 575

Ser Gly Gln Gln His Leu Val Glu Ile Ala Ala Gln Ser Val Lys Cys
            580                 585                 590

Trp Pro Asn Leu Gly His Gly Arg Phe Gly Ala Ala Ile Leu Leu Pro
        595                 600                 605

Gly Phe Ser Gln Pro Asn Gly Thr Phe Asn Ala Asn Gln Val Phe Leu
    610                 615                 620

Ala Asp Ile Asp Gly Ser Gly Thr Ala Asp Ile Ile Tyr Ala His Ser
625                 630                 635                 640

Thr Tyr Leu Asp Ile Tyr Leu Asn Glu Ser Gly Asn Arg Phe Ser Ala
                645                 650                 655

Pro Val Arg Leu Asn Leu Pro Glu Gly Val Met Phe Asp Asn Thr Cys
            660                 665                 670

Gln Leu Gln Val Ser Asp Ile Gln Gly Leu Gly Ala Ala Ser Ile Val
        675                 680                 685

Leu Thr Val Pro His Met Thr Pro Arg His Trp Arg Tyr Asp Phe Thr
    690                 695                 700

His Asn Lys Pro Trp Leu Leu Asn Val Ile Asn Asn Arg Gly Ala
705                 710                 715                 720

Glu Thr Thr Leu Phe Tyr Arg Ser Ser Ala Gln Phe Trp Leu Asp Glu
                725                 730                 735

Lys Ser Gln Ile Glu Glu Leu Gly Lys Phe Ala Ala Ser Tyr Leu Pro
            740                 745                 750

Phe Pro Ile His Leu Leu Trp Arg Asn Glu Ala Leu Asp Glu Ile Thr
        755                 760                 765
```

```
Gly Asn Arg Leu Thr Lys Val Met Asn Tyr Ala His Gly Ala Trp Asp
            770                 775                 780

Gly Arg Glu Arg Glu Phe Cys Gly Phe Gly Arg Val Thr Gln Ile Asp
785                 790                 795                 800

Thr Asp Glu Phe Ala Lys Gly Thr Thr Glu Lys Ala Pro Asp Glu Asn
                805                 810                 815

Ile Tyr Pro Ser Arg Ser Ile Ser Trp Phe Ala Thr Gly Leu Pro Glu
            820                 825                 830

Val Asp Ser Gln Leu Pro Ala Glu Tyr Trp Arg Gly Asp Asp Gln Ala
            835                 840                 845

Phe Ala Gly Phe Thr Pro Arg Phe Thr Arg Tyr Glu Lys Gly Asn Ala
            850                 855                 860

Gly Gln Glu Gly Gln Asp Thr Pro Ile Lys Glu Pro Thr Glu Thr Glu
865                 870                 875                 880

Ala Tyr Trp Leu Asn Arg Ala Met Lys Gly Gln Leu Leu Arg Ser Glu
                885                 890                 895

Val Tyr Gly Asp Asp Lys Thr Glu Lys Ala Lys Ile Pro Tyr Thr Val
            900                 905                 910

Thr Glu Ala Arg Cys Gln Val Arg Leu Ile Pro Ser Asn Asp Glu Ala
            915                 920                 925

Ala Pro Ser Ser Trp Thr Ser Ile Ile Glu Asn Arg Ser Tyr His Tyr
            930                 935                 940

Glu Arg Ile Val Val Asp Pro Ser Cys Lys Gln Gln Val Val Leu Lys
945                 950                 955                 960

Ala Asp Glu Tyr Gly Phe Pro Leu Ala Lys Val Asp Ile Ala Tyr Pro
                965                 970                 975

Arg Arg Asn Lys Pro Ala Gln Asn Pro Tyr Pro Asp Ser Leu Pro Asp
            980                 985                 990

Thr Leu Phe Ala Asp Ser Tyr Asp Asp Gln Gln Lys Gln Leu Tyr Leu
            995                 1000                1005

Thr Lys Gln Gln Gln Ser Tyr Tyr His Leu Thr Gln Gln Asp Asp
    1010                1015                1020

Trp Val Leu Gly Leu Thr Asp Ser Arg Tyr Ser Glu Val Tyr His
    1025                1030                1035

Tyr Ala Gln Thr Asp Ala Gln Ser Asp Ile Pro Lys Ala Gly Leu
    1040                1045                1050

Ile Leu Glu Asp Leu Leu Lys Val Asp Gly Leu Ile Gly Lys Asp
    1055                1060                1065

Lys Thr Phe Ile Tyr Leu Gly Gln Gln Arg Val Ala Tyr Val Gly
    1070                1075                1080

Gly Asp Ala Glu Lys Pro Thr Arg Gln Val Arg Val Ala Tyr Thr
    1085                1090                1095

Glu Thr Ala Ala Phe Asp Asp Asn Ala Leu His Ala Phe Asp Gly
    1100                1105                1110

Val Ile Ala Pro Asp Glu Leu Thr Gln Gln Leu Leu Ala Gly Gly
    1115                1120                1125

Tyr Leu Leu Val Pro Gln Ile Ser Asp Val Ala Gly Ser Ser Glu
    1130                1135                1140

Lys Val Trp Val Ala Arg Gln Gly Tyr Thr Glu Tyr Gly Ser Ala
    1145                1150                1155

Ala Gln Phe Tyr Arg Pro Leu Ile Gln Arg Lys Ser Leu Leu Thr
    1160                1165                1170

Gly Lys Tyr Thr Leu Ser Trp Asp Thr His Tyr Cys Val Val Val
```

-continued

| | | | | | | | | |
|---|---|---|---|---|---|---|---|---|
| | | 1175 | | | 1180 | | | 1185 |

Lys Thr Glu Asp Gly Ala Gly Met Thr Thr Gln Ala Lys Tyr Asp
1190                         1195                         1200

Tyr Arg Phe Leu Leu Pro Ala Gln Leu Thr Asp Ile Asn Asp Asn
1205                         1210                         1215

Gln His Ile Val Thr Phe Asn Ala Leu Gly Gln Val Thr Ser Ser
1220                         1225                         1230

Arg Phe Trp Gly Thr Glu Asn Gly Lys Ile Ser Gly Tyr Ser Thr
1235                         1240                         1245

Pro Glu Ser Lys Pro Phe Thr Val Pro Asp Thr Val Glu Lys Ala
1250                         1255                         1260

Leu Ala Leu Gln Pro Thr Ile Pro Val Ser Gln Cys Asn Ile Tyr
1265                         1270                         1275

Val Pro Asp Ser Trp Met Arg Leu Leu Pro Gln Gln Ser Leu Thr
1280                         1285                         1290

Gly Gln Leu Lys Glu Gly Glu Thr Leu Trp Asn Ala Leu His Arg
1295                         1300                         1305

Ala Gly Val Val Thr Glu Asp Gly Leu Ile Cys Glu Leu Ala Tyr
1310                         1315                         1320

Arg Arg Trp Ile Lys Arg Gln Ala Thr Ser Ser Met Met Ala Val
1325                         1330                         1335

Thr Leu Gln Gln Ile Leu Ala Gln Thr Pro Arg Gln Pro Pro His
1340                         1345                         1350

Ala Met Thr Ile Thr Thr Asp Arg Tyr Asp Ser Asp Ser Gln Gln
1355                         1360                         1365

Gln Leu Arg Gln Ser Ile Val Leu Ser Asp Gly Phe Gly Arg Val
1370                         1375                         1380

Leu Gln Ser Ala Gln Arg His Glu Ala Gly Glu Ala Trp Gln Arg
1385                         1390                         1395

Ala Glu Asp Gly Ser Leu Val Val Asp Asn Thr Gly Lys Pro Val
1400                         1405                         1410

Val Ala Asn Thr Thr Thr Arg Trp Ala Val Ser Gly Arg Thr Glu
1415                         1420                         1425

Tyr Asp Gly Lys Gly Gln Ala Ile Arg Ala Tyr Leu Pro Tyr Tyr
1430                         1435                         1440

Leu Asn Asp Trp Arg Tyr Val Ser Asp Ser Ala Arg Asp Asp
1445                         1450                         1455

Leu Tyr Ala Asp Thr His Phe Tyr Asp Pro Leu Gly Arg Glu Tyr
1460                         1465                         1470

Gln Val Lys Thr Ala Lys Gly Phe Trp Arg Glu Asn Met Phe Met
1475                         1480                         1485

Pro Trp Phe Val Val Asn Glu Asp Glu Asn Asp Thr Ala Ala Arg
1490                         1495                         1500

Leu Thr Ser
1505

<210> SEQ ID NO 3
<211> LENGTH: 2889
<212> TYPE: DNA
<213> ORGANISM: Xenorhabdus bovienii

<400> SEQUENCE: 3

```
atgaatgttt ttaatccaac tttatatgcc ggtacaccga ctgtcaccgt catggacaat    60
cgagggctgt cagtgcggga tattgcttat caccgtacaa cagcaggaga gcaggctgac   120
```

-continued

```
actcgcatca cccgccatca atacagtccc cataattttt taatcgagag cattgatcca      180 cgccttttg atttgcaatc tcagagcacc ataaaaccta atttcaccta ctgtcctgcc       240
ttgaagggtg atgtcctacg acagagagt gtggatgccg acaaactgt cattttgagt       300 gacatcgaag gtcgtccgtt actgaatatc agtgcgatgg gtgtcgtcaa acactggcaa      360
tatgaagaga gtacattgcc ggggcgcttg ctcgctgtca gtgaacggaa gaatgaggct      420
tcaacacccc aaattattga acggtttatt tggtcgggaa atagcccatc agaaaaagat     480
cacaatttgg cgggaaaata tcttcgtcat tatgataccg ccggattaaa ccagcttaat     540
gctgtgtctc tgaccagcgt ggatctctca caatcccgtc agttattgca ggatgatgtc     600
acagcagatt ggagcggaag tgacgaatcc cagtggaaga cgcgactgag taacgacata     660
ttcacaaccg aaatcaccgc tgatgcggtt ggcaatttct tgactcagaa tgatgccaaa     720
agcaaccagc aacgattgtc ctatgatgtg gcagggcagt taaaggcaag ctggctgacg     780
ataaaaggcc agaatgagca ggtgatagtt aactccctga cttactccgc cgcagggcag    840
aaactgcgtg aagagcaggg taacggcgtt gtcactgaat actcctatga agcacaaacc    900
tggcgtttga taggtgtaac ggcttaccgt cagtcagata aaaaaagatt gcaggatctt    960
gtctataact atgatccggt cggtaatctc ctgaatattc gcaataatgc agaggcaacc   1020
cgtttctggc gtaatcagat agtagaacca gagaaccact atgcttatga ctcgctttat   1080
caactcatca gtgctagtgg tcgagaaatc gccagtatcg gtcagcaggg cagccggctg   1140
cctgtaccga ttattcctct tcctgccaat gacgatgttt atactcgcta cacccgcaca   1200
tatcactatg atcgcggtgg aaatctctgc cagatccggc attgcgctcc tgctacagat   1260
aataagtaca ccacaaagat caccgtatcg aatcgtagta atcgtgcagt atgggatacc   1320
ttgaccacag atcccgccaa agtggatacc ctgtttgatc atggagggca tcaacttcaa   1380
ctccagtcag gccagacttt atgttggaac tatcggggtg aactacagca ataacaaag    1440 atacagcgtg acgaaaaacc cgcagataaa gagcggtatc gctatggtgt tgggctgcg    1500 cgggtcgtga aaatcagcac acagcaggcg gggggaagca gccatgtgca gcgtgttgtt   1560
tatctgccgg ggttggaact acgcacaact cagcatgatg cgacattaat cgaagactta   1620
caggtgatta tcatgggtga agcaggacgt gctcaggtac gcgtacttca ttgggaaata   1680
ccaccaccgg ataatcttaa caatgactca ctgcgttaca gctacgatag tttgatgggt   1740
tccagtcagc ttgaattgga tggagcaggg cagattatta cgcaggaaga atactacccc   1800
tatggaggta cagcaatatg ggcggcaaga aaccagaccg aagccaatta caaaaccatt   1860
cgctactccg gcaaagagcg tgatgcgacg gggctttatt actacgggca ccgttattat   1920
cagccgtggc tagggcgctg gttgagcgca gatcccgccg gaaccgtgga cggactgaat   1980
ctatatcgaa tggtgaggaa taacccgatt acttaccggg atgcagatgg gcttgcgccg   2040
ataggcgata agatcagcga agggatttat gagcctgagt tgcgagttgg tcttgaacga   2100
gatgacccaa atgtcagaga ttatgaccgg gtttatcctg atacggccaa gacagagatg   2160
atcgaagcaa ctgcgaccac aattgctccc agtcaaatgt tatcggcgca tgcttttgca   2220
tctgtaccta tattgacaga tttgtttaat cctcaaacag caaggctttc tcaaaagaca   2280
acggatattg tattaaacac acaaggtgga ggcgatttaa tctttactgg catgaatatt   2340
aaaggtaagg gaaagaaatt taatgcatta aaaatcgttg atacttatgg cggagaaatg   2400
cctgatagca aaaccgctat ttcagcatat tggcttccgc aaggtgggta tactgatatt   2460
```

```
ccgatacatc cgactggaat acaaaagtat ttgtttacgc ctgcgtttag tggttgcact    2520
ctggcagtag ataagcttaa cgaaaataca ttacgggcgt atcacgtcga aggaagtaag    2580
gaagatgctc aatataataa tttagcagtt gcagcgcacg gagagggttt ggtcatggct    2640
atggaatttc ctgactatgg atttcataca gacaaaacag ggcaaagact aaggaacaca    2700
cagggatttg cgtttatgtc ctacaatcaa tcccagaaaa aatgggaaat tcattatcaa    2760
aggcaagcat tgacatcaaa caccggtatc atgaatgtta gtgctaaaaa caagattcga    2820
ttgaatgccc ccagtcatgt aaaaaatagc tcaatcaaag gaactgaaat aatgacgaca    2880
catttttaa                                                            2889

<210> SEQ ID NO 4
<211> LENGTH: 962
<212> TYPE: PRT
<213> ORGANISM: Xenorhabdus bovienii

<400> SEQUENCE: 4
```

| | | | | | | | | | | | | | | |
|---|---|---|---|---|---|---|---|---|---|---|---|---|---|---|
| Met | Asn | Val | Phe | Asn | Pro | Thr | Leu | Tyr | Ala | Gly | Thr | Pro | Thr | Val | Thr |
| 1 | | | | 5 | | | | | 10 | | | | | 15 | |
| Val | Met | Asp | Asn | Arg | Gly | Leu | Ser | Val | Arg | Asp | Ile | Ala | Tyr | His | Arg |
| | | | 20 | | | | | 25 | | | | | 30 | | |
| Thr | Thr | Ala | Gly | Glu | Gln | Ala | Asp | Thr | Arg | Ile | Thr | Arg | His | Gln | Tyr |
| | | | 35 | | | | | 40 | | | | | 45 | | |
| Ser | Pro | His | Asn | Phe | Leu | Ile | Glu | Ser | Ile | Asp | Pro | Arg | Leu | Phe | Asp |
| | | | 50 | | | | | 55 | | | | | 60 | | |
| Leu | Gln | Ser | Gln | Ser | Thr | Ile | Lys | Pro | Asn | Phe | Thr | Tyr | Cys | Pro | Ala |
| 65 | | | | | 70 | | | | | 75 | | | | | 80 |
| Leu | Lys | Gly | Asp | Val | Leu | Arg | Thr | Glu | Ser | Val | Asp | Ala | Gly | Gln | Thr |
| | | | | 85 | | | | | 90 | | | | | 95 | |
| Val | Ile | Leu | Ser | Asp | Ile | Glu | Gly | Arg | Pro | Leu | Leu | Asn | Ile | Ser | Ala |
| | | | 100 | | | | | 105 | | | | | 110 | | |
| Met | Gly | Val | Val | Lys | His | Trp | Gln | Tyr | Glu | Glu | Ser | Thr | Leu | Pro | Gly |
| | | | 115 | | | | | 120 | | | | | 125 | | |
| Arg | Leu | Leu | Ala | Val | Ser | Glu | Arg | Lys | Asn | Glu | Ala | Ser | Thr | Pro | Gln |
| | 130 | | | | | 135 | | | | | 140 | | | | |
| Ile | Ile | Glu | Arg | Phe | Ile | Trp | Ser | Gly | Asn | Ser | Pro | Ser | Glu | Lys | Asp |
| 145 | | | | | 150 | | | | | 155 | | | | | 160 |
| His | Asn | Leu | Ala | Gly | Lys | Tyr | Leu | Arg | His | Tyr | Asp | Thr | Ala | Gly | Leu |
| | | | | 165 | | | | | 170 | | | | | 175 | |
| Asn | Gln | Leu | Asn | Ala | Val | Ser | Leu | Thr | Ser | Val | Asp | Leu | Ser | Gln | Ser |
| | | | 180 | | | | | 185 | | | | | 190 | | |
| Arg | Gln | Leu | Leu | Gln | Asp | Asp | Val | Thr | Ala | Asp | Trp | Ser | Gly | Ser | Asp |
| | | | 195 | | | | | 200 | | | | | 205 | | |
| Glu | Ser | Gln | Trp | Lys | Thr | Arg | Leu | Ser | Asn | Asp | Ile | Phe | Thr | Thr | Glu |
| | 210 | | | | | 215 | | | | | 220 | | | | |
| Ile | Thr | Ala | Asp | Ala | Val | Gly | Asn | Phe | Leu | Thr | Gln | Asn | Asp | Ala | Lys |
| 225 | | | | | 230 | | | | | 235 | | | | | 240 |
| Ser | Asn | Gln | Gln | Arg | Leu | Ser | Tyr | Asp | Val | Ala | Gly | Gln | Leu | Lys | Ala |
| | | | | 245 | | | | | 250 | | | | | 255 | |
| Ser | Trp | Leu | Thr | Ile | Lys | Gly | Gln | Asn | Glu | Gln | Val | Ile | Val | Asn | Ser |
| | | | 260 | | | | | 265 | | | | | 270 | | |
| Leu | Thr | Tyr | Ser | Ala | Ala | Gly | Gln | Lys | Leu | Arg | Glu | Glu | Gln | Gly | Asn |
| | | | 275 | | | | | 280 | | | | | 285 | | |
| Gly | Val | Val | Thr | Glu | Tyr | Ser | Tyr | Glu | Ala | Gln | Thr | Trp | Arg | Leu | Ile |

-continued

```
                290                 295                 300
Gly Val Thr Ala Tyr Arg Gln Ser Asp Lys Arg Leu Gln Asp Leu
305                 310                 315                 320

Val Tyr Asn Tyr Asp Pro Val Gly Asn Leu Leu Asn Ile Arg Asn Asn
                325                 330                 335

Ala Glu Ala Thr Arg Phe Trp Arg Asn Gln Ile Val Glu Pro Glu Asn
                340                 345                 350

His Tyr Ala Tyr Asp Ser Leu Tyr Gln Leu Ile Ser Ala Ser Gly Arg
                355                 360                 365

Glu Ile Ala Ser Ile Gly Gln Gln Gly Ser Arg Leu Pro Val Pro Ile
370                 375                 380

Ile Pro Leu Pro Ala Asn Asp Val Tyr Thr Arg Tyr Thr Arg Thr
385                 390                 395                 400

Tyr His Tyr Asp Arg Gly Gly Asn Leu Cys Gln Ile Arg His Cys Ala
                405                 410                 415

Pro Ala Thr Asp Asn Lys Tyr Thr Thr Lys Ile Thr Val Ser Asn Arg
                420                 425                 430

Ser Asn Arg Ala Val Trp Asp Thr Leu Thr Thr Asp Pro Ala Lys Val
                435                 440                 445

Asp Thr Leu Phe Asp His Gly His Gln Leu Gln Leu Gln Ser Gly
            450                 455                 460

Gln Thr Leu Cys Trp Asn Tyr Arg Gly Glu Leu Gln Ile Thr Lys
465                 470                 475                 480

Ile Gln Arg Asp Glu Lys Pro Ala Asp Lys Glu Arg Tyr Arg Tyr Gly
                485                 490                 495

Val Gly Ala Ala Arg Val Val Lys Ile Ser Thr Gln Ala Gly Gly
            500                 505                 510

Ser Ser His Val Gln Arg Val Val Tyr Leu Pro Gly Leu Glu Leu Arg
            515                 520                 525

Thr Thr Gln His Asp Ala Thr Leu Ile Glu Asp Leu Gln Val Ile Ile
            530                 535                 540

Met Gly Glu Ala Gly Arg Ala Gln Val Arg Val Leu His Trp Glu Ile
545                 550                 555                 560

Pro Pro Pro Asp Asn Leu Asn Asn Asp Ser Leu Arg Tyr Ser Tyr Asp
                565                 570                 575

Ser Leu Met Gly Ser Ser Gln Leu Glu Leu Asp Gly Ala Gly Gln Ile
            580                 585                 590

Ile Thr Gln Glu Glu Tyr Tyr Pro Tyr Gly Gly Thr Ala Ile Trp Ala
            595                 600                 605

Ala Arg Asn Gln Thr Glu Ala Asn Tyr Lys Thr Ile Arg Tyr Ser Gly
            610                 615                 620

Lys Glu Arg Asp Ala Thr Gly Leu Tyr Tyr Gly His Arg Tyr Tyr
625                 630                 635                 640

Gln Pro Trp Leu Gly Arg Trp Leu Ser Ala Asp Pro Ala Gly Thr Val
                645                 650                 655

Asp Gly Leu Asn Leu Tyr Arg Met Val Arg Asn Asn Pro Ile Thr Tyr
                660                 665                 670

Arg Asp Ala Asp Gly Leu Ala Pro Ile Gly Asp Lys Ile Ser Glu Gly
                675                 680                 685

Ile Tyr Glu Pro Glu Leu Arg Val Gly Leu Glu Arg Asp Asp Pro Asn
            690                 695                 700

Val Arg Asp Tyr Asp Arg Val Tyr Pro Asp Thr Ala Lys Thr Glu Met
705                 710                 715                 720
```

Ile Glu Ala Thr Ala Thr Thr Ile Ala Pro Ser Gln Met Leu Ser Ala
            725                 730                 735

His Ala Phe Ala Ser Val Pro Ile Leu Thr Asp Leu Phe Asn Pro Gln
        740                 745                 750

Thr Ala Arg Leu Ser Gln Lys Thr Thr Asp Ile Val Leu Asn Thr Gln
            755                 760                 765

Gly Gly Gly Asp Leu Ile Phe Thr Gly Met Asn Ile Lys Gly Lys Gly
        770                 775                 780

Lys Glu Phe Asn Ala Leu Lys Ile Val Asp Thr Tyr Gly Gly Glu Met
785                 790                 795                 800

Pro Asp Ser Lys Thr Ala Ile Ser Ala Tyr Trp Leu Pro Gln Gly Gly
            805                 810                 815

Tyr Thr Asp Ile Pro Ile His Pro Thr Gly Ile Gln Lys Tyr Leu Phe
        820                 825                 830

Thr Pro Ala Phe Ser Gly Cys Thr Leu Ala Val Asp Lys Leu Asn Glu
            835                 840                 845

Asn Thr Leu Arg Ala Tyr His Val Glu Gly Ser Lys Glu Asp Ala Gln
850                 855                 860

Tyr Asn Asn Leu Ala Val Ala Ala His Gly Glu Gly Leu Val Met Ala
865                 870                 875                 880

Met Glu Phe Pro Asp Tyr Gly Phe His Thr Asp Lys Thr Gly Gln Arg
            885                 890                 895

Leu Arg Asn Thr Gln Gly Phe Ala Phe Met Ser Tyr Asn Gln Ser Gln
            900                 905                 910

Lys Lys Trp Glu Ile His Tyr Gln Arg Gln Ala Leu Thr Ser Asn Thr
            915                 920                 925

Gly Ile Met Asn Val Ser Ala Lys Asn Lys Ile Arg Leu Asn Ala Pro
        930                 935                 940

Ser His Val Lys Asn Ser Ser Ile Lys Gly Thr Glu Ile Met Thr Thr
945                 950                 955                 960

His Phe

<210> SEQ ID NO 5
<211> LENGTH: 3822
<212> TYPE: DNA
<213> ORGANISM: Xenorhabdus bovienii

<400> SEQUENCE: 5
gatctcacaa agaccaaaac aaaggggatg tatatttatt ctgacatgac cacaaaagtc    60
atgattgata gtgagatcaa aaattatcaa aacagcgttt accgagagtt cgatacattg   120
acccagcgac ggttaaataa ccgttatgcg gcgaattatg attatccgtc ttccgttgca   180
gtcagtagtg gttacgagtg gggcgattac tctctgagta tggtttatga cagtaaaatt   240
gcttccattg ctaccgtcgg aactacttca tcagagatca aattgaaaat cgatgccgac   300
ctgcgggtaa tttataacgg ggttgaaggc aggcagcgtc accaatgtgc tctgatgcaa   360
aaatttggtc agttaggtga taaatttatt gtttacgaag acctgaaaat tgacagagag   420
aatcagagtg caggcaataa caatctcttt tatcccgttt atcaatacag tggcaatgtc   480
agtaaattgt caaagggcg tttattagtt tatagaaaa gttcatcatc ttatgtcaag   540
gcagatattg ggccagggca cgatccgctc attaatgaaa atgctcaaaa accttatggt   600
tatgttgaag acagcaaaaa tgaccccgcc gcgctgaaaa ataacatgac actgacggat   660
aacgcgggta tttctacgaa ggtcgcatca ccaagagata tcgatactgc tgtaacgccg   720

```
gcaaatatca cgattaaggc cagtgcaggc agcagtaaac ctgtagagtt taacgctggc      780
acatctgtca taaatctgcc caacaacaac ttggaagaaa tgatctataa cttccatgat      840
atggaattca ctatcccact gacagaattt aaggacaacc aagtcgaggt ggagatagtg      900
ctgaccggga aaacggatga tggccgggtt ctgggaagtg aaacctttaa ttttaccgtt      960
acacagaaaa ttctgaatga acagtcaggg ttgctgacgc tcaatactgc tgcgtctaaa     1020
gcccaatatc tgcaatgggg gccttaccgt acccgcatta ataccttatt tgccagaaat     1080
atggtggaac gggcagaaac gggcattgat accctgctga caatggatac caacaactg      1140 cctgaaccta aaatgggaga tgggggatat attagtgtca ccttacccaa atatgatcca     1200
gataagcatg gtagtaccag aaacgccgcg gtcacacttt atcaggaaaa agatggtgta     1260
gactcaacaa cgcattacgg cttctgggac gggtcgttaa cagatgcaga acaaaccatc     1320
aaactgttta ttccattaac tagcacgaaa gaacctttct ataacacgat tgattttcca     1380
tcttcgataa gtgacgggct tcaagttttt ctaaaaagcg ctaaggaagg tttgctggcc     1440
ggaaccttaa aaacagcgtt tactccatct gaggataaga aggccaatat tgtcttcacg     1500
gaatatcccc tgtttcggg tacgccaccc atgaaggttg aactgctgtc caaatattat     1560
gatcagccga tggattttaa cggcgccaac tccctctact tctgggaatt gttctattac     1620
agcccgatgc tggtagcgca gcgcttgttg caggaacaaa attttgatga agccaatcat     1680
tggctgaaat atgtttacag ccctgagggc tatatcgtca aggtgagat tgcgccgtat     1740 cattggaatt gccggccact ggaagaagat acttcgtgga actctaaccc gctggattcc     1800 acagacccg atgccgtcgc ccaagatgat ccgatgcact ataaagtttc taccttcatg     1860
cggatgctcg atctgctgat tgcccgtggc gacaaggctt accgccagct tgagcgggat     1920
actttgaatg aagccaagct ctggtatata caggcactga atctattggg ggatgagcag     1980 tttgtggcg tggatggcaa ctggtctgaa cccacgttgg aaaccgcagc ggataagacg     2040
gtggaacagg attatcagca tgcgctgatg ttaattcgcc tggtacagcc cgccgaatat     2100
accgctaact cactgaccaa cctatttttg cctcaacaaa atgacaaact gaatggctac     2160
tggcaaacat tgaagcagcg cttgtataac ctgcgtcata acctcaccat tgatggcctg     2220
ccgctgtcac tgcctattta cgccaaacct gccgatccta aagccttgtt gagtgcggcg     2280
gtgaatgctt cccagggagg cacggatctg ccaaatccgg aaatgccact tcatcgtttc     2340
cccatcatgt tggataacgc gaagagcata gtcagtcaac tcattcagtt tggttctacc     2400
ttacagggga tcattgaacg tcaggatgca gaagcgctca acgaattgct gcaaaatcaa     2460
gcgcgtgaac tgacgctgat cagcattcag atgcagaata aaacgctgga agaattggat     2520
gcggaaaaag aagtactgaa acaatcccga ctaggggcgc aatcacgctt tgacagctat     2580
agcaagctgt acgatgaaaa catcaacgat ggcgaaaaaa ctgctatgga tttgcgtact     2640
gctgccagca cgataagtac tgccctggaa gccgctaaat tggcagaggc cggtgccgat     2700
atgttcccaa atatcttcgg tcttgctggt ggtggcagcc gatgggggc tatccctggc     2760 gcacttgctt ctgtgatggg ctttaccgcc ggcacactca atacgaaagc cgaacgaacc     2820
acacagtctg aaatttaccg ccgccgccgt caggagtggg aaattcagcg caccaatgca     2880
gatcatgaag ttaagcaaat tgacgctcaa ttgaaatcac tggaaatccg gcgtgaagcg     2940
gcagacatgc agaaaaccta tctggaaacc cagcaggctc agacacaggc acaattggaa     3000
ttcctgcaac gtaaattcag taacagagcg ttgtacaact ggatgcgggg tcgtctggcc     3060
```

```
gccatttact tccagttcta tgatcttgcc acctctcgtt gcctgatggc acagcaagcc    3120
taccagtggg aaaccaatga tacagcagcc agctttatca atcgggggc atggcaggga    3180 acctatgctg gcctgctcgc cggcgagtct ctgatactga accttgtcca gatggaagat    3240
gccttcatga aaaagatga acgggcattg gaaatcacgc gtaccgtttc gttggctgag    3300
gtttaccgtt ctctgcctga tgccgataaa ttcatacttc ctgacgcagt tgctgattta    3360
ttgaactccc cggggaaatc attcgggaaa gatcagaaca cactaaaaat tgagacgaat    3420
caactggaag catccgtaaa tctgtctggt ctcaacattt ggggagatta cccggaacaa    3480
cttggcgcgc tcgtcgcat caaacaagtg agtgtttccc tgcctgcctt gcttggaccg    3540
tatcaggatg tacaggccat cttgagctat agcggtgaca tgaagggcat tcccaaaggt    3600
tgcagtgcta tcgcggtatc caatggcatg aatgacagcg gcaattcca gttggatttc    3660 aatgacacca ataccctgcc atttgaaggg atcaatattc cgaaagataa agatcaaagt    3720
gcactggtgc tgagtttccc caacgcggac gctaaacaga aaacgatgtt gctcagtttg    3780
agcgacatca ttctgcacat tcgctacacc attcgcaaat aa                      3822
```

<210> SEQ ID NO 6
<211> LENGTH: 1273
<212> TYPE: PRT
<213> ORGANISM: Xenorhabdus bovienii

<400> SEQUENCE: 6

```
Asp Leu Thr Lys Thr Lys Thr Lys Gly Met Tyr Ile Tyr Ser Asp Met
1               5                   10                  15

Thr Thr Lys Val Met Ile Asp Ser Glu Ile Lys Asn Tyr Gln Asn Ser
            20                  25                  30

Val Tyr Arg Glu Phe Asp Thr Leu Thr Gln Arg Arg Leu Asn Asn Arg
        35                  40                  45

Tyr Ala Ala Asn Tyr Asp Tyr Pro Ser Val Ala Val Ser Ser Gly
    50                  55                  60

Tyr Glu Trp Gly Asp Tyr Ser Leu Ser Met Val Tyr Asp Ser Lys Ile
65                  70                  75                  80

Ala Ser Ile Ala Thr Val Gly Thr Thr Ser Ser Glu Ile Lys Leu Lys
                85                  90                  95

Ile Asp Ala Asp Leu Arg Val Ile Tyr Asn Gly Val Glu Gly Arg Gln
            100                 105                 110

Arg His Gln Cys Ala Leu Met Gln Lys Phe Gly Gln Leu Gly Asp Lys
        115                 120                 125

Phe Ile Val Tyr Glu Asp Leu Lys Ile Asp Arg Glu Asn Gln Ser Ala
    130                 135                 140

Gly Asn Asn Asn Leu Phe Tyr Pro Val Tyr Gln Tyr Ser Gly Asn Val
145                 150                 155                 160

Ser Lys Leu Ser Lys Gly Arg Leu Leu Val Tyr Arg Glu Ser Ser Ser
                165                 170                 175

Ser Tyr Val Lys Ala Asp Ile Gly Pro Gly His Asp Pro Leu Ile Asn
            180                 185                 190

Glu Asn Ala Gln Lys Pro Tyr Gly Tyr Val Glu Asp Ser Lys Asn Asp
        195                 200                 205

Pro Ala Ala Leu Lys Asn Asn Met Thr Leu Thr Asp Asn Ala Gly Ile
    210                 215                 220

Ser Thr Lys Val Ala Ser Pro Arg Asp Ile Asp Thr Ala Val Thr Pro
225                 230                 235                 240
```

```
Ala Asn Ile Thr Ile Lys Ala Ser Ala Gly Ser Ser Lys Pro Val Glu
            245                 250                 255

Phe Asn Ala Gly Thr Ser Val Ile Asn Leu Pro Asn Asn Leu Glu
            260                 265                 270

Glu Met Ile Tyr Asn Phe His Asp Met Glu Phe Thr Ile Pro Leu Thr
            275                 280                 285

Glu Phe Lys Asp Asn Gln Val Glu Val Glu Ile Val Leu Thr Gly Lys
            290                 295                 300

Thr Asp Asp Gly Arg Val Leu Gly Ser Glu Thr Phe Asn Phe Thr Val
305                 310                 315                 320

Thr Gln Lys Ile Leu Asn Glu Gln Ser Gly Leu Leu Thr Leu Asn Thr
                325                 330                 335

Ala Ala Ser Lys Ala Gln Tyr Leu Gln Trp Gly Pro Tyr Arg Thr Arg
            340                 345                 350

Ile Asn Thr Leu Phe Ala Arg Asn Met Val Glu Arg Ala Glu Thr Gly
            355                 360                 365

Ile Asp Thr Leu Leu Thr Met Asp Thr Gln Gln Leu Pro Glu Pro Lys
            370                 375                 380

Met Gly Asp Gly Gly Tyr Ile Ser Val Thr Leu Pro Lys Tyr Asp Pro
385                 390                 395                 400

Asp Lys His Gly Ser Thr Arg Asn Ala Ala Val Thr Leu Tyr Gln Glu
            405                 410                 415

Lys Asp Gly Val Asp Ser Thr Thr His Tyr Gly Phe Trp Asp Gly Ser
            420                 425                 430

Leu Thr Asp Ala Glu Gln Thr Ile Lys Leu Phe Ile Pro Leu Thr Ser
            435                 440                 445

Thr Lys Glu Pro Phe Tyr Asn Thr Ile Asp Phe Pro Ser Ser Ile Ser
            450                 455                 460

Asp Gly Leu Gln Val Phe Leu Lys Ser Ala Lys Glu Gly Leu Leu Ala
465                 470                 475                 480

Gly Thr Leu Lys Thr Ala Phe Thr Pro Ser Glu Asp Lys Lys Ala Asn
            485                 490                 495

Ile Val Phe Thr Glu Tyr Thr Pro Val Ser Gly Thr Pro Met Lys
            500                 505                 510

Val Glu Leu Leu Ser Lys Tyr Tyr Asp Gln Pro Met Asp Phe Asn Gly
            515                 520                 525

Ala Asn Ser Leu Tyr Phe Trp Glu Leu Phe Tyr Tyr Ser Pro Met Leu
            530                 535                 540

Val Ala Gln Arg Leu Leu Gln Glu Gln Asn Phe Asp Glu Ala Asn His
545                 550                 555                 560

Trp Leu Lys Tyr Val Tyr Ser Pro Glu Gly Tyr Ile Val Lys Gly Glu
            565                 570                 575

Ile Ala Pro Tyr His Trp Asn Cys Arg Pro Leu Glu Glu Asp Thr Ser
            580                 585                 590

Trp Asn Ser Asn Pro Leu Asp Ser Thr Asp Pro Asp Ala Val Ala Gln
            595                 600                 605

Asp Asp Pro Met His Tyr Lys Val Ser Thr Phe Met Arg Met Leu Asp
            610                 615                 620

Leu Leu Ile Ala Arg Gly Asp Lys Ala Tyr Arg Gln Leu Glu Arg Asp
625                 630                 635                 640

Thr Leu Asn Glu Ala Lys Leu Trp Tyr Ile Gln Ala Leu Asn Leu Leu
                645                 650                 655

Gly Asp Glu Gln Phe Val Ala Leu Asp Gly Asn Trp Ser Glu Pro Thr
```

-continued

```
                 660                 665                 670
Leu Glu Thr Ala Ala Asp Lys Thr Val Glu Gln Asp Tyr Gln His Ala
                 675                 680                 685

Leu Met Leu Ile Arg Leu Val Gln Pro Ala Glu Tyr Thr Ala Asn Ser
                 690                 695                 700

Leu Thr Asn Leu Phe Leu Pro Gln Gln Asn Asp Lys Leu Asn Gly Tyr
705                 710                 715                 720

Trp Gln Thr Leu Lys Gln Arg Leu Tyr Asn Leu Arg His Asn Leu Thr
                 725                 730                 735

Ile Asp Gly Leu Pro Leu Ser Leu Pro Ile Tyr Ala Lys Pro Ala Asp
                 740                 745                 750

Pro Lys Ala Leu Leu Ser Ala Ala Val Asn Ala Ser Gln Gly Gly Thr
                 755                 760                 765

Asp Leu Pro Asn Pro Glu Met Pro Leu His Arg Phe Pro Ile Met Leu
                 770                 775                 780

Asp Asn Ala Lys Ser Ile Val Ser Gln Leu Ile Gln Phe Gly Ser Thr
785                 790                 795                 800

Leu Gln Gly Ile Ile Glu Arg Gln Asp Ala Glu Ala Leu Asn Glu Leu
                 805                 810                 815

Leu Gln Asn Gln Ala Arg Glu Leu Thr Leu Ile Ser Ile Gln Met Gln
                 820                 825                 830

Asn Lys Thr Leu Glu Glu Leu Asp Ala Glu Lys Glu Val Leu Lys Gln
                 835                 840                 845

Ser Arg Leu Gly Ala Gln Ser Arg Phe Asp Ser Tyr Ser Lys Leu Tyr
                 850                 855                 860

Asp Glu Asn Ile Asn Asp Gly Glu Lys Thr Ala Met Asp Leu Arg Thr
865                 870                 875                 880

Ala Ala Ser Thr Ile Ser Thr Ala Leu Glu Ala Ala Lys Leu Ala Glu
                 885                 890                 895

Ala Gly Ala Asp Met Phe Pro Asn Ile Phe Gly Leu Ala Gly Gly Gly
                 900                 905                 910

Ser Arg Trp Gly Ala Ile Pro Gly Ala Leu Ala Ser Val Met Gly Phe
                 915                 920                 925

Thr Ala Gly Thr Leu Asn Thr Lys Ala Glu Arg Thr Thr Gln Ser Glu
                 930                 935                 940

Ile Tyr Arg Arg Arg Arg Gln Glu Trp Glu Ile Gln Arg Thr Asn Ala
945                 950                 955                 960

Asp His Glu Val Lys Gln Ile Asp Ala Gln Leu Lys Ser Leu Glu Ile
                 965                 970                 975

Arg Arg Glu Ala Ala Asp Met Gln Lys Thr Tyr Leu Glu Thr Gln Gln
                 980                 985                 990

Ala Gln Thr Gln Ala Gln Leu Glu Phe Leu Gln Arg Lys Phe Ser Asn
                 995                 1000                1005

Arg Ala Leu Tyr Asn Trp Met Arg Gly Arg Leu Ala Ala Ile Tyr
                 1010                1015                1020

Phe Gln Phe Tyr Asp Leu Ala Thr Ser Arg Cys Leu Met Ala Gln
                 1025                1030                1035

Gln Ala Tyr Gln Trp Glu Thr Asn Asp Thr Ala Ala Ser Phe Ile
                 1040                1045                1050

Lys Ser Gly Ala Trp Gln Gly Thr Tyr Ala Gly Leu Leu Ala Gly
                 1055                1060                1065

Glu Ser Leu Ile Leu Asn Leu Val Gln Met Glu Asp Ala Phe Met
                 1070                1075                1080
```

Lys Lys Asp Glu Arg Ala Leu Glu Ile Thr Arg Thr Val Ser Leu
    1085                1090                1095

Ala Glu Val Tyr Arg Ser Leu Pro Asp Ala Asp Lys Phe Ile Leu
    1100                1105                1110

Pro Asp Ala Val Ala Asp Leu Leu Asn Ser Pro Gly Lys Ser Phe
    1115                1120                1125

Gly Lys Asp Gln Asn Thr Leu Lys Ile Glu Thr Asn Gln Leu Glu
    1130                1135                1140

Ala Ser Val Asn Leu Ser Gly Leu Asn Ile Trp Gly Asp Tyr Pro
    1145                1150                1155

Glu Gln Leu Gly Ala Ala Arg Arg Ile Lys Gln Val Ser Val Ser
    1160                1165                1170

Leu Pro Ala Leu Leu Gly Pro Tyr Gln Asp Val Gln Ala Ile Leu
    1175                1180                1185

Ser Tyr Ser Gly Asp Met Lys Gly Ile Pro Lys Gly Cys Ser Ala
    1190                1195                1200

Ile Ala Val Ser Asn Gly Met Asn Asp Ser Gly Gln Phe Gln Leu
    1205                1210                1215

Asp Phe Asn Asp Thr Lys Tyr Leu Pro Phe Glu Gly Ile Asn Ile
    1220                1225                1230

Pro Lys Asp Lys Asp Gln Ser Ala Leu Val Leu Ser Phe Pro Asn
    1235                1240                1245

Ala Asp Ala Lys Gln Lys Thr Met Leu Leu Ser Leu Ser Asp Ile
    1250                1255                1260

Ile Leu His Ile Arg Tyr Thr Ile Arg Lys
    1265                1270

<210> SEQ ID NO 7
<211> LENGTH: 4595
<212> TYPE: DNA
<213> ORGANISM: Xenorhabdus bovienii

<400> SEQUENCE: 7
tctagaacta gtgtcgacta aagaagaagg agatatacca tgaaacaaga cagccaggac      60
atgacagtaa cacagctgtc cctgcccaaa gggggcggtg cgatcagtgg catgggtgac     120
actatcagca atgcagggcc ggatgggatg gcttcgcttt ccgtgccttt gcctatctct     180
gccggtcggg ggggcgcacc gaatttatcc ctgaactaca gtagcggagc aggaaacggg     240
tcatttggta ttggctggca atccagtacc atggctatca gccgtcgtac tcaacatggc     300
gtaccgcaat atcacggcga agatactttt ttatgtccga tgggagaagt gatggcggtt     360
gccgtcaatc agagcgggca acccgatgtg cgtaaaaccg ataaactatt aggcgggcaa     420
ctgcctgtta cttataccgt tacgcgtcat cagcccagaa atattcagca cttcagcaaa     480
cttgaatact ggcagccccc aacgatgtgt gaaaccacgc cttttggtt aatgtattca     540 cccgatggac aaattcacat tttcggaaaa actgagcagg ctcagatcgc taacccggca     600
gaggtttcac agattgccca atggcttttg aagaaaccg taacaccagc gggagaacac     660
atttattacc agtatcgggc agaagacgat atcggttgtg atgacagcga aaaaaatgcc     720
caccctaatg ccagtgctca acgttatttg actcaggtga actacggcaa tattacacct     780
gaatccagcc tgcttgtgct gaagaatacg ccaccggcgg ataacgaatg ctattccat      840 ttggttttg attatggtga acgagcgcag gaaataaaca cggttcctcc tttcaaagca     900
ccttcaaaca actggaaaat acggccagac cgtttctccc gctttgaata tggttttgag     960

```
gtgcgaaccc gccgcctgtg tcaacaaatt ctgatgttcc atcgcctgaa atcccttgca    1020
ggagaacaga ttgacggaga agaaatccct gccttggttg cccgtctgct tctcagttat    1080
gacctgaacg acagcgtgac aacccttacc gccattcggc aaatggcgta tgaaactgac    1140
gcaaccttaa tcgctttacc gccactggag tttgactatc agccctttga ggcaaaagtc    1200
acgcagaaat ggcaggaaat gcctcaattg gccggattga atgcccaaca accttaccaa    1260
ctcgtcgatc tctatggtga aggtatctcc ggcatcttgt atcaggacag acccggagca    1320
tggtggtatc aggcaccgat ccgtcagaaa aacgttgaag atattaacgc tgtcaccctat   1380 agcccaataa accccttacc taagatcccc agccagcagg acagagcaac gttgatggat    1440
atcgacggtg atggacatct ggattgggtg atcgctggcg caggtattca ggggcggtac    1500
agtatgcagc cgaatggaga gtggacacac tttattccca tttctgcact gccaacagaa    1560
tattttcatc cacaggcaca actggcggat ctggtggggg ccgggttatc tgatttagcg    1620
ctgattggcc ccagaagtgt gcgtttatat gccaacgacc gaggaaactg gaaagcgggt    1680
attaatgtta tgccacctga tggtgtgaat ttgccgatat ttggtggtga tgccagcagt    1740
ctggtcgcat tttctgacat gttgggatcg ggacagcagc atttggtgga aattgccgct    1800
cagagcgtca aatgctggcc gaatctagga catggccgtt ttggtgcggc tattttgctg    1860
ccggggttta gccagccgaa tggaacattc aatgctaacc aagttttttct ggcagatatc   1920 gatggttccg gcaccgccga catcatctat gcacacagta cgtatctgga tatttacctg    1980
aacgaaagcg gcaaccgttt cagtgcaccc gttcggctta atttgccgga aggggtgatg    2040
tttgacaata cctgtcagtt acaggtgtcg gatattcaag gattgggcgc tgccagcatt    2100
gtactgaccg tacctcatat gacaccgcgc cattggcgtt atgattttac tcacaataaa    2160
ccttggctgc tcaatgtcat caacaacaat cgtggcgcag aaaccacgtt gttttaccgt    2220
agttctgccc aattctggct ggatgaaaaa agtcagatcg aagagctggg aaaatttgca    2280
gcgagttatc tgcctttccc catacatttg ttgtggcgca atgaggcgct ggatgaaatt    2340
actggtaatc gactgactaa ggtcatgaat tatgcccacg gtgcatggga tggcagagag    2400
agagaatttt gcggatttgg ccgtgtaacg caaattgata ccgacgaatt tgccaaggga    2460
accacagaga aagcgccgga tgaaaatatc tatccttccc gtagcataag ctggtttgcc    2520
acgggtttac cagaagtgga ttctcaactt ccggcagaat actggcgtgg tgacgatcag    2580
gcatttgccg gctttacacc gcgcttcact cgttatgaaa aggtaatgc ggggcaagag     2640 ggcaggata ccccgattaa agaaccgacc gaaacagaag cgtattggct taaccgcgcc     2700
atgaaaggcc aattactgcg cagtgaagtc tatggtgacg acaaaacaga aaaagctaaa    2760
attccgtaca ccgtcacaga agctcgctgt caggtcagat taattcccag caatgacgaa    2820
gccgcgccgt cgtcttggac gtcgatcatt gaaaaccgca gttatcacta tgagcgtatc    2880
gtcgtcgatc cgagttgcaa acaacaggtc gtgctcaagg cggatgaata tggcttccca    2940
ctggcaaaag tagatatcgc ctatccacgg cgcaataaac cggcacagaa cccttatccg    3000
gattcgttac cggatactct gttcgccgat agctatgacg accagcaaaa acagttatat    3060
ctgcaaaaac agcagcagag ctattaccac ctgacccagc aggatgattg ggttctgggt    3120
ttgacggata gccgatacag cgaagtttat cattatgcgc aaactgacgc tcaaagtgac    3180
atccccaagg cagggctgat attggaagac ctgctgaaag ttgacggcct gataggtaaa    3240
gacaagactt ttatctattt agggcagcag cgagtggctt atgtgggagg agatgcgaaa    3300
```

```
aaaccgacac gtcaggtgcg ggtggcttat acagaaaccg ctgcttttga tgacaatgcg    3360
ctgcacgcct ttgatggcgt gattgccct gatgaactga cgcaacagtt gctggcgggt    3420
ggatacctgc tcgtgccgca gatttctgat gtggcaggca gtagtgaaaa ggtatgggta    3480
gctcggcagg gatacaccga atacggcagt gctgctcaat tctaccggcc actcatccag    3540
cgcaaaagct tgctgaccgg aaaatatacc cttagttggg atacgcacta ttgtgtggtg    3600
gtaaaaaccg aagatggtgc gggaatgacc acgcaagcga gtacgatta ccgcttcctg    3660
cttccggcgc aattgacaga tatcaatgac aaccagcaca tcgtgacatt taatgcattg    3720
gggcaggtga cttccagccg tttctggggc acagaaaatg gcaaaataag cggttactcg    3780
acgccggaga gtaaaccgtt cacagtaccc gataccgtcg aaaaagccct tgccttgcaa    3840
ccgacgatcc cggtttcaca gtgcaacatt tatgtgccgg atagttggat gcggcttctg    3900
ccccaacagt ctctgactgg ccagctaaaa gaggggaaa ctttgtggaa cgcattacac    3960
cgggcgggtg tagtaacgga agacggtttg atctgtgaac tggcctatcg tcgttggatc    4020
aaacgtcagg caacgtcttc aatgatggcc gtgacattac agcaaatctt ggctcagact    4080
ccacgacaac ctccgcatgc catgacgatc acgacagatc gttatgacag cgattctcag    4140
cagcaacttc ggcagtcgat agtattgagt gatggttttg gtcgcgtatt gcaaagcgcc    4200
cagcgtcatg aagcaggaga ggcatggcag cgtcagaag atggttcttt ggttgtcgat    4260
aataccggta acccgttgt tgctaatacc acaacgcgct gggcagtatc cggtcgcaca    4320
gaatacgacg gcaaagggca ggcgatcaga gcttacctgc cttattatct caatgattgg    4380
cgctatgtca gtgatgacag cgcccgggat gacctgtacg ccgataccca tttttacgat    4440
cctctggggc gtgaatatca ggtaaaaacc gcgaaaggat tttggcgtga aaacatgttt    4500
atgccgtggt ttgtcgtcaa tgaagatgaa aatgacacag cagcacgttt aacatcttaa    4560
ttaatgcggc cgcaggcctc tgtaagactc tcgag                              4595

<210> SEQ ID NO 8
<211> LENGTH: 2947
<212> TYPE: DNA
<213> ORGANISM: Xenorhabdus bovienii
<400> SEQUENCE: 8
tctagaacta gtaggcctta agaagagag agatatacca tgaatgtttt taatccaact     60
ttatatgccg gtacaccgac tgtcaccgtc atggacaatc gagggctgtc agtgcgggat    120
attgcttatc accgtacaac agcaggagag caggctgaca ctcgcatcac ccgccatcaa    180
tacagtcccc ataatttttt aatcgagagc attgatccac gccttttga tttgcaatct    240
cagagcacca taaaacctaa tttcacctac tgtcctgcct gaagggtga tgtcctacgg    300
acagagagtg tggatgccgg acaaactgtc attttgagtg acatcgaagg tcgtccgtta    360
ctgaatatca gtgcgatggg tgtcgtcaaa cactggcaat atgaagagag tacattgccg    420
gggcgcttgc tcgctgtcag tgaacggaag aatgaggctt caacaccca aattattgaa    480
cggtttattt ggtcgggaaa tagcccatca gaaaagatc acaatttggc gggaaaatat    540
cttcgtcatt atgataccgc cggattaaac cagcttaatg ctgtgtctct gaccagcgtg    600
gatctctcac aatcccgtca gttattgcag atgatgtca cagcagattg gagcggaagt    660
gacgaatccc agtggaagac gcgactgagt aacgacatat tcacaaccga aatcaccgct    720
gatgcggttg gcaatttctt gactcagaat gatgccaaaa gcaaccagca acgattgtcc    780
tatgatgtgg cagggcagtt aaaggcaagc tggctgacga taaaaggcca gaatgagcag    840
```

```
gtgatagtta actccctgac ttactccgcc gcagggcaga aactgcgtga agagcagggt    900
aacggcgttg tcactgaata ctcctatgaa gcacaaacct ggcgtttgat aggtgtaacg    960
gcttaccgtc agtcagataa aaaaagattg caggatcttg tctataacta tgatccggtc   1020
ggtaatctcc tgaatattcg caataatgca gaggcaaccc gtttctggcg taatcagata   1080
gtagaaccag agaaccacta tgcttatgac tcgctttatc aactcatcag tgctagtggt   1140
cgagaaatcg ccagtatcgg tcagcagggc agccggctgc ctgtaccgat tattcctctt   1200
cctgccaatg acgatgttta tactcgctac acccgcacat atcactatga tcgcggtgga   1260
aatctctgcc agatccggca ttgcgctcct gctacagata taagtacac cacaaagatc   1320
accgtatcga atcgtagtaa tcgtgcagta tgggatacct tgaccacaga tcccgccaaa   1380
gtggataccc tgtttgatca tggagggcat caacttcaac tccagtcagg ccagacttta   1440
tgttggaact atcggggtga actacagcaa ataacaaaga tacagcgtga cgaaaaaccc   1500
gcagataaag agcggtatcg ctatggtgtt ggggctgcgc gggtcgtgaa atcagcaca   1560
cagcaggcgg ggggaagcag ccatgtgcag cgtgttgttt atctgccggg gttggaacta   1620
cgcacaactc agcatgatgc gacattaatc gaagacttac aggtgattat catgggtgaa   1680
gcaggacgtg ctcaggtacg cgtacttcat tgggaaatac caccaccgga taatcttaac   1740
aatgactcac tgcgttacag ctacgatagt ttgatgggtt ccagtcagct tgaattggat   1800
ggagcagggc agattattac gcaggaagaa tactacccct atggaggtac agcaatatgg   1860
gcggcaagaa accagaccga agccaattac aaaaccattc gctactccgg caaagagcgt   1920
gatgcgacgg ggctttatta ctacgggcac cgttattatc agccgtggct agggcgctgg   1980
ttgagcgcag atcccgccgg aaccgtggac ggactgaatc tatatcgaat ggtgaggaat   2040
aacccgatta cttaccggga tgcagatggg cttgcgccga taggcgataa gatcagcgaa   2100
gggatttatg agcctgagtt gcgagttggt cttgaacgag atgacccaaa tgtcagagat   2160
tatgaccggg tttatcctga tacggccaag acagagatga tcgaagcaac tgcgaccaca   2220
attgctccca gtcaaatgtt atcggcgcat gcttttgcat ctgtacctat attgacagat   2280
ttgtttaatc ctcaaacagc aaggctttct caaaagacaa cggatattgt attaaacaca   2340
caaggtggag cgatttaat ctttactggc atgaatatta aggtaaggg aaaagaattt    2400
aatgcattaa aaatcgttga tacttatggc ggagaaatgc ctgatagcaa aaccgctatt   2460
tcagcatatt ggcttccgca aggtgggtat actgatattc cgatacatcc gactggaata   2520
caaaagtatt tgtttacgcc tgcgtttagt ggttgcactc tggcagtaga taagcttaac   2580
gaaaatacat tacgggcgta tcacgtcgaa ggaagtaagg aagatgctca atataataat   2640
ttagcagttg cagcgcacgg agagggttg gtcatggcta tggaatttcc tgactatgga   2700
tttcatacag acaaaacagg gcaaagacta aggaacacac agggatttgc gtttatgtcc   2760
tacaatcaat cccagaaaaa atgggaaatt cattatcaaa ggcaagcatt gacatcaaac   2820
accggtatca tgaatgttag tgctaaaaac aagattcgat tgaatgcccc cagtcatgta   2880
aaaaatagct caatcaaagg aactgaaata atgacgacac atttttaatt aatgcggccg   2940
cctcgag                                                              2947
```

<210> SEQ ID NO 9
<211> LENGTH: 7508
<212> TYPE: DNA
<213> ORGANISM: Xenorhabdus bovienii

<400> SEQUENCE: 9

```
tctagaacta gtgtcgacta aagaagaagg agatatacca tgaaacaaga cagccaggac    60
atgacagtaa cacagctgtc cctgcccaaa gggggcggtg cgatcagtgg catgggtgac   120
actatcagca atgcagggcc ggatgggatg gcttcgcttt ccgtgccttt gcctatctct   180
gccggtcggg ggggcgcacc gaatttatcc ctgaactaca gtagcggagc aggaaacggg   240
tcatttggta ttggctggca atccagtacc atggctatca gccgtcgtac tcaacatggc   300
gtaccgcaat atcacggcga agatactttt ttatgtccga tgggagaagt gatggcggtt   360
gccgtcaatc agagcgggca acccgatgtg cgtaaaaccg ataaactatt aggcgggcaa   420
ctgcctgtta cttataccgt tacgcgtcat cagcccagaa atattcagca cttcagcaaa   480
cttgaatact ggcagccccc aacgcatgtg aaaccacgc ctttttggtt aatgtattca   540
cccgatggac aaattcacat tttcggaaaa actgagcagg ctcagatcgc taacccggca   600
gaggtttcac agattgccca atggcttttg aagaaaccg taacaccagc gggagaacac   660
atttattacc agtatcgggc agaagacgat atcggttgtg atgacagcga aaaaaatgcc   720
caccctaatg ccagtgctca acgttatttg actcaggtga actacggcaa tattacacct   780
gaatccagcc tgcttgtgct gaagaatacg ccaccggcgg ataacgaatg gctattccat   840
ttggtttttg attatggtga acgagcgcag gaaataaaca cggttcctcc tttcaaagca   900
ccttcaaaca actggaaaat acggccagac cgtttctccc gctttgaata tggttttgag   960
gtgcgaaccc gccgcctgtg tcaacaaatt ctgatgttcc atcgcctgaa atcccttgca  1020
ggagaacaga ttgacggaga agaaatccct gccttggttg cccgtctgct tctcagttat  1080
gacctgaacg acagcgtgac aaccctaccc gccattcggc aaatggcgta tgaaactgac  1140
gcaaccttaa tcgctttacc gccactggag tttgactatc agcccttga ggcaaaagtc  1200
acgcagaaat ggcaggaaat gcctcaattg gccggattga atgccaaca accttaccaa  1260
ctcgtcgatc tctatggtga aggtatctcc ggcatcttgt atcaggacag acccggagca  1320
tggtggtatc aggcaccgat ccgtcagaaa aacgttgaag atattaacgc tgtcacctat  1380
agcccaataa acccttacc taagatcccc agccagcagg acagagcaac gttgatggat  1440
atcgacggtg atggacatct ggattgggtg atcgctggcg caggtattca ggggcggtac  1500
agtatgcagc cgaatggaga gtggacacac tttattccca tttctgcact gccaacagaa  1560
tattttcatc cacaggcaca actggcggat ctggtggggg ccgggttatc tgatttagcg  1620
ctgattggcc ccagaagtgt gcgtttatat gccaacgacc gaggaaactg gaaagcgggt  1680
attaatgtta tgccacctga tggtgtgaat ttgccgatat ttggtggtga tgccagcagt  1740
ctggtcgcat tttctgacat gttgggatcg ggacagcagc atttggtgga aattgccgct  1800
cagagcgtca aatgctggcc gaatctagga catggccgtt ttggtgcggc tattttgctg  1860
ccggggttta gccagccgaa tggaacattc aatgctaacc aagttttct ggcagatatc  1920
gatggttccg gcaccgccga catcatctat gcacacagta cgtatctgga tatttacctg  1980
aacgaaagcg gcaaccgttt cagtgcaccc gttcggctta atttgccgga aggggtgatg  2040
tttgacaata cctgtcagtt acaggtgtcg gatattcaag gattgggcgc tgccagcatt  2100
gtactgaccg tacctcatat gacaccgcgc cattggcgtt atgatttac tcacaataaa  2160
ccttggctgc tcaatgtcat caacaacaat cgtggcgcag aaaccacgtt gttttaccgt  2220
agttctgccc aattctggct ggatgaaaaa agtcagatcg aagagctggg aaaatttgca  2280
gcgagttatc tgcctttccc catacatttg ttgtggcgca atgaggcgct ggatgaaatt  2340
```

-continued

```
actggtaatc gactgactaa ggtcatgaat tatgcccacg gtgcatggga tggcagagag    2400
agagaatttt gcggatttgg ccgtgtaacg caaattgata ccgacgaatt tgccaaggga    2460
accacagaga aagcgccgga tgaaaatatc tatccttccc gtagcataag ctggtttgcc    2520
acgggtttac cagaagtgga ttctcaactt ccggcagaat actggcgtgg tgacgatcag    2580
gcatttgccg gctttacacc gcgcttcact cgttatgaaa aaggtaatgc ggggcaagag    2640
gggcaggata ccccgattaa agaaccgacc gaaacagaag cgtattggct taaccgcgcc    2700
atgaaaggcc aattactgcg cagtgaagtc tatggtgacg acaaaacaga aaagctaaa     2760 attccgtaca ccgtcacaga agctcgctgt caggtcagat taattcccag caatgacgaa    2820
gccgcgccgt cgtcttggac gtcgatcatt gaaaaccgca gttatcacta tgagcgtatc    2880
gtcgtcgatc cgagttgcaa acaacaggtc gtgctcaagg cggatgaata tggcttccca    2940
ctggcaaaag tagatatcgc ctatccacgg cgcaataaac cggcacagaa cccttatccg    3000
gattcgttac cggatactct gttcgccgat agctatgacg accagcaaaa acagttatat    3060
ctgacaaaac agcagcagag ctattaccac ctgacccagc aggatgattg ggttctgggt    3120
ttgacggata gccgatacag cgaagtttat cattatgcgc aaactgacgc tcaaagtgac    3180
atccccaagg cagggctgat attggaagac ctgctgaaag ttgacggcct gataggtaaa    3240
gacaagactt ttatctattt agggcagcag cgagtggctt atgtgggagg agatgcagaa    3300
aaaccgacac gtcaggtgcg ggtggcttat acagaaaccg ctgcttttga tgacaatgcg    3360
ctgcacgcct ttgatggcgt gattgcccct gatgaactga cgcaacagtt gctggcgggt    3420
ggatacctgc tcgtgccgca gatttctgat gtggcaggca gtagtgaaaa ggtatgggta    3480
gctcggcagg atacaccga atacggcagt gctgctcaat tctaccggcc actcatccag    3540
cgcaaaagct tgctgaccgg aaaatatacc cttagttggg atacgcacta ttgtgtggtg    3600
gtaaaaaccg aagatggtgc gggaatgacc acgcaagcga agtacgatta ccgcttcctg    3660
cttccggcgc aattgacaga tatcaatgac aaccagcaca tcgtgacatt taatgcattg    3720
gggcaggtga cttccagccg tttctggggc acagaaaatg gcaaaataag cggttactcg    3780
acgccggaga gtaaaccgtt cacagtaccc gataccgtcg aaaaagccct tgccttgcaa    3840
ccgacgatcc cggtttcaca gtgcaacatt tatgtgccgg atagttggat gcggcttctg    3900
ccccaacagt ctctgactgg ccagctaaaa gagggggaaa ctttgtggaa cgcattacac    3960
cgggcgggtg tagtaacgga agacggtttg atctgtgaac tggcctatcg tcgttggatc    4020
aaacgtcagg caacgtcttc aatgatggcc gtgacattac agcaaatctt ggctcagact    4080
ccacgacaac ctccgcatgc catgacgatc acgacagatc gttatgacag cgattctcag    4140
cagcaacttc ggcagtcgat agtattgagt gatggttttg gtcgcgtatt gcaaagcgcc    4200
cagcgtcatg aagcaggaga ggcatggcag cgtgcagaag atggttcttt ggttgtcgat    4260
aataccggta aacccgttgt tgctaatacc acaacgcgct gggcagtatc cggtcgcaca    4320
gaatacgacg gcaaagggca ggcgatcaga gcttacctgc cttattatct caatgattgg    4380
cgctatgtca gtgatgacag cgcccgggat gacctgtacg ccgataccca tttttacgat    4440
cctctggggc gtgaatatca ggtaaaaacc gcgaaaggat tttggcgtga aaacatgttt    4500
atgccgtggt ttgtcgtcaa tgaagatgaa atgacacag cagcacgttt aacatcttaa    4560
ttaatgcggc cgcaggcctt aaagaagaga gagatatacc atgaatgttt ttaatccaac    4620
tttatatgcc ggtacaccga ctgtcaccgt catggacaat cgagggctgt cagtgcggga    4680
```

```
tattgcttat caccgtacaa cagcaggaga gcaggctgac actcgcatca cccgccatca   4740
atacagtccc cataattttt taatcgagag cattgatcca cgccttttg atttgcaatc    4800
tcagagcacc ataaaaccta atttcaccta ctgtcctgcc ttgaagggtg atgtcctacg   4860
gacagagagt gtggatgccg gacaaactgt cattttgagt gacatcgaag gtcgtccgtt   4920
actgaatatc agtgcgatgg gtgtcgtcaa acactggcaa tatgaagaga gtacattgcc   4980
ggggcgcttg ctcgctgtca gtgaacggaa gaatgaggct tcaacacccc aaattattga   5040
acggtttatt tggtcgggaa atagcccatc agaaaagat cacaatttgg cgggaaaata    5100
tcttcgtcat tatgataccg ccggattaaa ccagcttaat gctgtgtctc tgaccagcgt   5160
ggatctctca caatcccgtc agttattgca ggatgatgtc acagcagatt ggagcggaag   5220
tgacgaatcc cagtggaaga cgcgactgag taacgacata ttcacaaccg aaatcaccgc   5280
tgatgcggtt ggcaatttct tgactcagaa tgatgccaaa agcaaccagc aacgattgtc   5340
ctatgatgtg gcagggcagt taaaggcaag ctggctgacg ataaaaggcc agaatgagca   5400
ggtgatagtt aactccctga cttactccgc cgcagggcag aaactgcgtg aagagcaggg   5460
taacggcgtt gtcactgaat actcctatga agcacaaacc tggcgtttga taggtgtaac   5520
ggcttaccgt cagtcagata aaaaaagatt gcaggatctt gtctataact atgatccggt   5580
cggtaatctc ctgaatattc gcaataatgc agaggcaacc cgtttctggc gtaatcagat   5640
agtagaacca gagaaccact atgcttatga ctcgctttat caactcatca gtgctagtgg   5700
tcgagaaatc gccagtatcg gtcagcaggg cagccggctg cctgtaccga ttattcctct   5760
tcctgccaat gacgatgttt atactcgcta cacccgcaca tatcactatg atcgcggtgg   5820
aaatctctgc cagatccggc attgcgctcc tgctacagat aataagtaca ccacaaagat   5880
caccgtatcg aatcgtagta atcgtgcagt atgggatacc ttgaccacag atcccgccaa   5940
agtggatacc ctgtttgatc atggagggca tcaacttcaa ctccagtcag gccagacttt   6000
atgttggaac tatcggggtg aactacagca ataacaaag atacagcgtg acgaaaaacc    6060
cgcagataaa gagcggtatc gctatggtgt tggggctgcg cgggtcgtga aaatcagcac   6120
acagcaggcg ggggaagca gccatgtgca gcgtgttgtt tatctgccgg ggttggaact    6180
acgcacaact cagcatgatg cgacattaat cgaagactta caggtgatta tcatgggtga   6240
agcaggacgt gctcaggtac gcgtacttca ttgggaaata ccaccaccgg ataatcttaa   6300
caatgactca ctgcgttaca gctacgatag tttgatgggt tccagtcagc ttgaattgga   6360
tggagcaggg cagattatta cgcaggaaga atactacccc tatggaggta cagcaatatg   6420
ggcggcaaga aaccagaccg aagccaatta caaaaccatt cgctactccg gcaaagagcg   6480
tgatgcgacg gggctttatt actacgggca ccgttattat cagccgtggc tagggcgctg   6540
gttgagcgca gatcccgccg gaaccgtgga cggactgaat ctatatcgaa tggtgaggaa   6600
taacccgatt acttaccggg atgcagatgg gcttgcgccg ataggcgata agatcagcga   6660
agggatttat gagcctgagt tgcgagttgg tcttgaacga gatgacccaa atgtcagaga   6720
ttatgaccgg gtttatcctg atacggccaa gacagagatg atcgaagcaa ctgcgaccac   6780
aattgctccc agtcaaatgt tatcggcgca tgcttttgca tctgtaccta tattgacaga   6840
tttgttaat cctcaaacag caaggctttc tcaaaagaca acggatattg tattaaacac    6900
acaaggtgga ggcgatttaa tctttactgg catgaatatt aaaggtaagg gaaaagaatt   6960
taatgcatta aaaatcgttg atacttatgg cggagaaatg cctgatagca aaaccgctat   7020
ttcagcatat tggcttccgc aaggtgggta tactgatatt ccgatacatc cgactggaat   7080
```

-continued

```
acaaaagtat tgtttacgc ctgcgtttag tggttgcact ctggcagtag ataagcttaa    7140
cgaaaataca ttacgggcgt atcacgtcga aggaagtaag gaagatgctc aatataataa    7200
tttagcagtt gcagcgcacg gagagggttt ggtcatggct atggaatttc ctgactatgg    7260
atttcataca gacaaaacag ggcaaagact aaggaacaca cagggatttg cgtttatgtc    7320
ctacaatcaa tcccagaaaa aatgggaaat tcattatcaa aggcaagcat tgacatcaaa    7380
caccggtatc atgaatgtta gtgctaaaaa caagattcga ttgaatgccc ccagtcatgt    7440
aaaaaatagc tcaatcaaag gaactgaaat aatgacgaca cattttttaat taatgcggcc    7500 gcctcgag                                                              7508

<210> SEQ ID NO 10
<211> LENGTH: 7605
<212> TYPE: DNA
<213> ORGANISM: Xenorhabdus bovienii

<400> SEQUENCE: 10
atgtataata cagaaaatat attaattagg cttaataggg aaagttccca ggaaccgatg      60
acattggctc atattatgcc aatctcattt tcagcattca ggaagaagt caaagatacg     120 ctgaattggg gagaaagcca tcacctgtat ctagccgcca agaaagccga aaagaaaaac     180 aggattttg aagcacgttt attatcccgc gccaatccgc agttaagggg ggctgttcgt     240
ctcggcattc agcaactctc gcagcggcaa agttacgata cgctatttgg cggtcggtcg     300
ggtaagtatg tattacccgg ctctgtcgcc tctatgttct caccggcagc ctacctgaca     360
gagctgtatc gggaatccag acacctgcat tcagaatcgt ccatctacca tcttgataag     420
cgtcgccctg atttgcaaag cataatgttg acgcaggaaa accaagatca aacactctcc     480
acacttgaac tatcaaatga cattctcttt gatggcataa aaaataagaa aaaactcaac     540
aaaaatgaag atgtactgaa atgttgtct gattggcgtc tgagtggaaa tacgccttac     600
catcaaccct ttgaaaccct atctaacatt gtctcccagc ttgatcctca gctcagtcag     660
gttagtcagt cgccaaaagt gattggttta ttgtccccgg tcagcctatt ggggatatca     720
agtcaaattt caccagaact gtataaaatc ctgacggaag aaattacggc tgagaatgcg     780
caagacatgt ataagaaaaa tttcggtgac ttgccgattt ctgcactgtc taatcctaac     840
tatttgatga atattatga tattgatgca gatactctcc gtgctgtaat gggtatctat     900
ggatcaggcc aaaacgatga tgaacccgca ttcatcagcg atcaggccat agtgacttac     960
cttgatgata aaattctttt cgttacttac ctgattactc gcaccaaagg cgagacttat    1020
gactggcagg ttaattttat cgaagctatt cccacaaaag atggcaaatt aaaatattgg    1080
tataatttta aagctccggc ttccagtgca gtttccacca aaatttcgct gaatgggcag    1140
actatcttcg acagacctga ttggctgccg gagctcaata agacttattc agatatcgtt    1200
gatttcccca gtgatgttga tagaaaaaaa tttactctga aattcgaaag agcagcctct    1260
ggcagtggag gtagttttaa tacggatgcg acattctcaa ttgaaacggt attacctcaa    1320 ctcttttttcc tcaaattgaa taaagttatt cgcctttaca aaaaaccgg tatcacgctg    1380 gaacaaattg aaactgctgt ggattcgat aatgcccaac aacaaataac cgaaacaatt    1440
ctgaaaaaga tattttatac aacctactat attaataggt attatttgag tttcaatgat    1500
gcactggtgt tatgtaatac cgcaatatct cagcacagct ataatgatca gccttctcat    1560
tttgacctta ttttttaataa cccgccattg aatggaaact attaccaatt gggcggggat    1620
```

-continued

```
aaaattcaag ttgatccaga tcaggcagat tatgaacaat ataatcaacg gcgtgaaatg    1680
ctcaagcacg cgttgaaagt taatgacagt gaattattca cactatctaa gattctggat    1740
caagaaaata cgtcaggtat cgacaataac cttgctacgg atttatctgc gctgtaccgc    1800
gtacgaatgc ttgcttacat tcaccaactt tctatcaatg aattggctat cctgctaaaa    1860
ctctcgccat atgctgaaga gtcttttaac aaaatcagta cggaaaagtt aatcgaagtc    1920
attgaatatc tttacagtat cacccagtgg ttacagacac agaaaatcag cgtttatacc    1980
ctgtatatga tgacgaccac aacctacagt acagttttat cacccgatat taacaatctg    2040
atcgagacgc tacgggcggg aatgcagaac aaaaccgtac cagacgatcc acttcaactt    2100
atcaagacct tggcacccct cattgcagcg gcactgaaac tttcttcggc atttgtggct    2160
gagtcgatcc tgatatggat caacaagatc aaacccaatg gcatggatgt cgccgccttc    2220
tggaaatcca ttgagtctac aaaaaatccg atagaaccga acagcatggt attttgtcag    2280
gtgctggggc agttggcatt gatttattta gccacgcaac taacgaaaaa tgctctgaat    2340
ctggcggtga caactaaagt gattatcggt cactccggca gcatcgatca tctgggcaaa    2400
gatactgaga cggtgagaca gcttagccgt tttgcgggat ggtgtaattc actgggcagc    2460
aatacagaca cagtactgac agctctgcaa agtaacaact tggatagcac tattctggcg    2520
agtgccatga ggatggatga gaggctgctt tcaaccgcca gtgaacaggc taaccttaat    2580
aaacaggttg cagaaaaaga taagtatgca gattggccag aaatagacag tgttctgcaa    2640
tggctagcag tggccaatgt gatgaaaacc agcccgaata agattaatgc tcttctgcaa    2700
ttggactatc tgaaagatca gaatactaca gaagtttctt acgaaacatg gagccaatcg    2760
gcggatatac tggcggctgg gctgaataat aatcaatcag atattctgaa acaagcctta    2820
gaggaagaag ccagtgccgc attaagccaa tattacatcc gtgaagttgt ggatagcgcg    2880
gctgaggtga tagatagaaa tgatctgtat ggttacctgc tgatagataa tcaaatctcc    2940
gcacaggtcg aaacgacacg gctggctgag gccattgcca gtatccagca atatatcaac    3000
cgtgcattga atggccgtga gagtacccct gccaccgatg tcatgacagg ccagtttttat    3060 caggattggg atcgttataa caaacgctac agcacatggg cgggtgtttc cacgctggtt    3120
tactatcctg aaaactatat cgatccgacc atgcgtatcg gtcagaccca catgatggat    3180
gaattgctgc aatccgtcag ccagagtcaa ctcagtgttg ataccgttga agatgcgttt    3240
aaaacctatc tgacccgctt tgaacaaatt gccaacctga ctgtcgtcag tggctatcat    3300
gataatgtga acatttcaca agggaacagt taccttgtcg gtaaagggga aacggatgcc    3360
aaccaatatt attggcgcaa actggatcac agcaaatccc gtcagggcaa gattgccgcc    3420
aatgcgtgga gtgaatgggc aaaaattgac agcccggtca atccctatca gggcttaatt    3480
aagccggtta tctataaatc ccgcctgtat attgtctggc tggaaaaacg ggtgattact    3540
gtttcagaaa gcaaagacgg cgcaataaca tcgaaagata tcattaaata tgaaatcaaa    3600 atcgccccata tcagacatga tggcacatgg aatacgccta tcacgttaga tgtcagcgat    3660
atcttcagcg catataacga tacagacctg gccaatctgg ctatgtattg ctctgaatat    3720
acgggagaaa gtaccttact cttattactg tatgtcaaac aggctgatac ggcgggaaac    3780
aaagatctca caaagaccaa aacaaagggg atgtatattt attctgacat gaccacaaaa    3840
gtcatgattg atagtgagat caaaaattat caaaacagcg tttaccgaga gttcgataca    3900
ttgacccagc gacggttaaa taaccgttat gcggcgaatt atgattatcc gtcttccgtt    3960
gcagtcagta gtggttacga gtggggcgat tactctctga gtatggttta tgacagtaaa    4020
```

```
attgcttcca ttgctaccgt cggaactact tcatcagaga tcaaattgaa aatcgatgcc     4080
gacctgcggg taatttataa cggggttgaa ggcaggcagc gtcaccaatg tgctctgatg     4140
caaaaatttg gtcagttagg tgataaattt attgtttacg aagacctgaa aattgacaga     4200
gagaatcaga gtgcaggcaa taacaatctc ttttatcccg tttatcaata cagtggcaat     4260
gtcagtaaat tgtcaaaagg gcgtttatta gtttatagag aaagttcatc atcttatgtc     4320
aaggcagata ttgggccagg gcacgatccg ctcattaatg aaaatgctca aaaaccttat     4380
ggttatgttg aagacagcaa aaatgacccc gccgcgctga aaaataacat gacactgacg     4440
gataacgcgg gtatttctac gaaggtcgca tcaccaagag atatcgatac tgctgtaacg     4500
ccggcaaata tcacgattaa ggccagtgca ggcagcagta aacctgtaga gtttaacgct     4560
ggcacatctg tcataaatct gcccaacaac aacttggaag aaatgatcta taacttccat     4620
gatatggaat tcactatccc actgacagaa tttaaggaca accaagtcga ggtggagata     4680
gtgctgaccg ggaaaacgga tgatggccgg gttctgggaa gtgaaacctt taattttacc     4740
gttacacaga aaattctgaa tgaacagtca ggggttgctga cgctcaatac tgctgcgtct     4800
aaagcccaat atctgcaatg ggggccttac cgtacccgca ttaatacctt atttgccaga     4860
aatatggtgg aacgggcaga aacgggcatt gatacccctgc tgacaatgga tacccaacaa     4920
ctgcctgaac ctaaaatggg agatggggga tatattagtg tcaccttacc caaatatgat     4980
ccagataagc atggtagtac cagaaacgcc gcggtcacac tttatcagga aaagatggt     5040 gtagactcaa caacgcatta cggcttctgg gacgggtcgt taacgatgc agaacaaacc     5100 atcaaactgt ttattccatt aactagcacg aaagaacctt tctataacac gattgatttt     5160
ccatcttcga taagtgacgg gcttcaagtt tttctaaaaa gcgctaagga aggtttgctg     5220
gccggaacct taaaaacagc gtttactcca tctgaggata agaaggccaa tattgtcttc     5280
acggaatata cccctgtttc gggtacgcca cccatgaagg ttgaactgct gtccaaatat     5340
tatgatcagc cgatggattt taacggcgcc aactccctct acttctggga attgttctat     5400
tacagcccga tgctggtagc gcagcgcttg ttgcaggaac aaaatttttga tgaagccaat     5460 cattggctga aatatgttta cagccctgag ggctatatcg tcaaaggtga gattgcgccg     5520
tatcattgga attgccggcc actggaagaa gatacttcgt ggaactctaa cccgctggat     5580
tccacagacc ccgatgccgt cgcccaagat gatccgatgc actataaagt ttctaccttc     5640
atgcggatgc tcgatctgct gattgcccgt ggcgacaagg cttaccgcca gcttgagcgg     5700
gatactttga tgaagccaa gctctggtat atacaggcac tgaatctatt ggggatgag     5760 cagtttgtgg cgctggatgg caactggtct gaacccacgt tggaaaccgc agcggataag     5820
acggtggaac aggattatca gcatgcgctg atgttaattc gcctggtaca gcccgccgaa     5880
tataccgcta actcactgac caacctattt ttgcctcaac aaaatgacaa actgaatggc     5940
tactggcaaa cattgaagca gcgcttgtat aacctgcgtc ataacctcac cattgatggc     6000
ctgccgctgt cactgcctat ttacgccaaa cctgccgatc taaagccttt gttgagtgcg     6060
gcggtgaatg cttcccaggg aggcacggat ctgccaaatc cggaaatgcc acttcatcgt     6120
ttccccatca tgttggataa cgcgaagagc atagtcagtc aactcattca gtttggttct     6180
accttacagg ggatcattga acgtcaggat gcagaagcgc tcaacgaatt gctgcaaaat     6240
caagcgcgtg aactgacgct gatcagcatt cagatgcaga ataaaacgct ggaagaattg     6300
gatgcggaaa aagaagtact gaaacaatcc cgactagggg cgcaatcacg ctttgacagc     6360
```

```
tatagcaagc tgtacgatga aaacatcaac gatggcgaaa aaactgctat ggatttgcgt    6420
actgctgcca gcacgataag tactgccctg gaagccgcta aattggcaga ggccggtgcc    6480
gatatgttcc caaatatctt cggtcttgct ggtggtggca gccgatgggg ggctatccct    6540
ggcgcacttg cttctgtgat gggctttacc gccggcacac tcaatacgaa agccgaacga    6600
accacacagt ctgaaattta ccgccgccgc cgtcaggagt gggaaattca gcgcaccaat    6660
gcagatcatg aagttaagca aattgacgct caattgaaat cactggaaat ccggcgtgaa    6720
gcggcagaca tgcagaaaac ctatctggaa acccagcagg ctcagacaca ggcacaattg    6780
gaattcctgc aacgtaaatt cagtaacaga gcgttgtaca actggatgcg gggtcgtctg    6840
gccgccattt acttccagtt ctatgatctt gccacctctc gttgcctgat ggcacagcaa    6900
gcctaccagt gggaaaccaa tgatacagca gccagcttta tcaaatcggg ggcatggcag    6960
ggaacctatg ctggcctgct cgccggcgag tctctgatac tgaaccttgt ccagatggaa    7020
gatgccttca tgaaaaaaga tgaacgggca ttggaaatca cgcgtaccgt ttcgttggct    7080
gaggtttacc gttctctgcc tgatgccgat aaattcatac ttcctgacgc agttgctgat    7140
ttattgaact ccccggggaa atcattcggg aaagatcaga acacactaaa aattgagacg    7200
aatcaactgg aagcatccgt aaatctgtct ggtctcaaca tttggggaga ttacccggaa    7260
caacttggcg cggctcgtcg catcaaacaa gtgagtgttt ccctgcctgc cttgcttgga    7320
ccgtatcagg atgtacaggc catcttgagc tatagcggtg acatgaaggg cattcccaaa    7380
ggttgcagtg ctatcgcggt atccaatggc atgaatgaca gcgggcaatt ccagttggat    7440
ttcaatgaca ccaaatacct gccatttgaa gggatcaata ttccgaaaga taaagatcaa    7500
agtgcactgg tgctgagttt ccccaacgcg gacgctaaac agaaaacgat gttgctcagt    7560
ttgagcgaca tcattctgca cattcgctac accattcgca aataa              7605
```

<210> SEQ ID NO 11
<211> LENGTH: 2534
<212> TYPE: PRT
<213> ORGANISM: Xenorhabdus bovienii

<400> SEQUENCE: 11

```
Met Tyr Asn Thr Glu Asn Ile Leu Ile Arg Leu Asn Arg Glu Ser Ser
1               5                   10                  15

Gln Glu Pro Met Thr Leu Ala His Ile Met Pro Ile Ser Phe Ser Ala
                20                  25                  30

Phe Arg Lys Glu Val Lys Asp Thr Leu Asn Trp Gly Glu Ser His His
            35                  40                  45

Leu Tyr Leu Ala Ala Lys Lys Ala Glu Lys Glu Asn Arg Ile Phe Glu
        50                  55                  60

Ala Arg Leu Leu Ser Arg Ala Asn Pro Gln Leu Arg Gly Ala Val Arg
65                  70                  75                  80

Leu Gly Ile Gln Gln Leu Ser Gln Arg Gln Ser Tyr Asp Thr Leu Phe
                85                  90                  95

Gly Gly Arg Ser Gly Lys Tyr Val Leu Pro Gly Ser Val Ala Ser Met
            100                 105                 110

Phe Ser Pro Ala Ala Tyr Leu Thr Glu Leu Tyr Arg Glu Ser Arg His
        115                 120                 125

Leu His Ser Glu Ser Ser Ile Tyr His Leu Asp Lys Arg Arg Pro Asp
    130                 135                 140

Leu Gln Ser Ile Met Leu Thr Gln Glu Asn Gln Asp Gln Thr Leu Ser
145                 150                 155                 160
```

-continued

```
Thr Leu Glu Leu Ser Asn Asp Ile Leu Phe Asp Gly Ile Lys Asn Lys
            165                 170                 175
Lys Lys Leu Asn Lys Asn Glu Asp Val Leu Lys Met Leu Ser Asp Trp
        180                 185                 190
Arg Leu Ser Gly Asn Thr Pro Tyr His Gln Pro Phe Glu Thr Leu Ser
    195                 200                 205
Asn Ile Val Ser Gln Leu Asp Pro Gln Leu Ser Gln Val Ser Gln Ser
210                 215                 220
Pro Lys Val Ile Gly Leu Leu Ser Pro Val Ser Leu Leu Gly Ile Ser
225                 230                 235                 240
Ser Gln Ile Ser Pro Glu Leu Tyr Lys Ile Leu Thr Glu Glu Ile Thr
                245                 250                 255
Ala Glu Asn Ala Gln Asp Met Tyr Lys Lys Asn Phe Gly Asp Leu Pro
            260                 265                 270
Ile Ser Ala Leu Ser Asn Pro Asn Tyr Leu Met Lys Tyr Tyr Asp Ile
        275                 280                 285
Asp Ala Asp Thr Leu Arg Ala Val Met Gly Ile Tyr Gly Ser Gly Gln
    290                 295                 300
Asn Asp Asp Glu Pro Ala Phe Ile Ser Asp Gln Ala Ile Val Thr Tyr
305                 310                 315                 320
Leu Asp Asp Lys Asn Ser Phe Val Thr Tyr Leu Ile Thr Arg Thr Lys
                325                 330                 335
Gly Glu Thr Tyr Asp Trp Gln Val Asn Phe Ile Glu Ala Ile Pro Thr
            340                 345                 350
Lys Asp Gly Lys Leu Lys Tyr Trp Tyr Asn Phe Lys Ala Pro Ala Ser
        355                 360                 365
Ser Ala Val Ser Thr Lys Ile Ser Leu Asn Gly Gln Thr Ile Phe Asp
    370                 375                 380
Arg Pro Asp Trp Leu Pro Glu Leu Asn Lys Thr Tyr Ser Asp Ile Val
385                 390                 395                 400
Asp Phe Pro Ser Asp Val Asp Arg Lys Lys Phe Thr Leu Lys Phe Glu
                405                 410                 415
Arg Ala Ala Ser Gly Ser Gly Ser Phe Asn Thr Asp Ala Thr Phe
            420                 425                 430
Ser Ile Glu Thr Val Leu Pro Gln Leu Phe Phe Leu Lys Leu Asn Lys
        435                 440                 445
Val Ile Arg Leu Tyr Lys Lys Thr Gly Ile Thr Leu Glu Gln Ile Glu
    450                 455                 460
Thr Ala Val Asp Ser Asp Asn Ala Gln Gln Gln Ile Thr Glu Thr Ile
465                 470                 475                 480
Leu Lys Lys Ile Phe Tyr Thr Thr Tyr Tyr Ile Asn Arg Tyr Tyr Leu
                485                 490                 495
Ser Phe Asn Asp Ala Leu Val Leu Cys Asn Thr Ala Ile Ser Gln His
            500                 505                 510
Ser Tyr Asn Asp Gln Pro Ser His Phe Asp Leu Ile Phe Asn Asn Pro
        515                 520                 525
Pro Leu Asn Gly Asn Tyr Tyr Gln Leu Gly Gly Asp Lys Ile Gln Val
    530                 535                 540
Asp Pro Asp Gln Ala Asp Tyr Glu Gln Tyr Asn Gln Arg Arg Glu Met
545                 550                 555                 560
Leu Lys His Ala Leu Lys Val Asn Asp Ser Glu Leu Phe Thr Leu Ser
                565                 570                 575
```

-continued

```
Lys Ile Leu Asp Gln Glu Asn Thr Ser Gly Ile Asp Asn Asn Leu Ala
                580                 585                 590

Thr Asp Leu Ser Ala Leu Tyr Arg Val Arg Met Leu Ala Tyr Ile His
        595                 600                 605

Gln Leu Ser Ile Asn Glu Leu Ala Ile Leu Leu Lys Leu Ser Pro Tyr
    610                 615                 620

Ala Glu Glu Ser Phe Asn Lys Ile Ser Thr Glu Lys Leu Ile Glu Val
625                 630                 635                 640

Ile Glu Tyr Leu Tyr Ser Ile Thr Gln Trp Leu Gln Thr Gln Lys Ile
                645                 650                 655

Ser Val Tyr Thr Leu Tyr Met Met Thr Thr Thr Tyr Ser Thr Val
        660                 665                 670

Leu Ser Pro Asp Ile Asn Asn Leu Ile Glu Thr Leu Arg Ala Gly Met
    675                 680                 685

Gln Asn Lys Thr Val Pro Asp Asp Pro Leu Gln Leu Ile Lys Thr Leu
    690                 695                 700

Ala Pro Phe Ile Ala Ala Leu Lys Leu Ser Ser Ala Phe Val Ala
705                 710                 715                 720

Glu Ser Ile Leu Ile Trp Ile Asn Lys Ile Lys Pro Asn Gly Met Asp
                725                 730                 735

Val Ala Ala Phe Trp Lys Ser Ile Glu Ser Thr Lys Asn Pro Ile Glu
            740                 745                 750

Pro Asn Ser Met Val Phe Cys Gln Val Leu Gly Gln Leu Ala Leu Ile
        755                 760                 765

Tyr Leu Ala Thr Gln Leu Thr Glu Asn Ala Leu Asn Leu Ala Val Thr
    770                 775                 780

Thr Lys Val Ile Ile Gly His Ser Gly Ser Ile Asp His Leu Gly Lys
785                 790                 795                 800

Asp Thr Glu Thr Val Arg Gln Leu Ser Arg Phe Ala Gly Trp Cys Asn
                805                 810                 815

Ser Leu Gly Ser Asn Thr Asp Thr Val Leu Thr Ala Leu Gln Ser Asn
            820                 825                 830

Asn Leu Asp Ser Thr Ile Leu Ala Ser Ala Met Arg Met Asp Glu Arg
        835                 840                 845

Leu Leu Ser Thr Ala Ser Glu Gln Ala Asn Leu Asn Lys Gln Val Ala
    850                 855                 860

Glu Lys Asp Lys Tyr Ala Asp Trp Pro Glu Ile Asp Ser Val Leu Gln
865                 870                 875                 880

Trp Leu Ala Val Ala Asn Val Met Lys Thr Ser Pro Asn Lys Ile Asn
                885                 890                 895

Ala Leu Leu Gln Leu Asp Tyr Leu Lys Asp Gln Asn Thr Thr Glu Val
            900                 905                 910

Ser Tyr Glu Thr Trp Ser Gln Ser Ala Asp Ile Leu Ala Ala Gly Leu
        915                 920                 925

Asn Asn Asn Gln Ser Asp Ile Leu Lys Gln Ala Leu Glu Glu Glu Ala
    930                 935                 940

Ser Ala Ala Leu Ser Gln Tyr Tyr Ile Arg Glu Val Val Asp Ser Ala
945                 950                 955                 960

Ala Glu Val Ile Asp Arg Asn Asp Leu Tyr Gly Tyr Leu Leu Ile Asp
                965                 970                 975

Asn Gln Ile Ser Ala Gln Val Glu Thr Thr Arg Leu Ala Glu Ala Ile
            980                 985                 990

Ala Ser Ile Gln Gln Tyr Ile Asn  Arg Ala Leu Asn Gly  Arg Glu Ser
```

-continued

```
               995                 1000                1005
Thr Pro Ala Thr Asp Val Met Thr Gly Gln Phe Tyr Gln Asp Trp
    1010            1015                1020

Asp Arg Tyr Asn Lys Arg Tyr Ser Thr Trp Ala Gly Val Ser Thr
    1025            1030                1035

Leu Val Tyr Tyr Pro Glu Asn Tyr Ile Asp Pro Thr Met Arg Ile
    1040            1045                1050

Gly Gln Thr His Met Met Asp Glu Leu Leu Gln Ser Val Ser Gln
    1055            1060                1065

Ser Gln Leu Ser Val Asp Thr Val Glu Asp Ala Phe Lys Thr Tyr
    1070            1075                1080

Leu Thr Arg Phe Glu Gln Ile Ala Asn Leu Thr Val Val Ser Gly
    1085            1090                1095

Tyr His Asp Asn Val Asn Ile Ser Gln Gly Asn Ser Tyr Leu Val
    1100            1105                1110

Gly Lys Gly Glu Thr Asp Ala Asn Gln Tyr Tyr Trp Arg Lys Leu
    1115            1120                1125

Asp His Ser Lys Ser Arg Gln Gly Lys Ile Ala Ala Asn Ala Trp
    1130            1135                1140

Ser Glu Trp Ala Lys Ile Asp Ser Pro Val Asn Pro Tyr Gln Gly
    1145            1150                1155

Leu Ile Lys Pro Val Ile Tyr Lys Ser Arg Leu Tyr Ile Val Trp
    1160            1165                1170

Leu Glu Lys Arg Val Ile Thr Val Ser Glu Ser Lys Asp Gly Ala
    1175            1180                1185

Ile Thr Ser Lys Asp Ile Ile Lys Tyr Glu Ile Lys Ile Ala His
    1190            1195                1200

Ile Arg His Asp Gly Thr Trp Asn Thr Pro Ile Thr Leu Asp Val
    1205            1210                1215

Ser Asp Ile Phe Ser Ala Tyr Asn Asp Thr Asp Leu Ala Asn Leu
    1220            1225                1230

Ala Met Tyr Cys Ser Glu Tyr Thr Gly Glu Ser Thr Leu Leu Leu
    1235            1240                1245

Leu Leu Tyr Val Lys Gln Ala Asp Thr Ala Gly Asn Lys Asp Leu
    1250            1255                1260

Thr Lys Thr Lys Thr Lys Gly Met Tyr Ile Tyr Ser Asp Met Thr
    1265            1270                1275

Thr Lys Val Met Ile Asp Ser Glu Ile Lys Asn Tyr Gln Asn Ser
    1280            1285                1290

Val Tyr Arg Glu Phe Asp Thr Leu Thr Gln Arg Arg Leu Asn Asn
    1295            1300                1305

Arg Tyr Ala Ala Asn Tyr Asp Tyr Pro Ser Ser Val Ala Val Ser
    1310            1315                1320

Ser Gly Tyr Glu Trp Gly Asp Tyr Ser Leu Ser Met Val Tyr Asp
    1325            1330                1335

Ser Lys Ile Ala Ser Ile Ala Thr Val Gly Thr Thr Ser Ser Glu
    1340            1345                1350

Ile Lys Leu Lys Ile Asp Ala Asp Leu Arg Val Ile Tyr Asn Gly
    1355            1360                1365

Val Glu Gly Arg Gln Arg His Gln Cys Ala Leu Met Gln Lys Phe
    1370            1375                1380

Gly Gln Leu Gly Asp Lys Phe Ile Val Tyr Glu Asp Leu Lys Ile
    1385            1390                1395
```

-continued

```
Asp Arg Glu Asn Gln Ser Ala Gly Asn Asn Leu Phe Tyr Pro
    1400            1405            1410

Val Tyr Gln Tyr Ser Gly Asn Val Ser Lys Leu Ser Lys Gly Arg
    1415            1420            1425

Leu Leu Val Tyr Arg Glu Ser Ser Ser Tyr Val Lys Ala Asp
    1430            1435            1440

Ile Gly Pro Gly His Asp Pro Leu Ile Asn Glu Asn Ala Gln Lys
    1445            1450            1455

Pro Tyr Gly Tyr Val Glu Asp Ser Lys Asn Asp Pro Ala Ala Leu
    1460            1465            1470

Lys Asn Asn Met Thr Leu Thr Asp Asn Ala Gly Ile Ser Thr Lys
    1475            1480            1485

Val Ala Ser Pro Arg Asp Ile Asp Thr Ala Val Thr Pro Ala Asn
    1490            1495            1500

Ile Thr Ile Lys Ala Ser Ala Gly Ser Ser Lys Pro Val Glu Phe
    1505            1510            1515

Asn Ala Gly Thr Ser Val Ile Asn Leu Pro Asn Asn Asn Leu Glu
    1520            1525            1530

Glu Met Ile Tyr Asn Phe His Asp Met Glu Phe Thr Ile Pro Leu
    1535            1540            1545

Thr Glu Phe Lys Asp Asn Gln Val Glu Val Glu Ile Val Leu Thr
    1550            1555            1560

Gly Lys Thr Asp Asp Gly Arg Val Leu Gly Ser Glu Thr Phe Asn
    1565            1570            1575

Phe Thr Val Thr Gln Lys Ile Leu Asn Glu Gln Ser Gly Leu Leu
    1580            1585            1590

Thr Leu Asn Thr Ala Ala Ser Lys Ala Gln Tyr Leu Gln Trp Gly
    1595            1600            1605

Pro Tyr Arg Thr Arg Ile Asn Thr Leu Phe Ala Arg Asn Met Val
    1610            1615            1620

Glu Arg Ala Glu Thr Gly Ile Asp Thr Leu Leu Thr Met Asp Thr
    1625            1630            1635

Gln Gln Leu Pro Glu Pro Lys Met Gly Asp Gly Gly Tyr Ile Ser
    1640            1645            1650

Val Thr Leu Pro Lys Tyr Asp Pro Asp Lys His Gly Ser Thr Arg
    1655            1660            1665

Asn Ala Ala Val Thr Leu Tyr Gln Glu Lys Asp Gly Val Asp Ser
    1670            1675            1680

Thr Thr His Tyr Gly Phe Trp Asp Gly Ser Leu Thr Asp Ala Glu
    1685            1690            1695

Gln Thr Ile Lys Leu Phe Ile Pro Leu Thr Ser Thr Lys Glu Pro
    1700            1705            1710

Phe Tyr Asn Thr Ile Asp Phe Pro Ser Ser Ile Ser Asp Gly Leu
    1715            1720            1725

Gln Val Phe Leu Lys Ser Ala Lys Glu Gly Leu Leu Ala Gly Thr
    1730            1735            1740

Leu Lys Thr Ala Phe Thr Pro Ser Glu Asp Lys Lys Ala Asn Ile
    1745            1750            1755

Val Phe Thr Glu Tyr Thr Pro Val Ser Gly Thr Pro Pro Met Lys
    1760            1765            1770

Val Glu Leu Leu Ser Lys Tyr Tyr Asp Gln Pro Met Asp Phe Asn
    1775            1780            1785
```

-continued

```
Gly Ala Asn Ser Leu Tyr Phe Trp Glu Leu Phe Tyr Tyr Ser Pro
    1790            1795                1800

Met Leu Val Ala Gln Arg Leu Leu Gln Glu Gln Asn Phe Asp Glu
    1805            1810                1815

Ala Asn His Trp Leu Lys Tyr Val Tyr Ser Pro Glu Gly Tyr Ile
    1820            1825                1830

Val Lys Gly Glu Ile Ala Pro Tyr His Trp Asn Cys Arg Pro Leu
    1835            1840                1845

Glu Glu Asp Thr Ser Trp Asn Ser Asn Pro Leu Asp Ser Thr Asp
    1850            1855                1860

Pro Asp Ala Val Ala Gln Asp Asp Pro Met His Tyr Lys Val Ser
    1865            1870                1875

Thr Phe Met Arg Met Leu Asp Leu Leu Ile Ala Arg Gly Asp Lys
    1880            1885                1890

Ala Tyr Arg Gln Leu Glu Arg Asp Thr Leu Asn Glu Ala Lys Leu
    1895            1900                1905

Trp Tyr Ile Gln Ala Leu Asn Leu Leu Gly Asp Glu Gln Phe Val
    1910            1915                1920

Ala Leu Asp Gly Asn Trp Ser Glu Pro Thr Leu Glu Thr Ala Ala
    1925            1930                1935

Asp Lys Thr Val Glu Gln Asp Tyr Gln His Ala Leu Met Leu Ile
    1940            1945                1950

Arg Leu Val Gln Pro Ala Glu Tyr Thr Ala Asn Ser Leu Thr Asn
    1955            1960                1965

Leu Phe Leu Pro Gln Gln Asn Asp Lys Leu Asn Gly Tyr Trp Gln
    1970            1975                1980

Thr Leu Lys Gln Arg Leu Tyr Asn Leu Arg His Asn Leu Thr Ile
    1985            1990                1995

Asp Gly Leu Pro Leu Ser Leu Pro Ile Tyr Ala Lys Pro Ala Asp
    2000            2005                2010

Pro Lys Ala Leu Leu Ser Ala Ala Val Asn Ala Ser Gln Gly Gly
    2015            2020                2025

Thr Asp Leu Pro Asn Pro Glu Met Pro Leu His Arg Phe Pro Ile
    2030            2035                2040

Met Leu Asp Asn Ala Lys Ser Ile Val Ser Gln Leu Ile Gln Phe
    2045            2050                2055

Gly Ser Thr Leu Gln Gly Ile Ile Glu Arg Gln Asp Ala Glu Ala
    2060            2065                2070

Leu Asn Glu Leu Leu Gln Asn Gln Ala Arg Glu Leu Thr Leu Ile
    2075            2080                2085

Ser Ile Gln Met Gln Asn Lys Thr Leu Glu Glu Leu Asp Ala Glu
    2090            2095                2100

Lys Glu Val Leu Lys Gln Ser Arg Leu Gly Ala Gln Ser Arg Phe
    2105            2110                2115

Asp Ser Tyr Ser Lys Leu Tyr Asp Glu Asn Ile Asn Asp Gly Glu
    2120            2125                2130

Lys Thr Ala Met Asp Leu Arg Thr Ala Ala Ser Thr Ile Ser Thr
    2135            2140                2145

Ala Leu Glu Ala Ala Lys Leu Ala Glu Ala Gly Ala Asp Met Phe
    2150            2155                2160

Pro Asn Ile Phe Gly Leu Ala Gly Gly Gly Ser Arg Trp Gly Ala
    2165            2170                2175

Ile Pro Gly Ala Leu Ala Ser Val Met Gly Phe Thr Ala Gly Thr
```

-continued

```
            2180                2185                2190

Leu Asn Thr Lys Ala Glu Arg Thr Thr Gln Ser Glu Ile Tyr Arg
    2195                2200                2205

Arg Arg Arg Gln Glu Trp Glu Ile Gln Arg Thr Asn Ala Asp His
    2210                2215                2220

Glu Val Lys Gln Ile Asp Ala Gln Leu Lys Ser Leu Glu Ile Arg
    2225                2230                2235

Arg Glu Ala Ala Asp Met Gln Lys Thr Tyr Leu Glu Thr Gln Gln
    2240                2245                2250

Ala Gln Thr Gln Ala Gln Leu Glu Phe Leu Gln Arg Lys Phe Ser
    2255                2260                2265

Asn Arg Ala Leu Tyr Asn Trp Met Arg Gly Arg Leu Ala Ala Ile
    2270                2275                2280

Tyr Phe Gln Phe Tyr Asp Leu Ala Thr Ser Arg Cys Leu Met Ala
    2285                2290                2295

Gln Gln Ala Tyr Gln Trp Glu Thr Asn Asp Thr Ala Ala Ser Phe
    2300                2305                2310

Ile Lys Ser Gly Ala Trp Gln Gly Thr Tyr Ala Gly Leu Leu Ala
    2315                2320                2325

Gly Glu Ser Leu Ile Leu Asn Leu Val Gln Met Glu Asp Ala Phe
    2330                2335                2340

Met Lys Lys Asp Glu Arg Ala Leu Glu Ile Thr Arg Thr Val Ser
    2345                2350                2355

Leu Ala Glu Val Tyr Arg Ser Leu Pro Asp Ala Asp Lys Phe Ile
    2360                2365                2370

Leu Pro Asp Ala Val Ala Asp Leu Leu Asn Ser Pro Gly Lys Ser
    2375                2380                2385

Phe Gly Lys Asp Gln Asn Thr Leu Lys Ile Glu Thr Asn Gln Leu
    2390                2395                2400

Glu Ala Ser Val Asn Leu Ser Gly Leu Asn Ile Trp Gly Asp Tyr
    2405                2410                2415

Pro Glu Gln Leu Gly Ala Ala Arg Arg Ile Lys Gln Val Ser Val
    2420                2425                2430

Ser Leu Pro Ala Leu Leu Gly Pro Tyr Gln Asp Val Gln Ala Ile
    2435                2440                2445

Leu Ser Tyr Ser Gly Asp Met Lys Gly Ile Pro Lys Gly Cys Ser
    2450                2455                2460

Ala Ile Ala Val Ser Asn Gly Met Asn Asp Ser Gly Gln Phe Gln
    2465                2470                2475

Leu Asp Phe Asn Asp Thr Lys Tyr Leu Pro Phe Glu Gly Ile Asn
    2480                2485                2490

Ile Pro Lys Asp Lys Asp Gln Ser Ala Leu Val Leu Ser Phe Pro
    2495                2500                2505

Asn Ala Asp Ala Lys Gln Lys Thr Met Leu Leu Ser Leu Ser Asp
    2510                2515                2520

Ile Ile Leu His Ile Arg Tyr Thr Ile Arg Lys
    2525                2530
```